United States Patent
Klingler et al.

(10) Patent No.: US 9,073,975 B2
(45) Date of Patent: Jul. 7, 2015

(54) CYCLIC PEPTIDES, THEIR PREPARATION AND THEIR USE AS INHIBITORS OF THE PLATELET ADHESION

(75) Inventors: Otmar Klingler, Frankfurt am Main (DE); Horst Blum, Frankfurt am Main (DE); Andreas Lindenschmidt, Frankfurt am Main (DE); Hans Matter, Frankfurt am Main (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 13/818,444

(22) PCT Filed: Jul. 27, 2011

(86) PCT No.: PCT/EP2011/062917
§ 371 (c)(1),
(2), (4) Date: Sep. 10, 2013

(87) PCT Pub. No.: WO2012/013709
PCT Pub. Date: Feb. 2, 2012

(65) Prior Publication Data
US 2014/0011734 A1 Jan. 9, 2014

(30) Foreign Application Priority Data
Jul. 29, 2010 (EP) .................................. 10305842

(51) Int. Cl.
C07K 7/64 (2006.01)
C07K 7/06 (2006.01)
C07K 7/56 (2006.01)
A61K 38/00 (2006.01)

(52) U.S. Cl.
CPC . C07K 7/64 (2013.01); A61K 38/00 (2013.01); C07K 7/06 (2013.01); C07K 7/56 (2013.01)

(58) Field of Classification Search
None
See application file for complete search history.

(56) References Cited

U.S. PATENT DOCUMENTS 5,340,727 A 8/1994 Ruggeri et al.
2009/0010934 A1 1/2009 Deckmyn et al.

OTHER PUBLICATIONS

Benard et al. "Identification of peptide antagonists to glycoprotein Ib[alpha] that selectively inhibit von Willebrand factor dependent platelet aggregation", Biochemistry, American Chemical Society US, vol. 47, No. 16, (Apr. 22, 2008), pp. 4674-4682.*
McEwan et al.: "Glycoprotein Ib[alpha] inhibitor complex structure reveals a combined steric and allosteric mechanism of von Willebrand factor antagonism", Blood, American Society of Hematology USA Nov. 26, 2009, vol. 114, No. 23, pp. 4883-4885.*
Kageyama, S. , et al., "Anti-Human vWF Monoclonal Antibody, AJvW-2 Fab, Inhibits Repetitive Coronary Artery Thrombosis without Bleeding Time Prolongation in Dogs", Thrombosis Research 101 (2001), pp. 395-404.
European Search Report dated Nov. 3, 2010 from corresponding European Patent Application No. 10 30 5842.6.
International Preliminary Report on Patentability and Written Opinion of the International Searching Authority dated Jan. 29, 2013 of corresponding International Application No. PCT/EP2011/062917.
Benard, Susan Adam, "Identification of Peptide Antagonists to Glycoprotein Iba That Selectively Inhibit von Willebrand Factor Dependent Platelet Aggregation", Biochemistry (2008), vol. 47, pp. 4674-4682.
McEwan, Paul A., "Glycoprotein Iba inhibitor complex structure reveals a combined steric and allosteric mechanism of von Willebrand factor antagonism", blood (Nov. 26, 2009), vol. 114, No. 23, pp. 4883-4885.
International Search Report dated Dec. 29, 2011 issued in PCT/EP2011/062917.

* cited by examiner

Primary Examiner — Maury Audet
(74) Attorney, Agent, or Firm — Scully, Scott, Murphy & Presser, P.C.; Sabine Venne-Dunker

(57) ABSTRACT

The present invention relates to compounds of the Formula (I), in which R1, R2, R3, R4, R5, R6, R7, R8, R9, R10, R11, R12, R13, R14, R15, R16, R17, R18, X1, X2, X3 and X4 have the meanings indicated in the claims, and which are valuable pharmacologically active compounds. They are reversible inhibitors of the interaction between the plasma protein von Willebrand factor (vWF) and the blood platelet receptor glycoprotein Ib-IX-V complex (GPIb), and are suitable, for example, for the therapy and prophylaxis of athero-thrombotic diseases. The invention furthermore relates to processes for the preparation of compounds of the Formula (I), their use, in particular as active ingredients in medicaments, and pharmaceutical compositions comprising them.

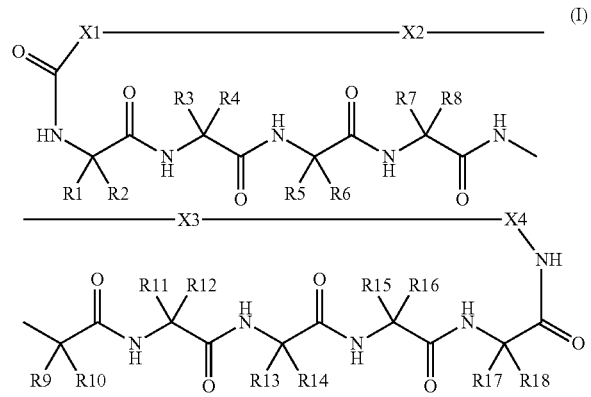

3 Claims, No Drawings

SEQUENCE LISTING

```
<160> NUMBER OF SEQ ID NOS: 114

<210> SEQ ID NO 1
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: Xaa is 7-aminoheptanoic acid

<400> SEQUENCE: 1

Leu His Asn Leu Xaa Thr Glu Arg Met Ala
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: Xaa is 3-aminomethylphenylacetic acid

<400> SEQUENCE: 2

Leu His Asn Leu Xaa Thr Glu Arg Met Ala
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: Xaa is 4-aminomethylphenylacetic acid

<400> SEQUENCE: 3

Leu His Asn Leu Xaa Thr Glu Arg Met Ala
1               5                   10

<210> SEQ ID NO 4
<211> LENGTH: 10
```

```
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: Xaa is 2'-aminomethylbiphenyl-2-ylacetic acid

<400> SEQUENCE: 4

Leu His Asn Leu Xaa Thr Glu Arg Met Ala
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is 2-acetylamino-6-aminoheptanoic acid
<220> FEATURE:
<221> NAME/KEY: MISC_FEATURE
<222> LOCATION: (5)..(5)
<223> OTHER INFORMATION: Xaa is 2-acetylamino-6-aminohexanoic acid

<400> SEQUENCE: 5

Xaa Thr Glu Arg Met Ala Leu His Asn Leu
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is 8-aminooctanoic acid

<400> SEQUENCE: 6

Xaa Thr Glu Arg Met Ala Leu His Asn Leu
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is 7-aminoheptanoic acid

<400> SEQUENCE: 7

Xaa Thr Glu Lys Met Ala Leu His Asn Leu
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
```

```
<223> OTHER INFORMATION: Xaa is 7-aminoheptanoic acid
<220> FEATURE:
<221> NAME/KEY: MISC_FEATURE
<222> LOCATION: (2)..(2)
<223> OTHER INFORMATION: Xaa is 1-aminocyclopropanecarboxylic acid

<400> SEQUENCE: 8

Xaa Xaa Glu Arg Met Ala Leu His Asn Leu
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is 7-aminoheptanoic acid
<220> FEATURE:
<221> NAME/KEY: MISC_FEATURE
<222> LOCATION: (2)..(2)
<223> OTHER INFORMATION: Xaa is 1-aminocyclopentanecarboxylix acid

<400> SEQUENCE: 9

Xaa Xaa Glu Arg Met Ala Leu His Asn Leu
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is 7-aminoheptanoic acid

<400> SEQUENCE: 10

Xaa Asp Glu Arg Met Ala Leu His Asn Leu
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is 6-aminohexanoic acid

<400> SEQUENCE: 11

Xaa Thr Glu Arg Met Ala Leu His Asn Leu
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is 7-aminoheptanoic acid

<400> SEQUENCE: 12
```

Xaa Leu Glu Arg Met Ala Leu His Asn Leu
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: Xaa is Nle
<220> FEATURE:
<221> NAME/KEY: MISC_FEATURE
<222> LOCATION: (10)..(10)
<223> OTHER INFORMATION: Xaa is 7-aminoheptanoic acid

<400> SEQUENCE: 13

Thr Glu Arg Met Ala Xaa His Asn Leu Xaa
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (10)..(10)
<223> OTHER INFORMATION: Xaa is 7-aminoheptanoic acid

<400> SEQUENCE: 14

Thr Glu Arg Met Ala Ile His Asn Leu Xaa
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (10)..(10)
<223> OTHER INFORMATION: Xaa is 9-aminononanoic acid

<400> SEQUENCE: 15

Thr Glu Arg Met Ala Leu His Asn Leu Xaa
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: Xaa is cyclohexylalanine
<220> FEATURE:
<221> NAME/KEY: MISC_FEATURE
<222> LOCATION: (10)..(10)
<223> OTHER INFORMATION: Xaa is 7-aminoheptanoic acid

<400> SEQUENCE: 16

Thr Glu Arg Met Ala Xaa His Asn Leu Xaa
1               5                   10

```
<210> SEQ ID NO 17
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: Xaa is cyclohexylalanine
<220> FEATURE:
<221> NAME/KEY: MISC_FEATURE
<222> LOCATION: (10)..(10)
<223> OTHER INFORMATION: Xaa is 7-aminoheptanoic acid

<400> SEQUENCE: 17

Thr Glu Arg Xaa Ala Leu His Asn Leu Xaa
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (10)..(10)
<223> OTHER INFORMATION: Xaa is 7-aminoheptanoic acid

<400> SEQUENCE: 18

Thr Glu Arg Ile Ala Leu His Asn Leu Xaa
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: Xaa is Nva
<220> FEATURE:
<221> NAME/KEY: MISC_FEATURE
<222> LOCATION: (10)..(10)
<223> OTHER INFORMATION: Xaa is 7-aminoheptanoic acid

<400> SEQUENCE: 19

Thr Glu Arg Met Ala Xaa His Asn Leu Xaa
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: Xaa is cyclohexylglycine
<220> FEATURE:
<221> NAME/KEY: MISC_FEATURE
<222> LOCATION: (10)..(10)
<223> OTHER INFORMATION: Xaa is 7-aminoheptanoic acid

<400> SEQUENCE: 20

Thr Glu Arg Met Ala Xaa His Asn Leu Xaa
```

<210> SEQ ID NO 21
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (10)..(10)
<223> OTHER INFORMATION: Xaa is 7-aminoheptanoic acid

<400> SEQUENCE: 21

His Glu Arg Met Ala Leu His Asn Leu Xaa
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (10)..(10)
<223> OTHER INFORMATION: Xaa is 7-aminoheptanoic acid

<400> SEQUENCE: 22

Asn Glu Arg Met Ala Leu His Asn Leu Xaa
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (11)..(11)
<223> OTHER INFORMATION: Xaa is bAla

<400> SEQUENCE: 23

Gly Thr Glu Arg Met Ala Leu His Asn Leu Xaa
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Dbu
<220> FEATURE:
<221> NAME/KEY: MISC_FEATURE
<222> LOCATION: (10)..(10)
<223> OTHER INFORMATION: Xaa is 7-aminoheptanoic acid

<400> SEQUENCE: 24

Xaa Glu Arg Met Ala Leu His Asn Leu Xaa
1               5                   10

<210> SEQ ID NO 25
<211> LENGTH: 10
<212> TYPE: PRT
<213> ORGANISM: Artificial Sequence -continued
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: Xaa is 7-aminoheptanoic acid

<400> SEQUENCE: 25

Leu His Asn Leu Xaa Gln Glu Arg Met Ala
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: Xaa is 7-aminoheptanoic acid

<400> SEQUENCE: 26

Leu His Asn Leu Xaa Ser Glu Arg Met Ala
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: Xaa is 7-aminoheptanoic acid

<400> SEQUENCE: 27

Leu His Asn Leu Xaa Val Glu Arg Met Ala
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: Xaa is 7-aminoheptanoic acid
<220> FEATURE:
<221> NAME/KEY: MISC_FEATURE
<222> LOCATION: (8)..(8)
<223> OTHER INFORMATION: Xaa is Orn

<400> SEQUENCE: 28

Leu His Asn Leu Xaa Thr Glu Xaa Met Ala
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: Xaa is 7-aminoheptanoic acid
<220> FEATURE:

```
<221> NAME/KEY: MISC_FEATURE
<222> LOCATION: (8)..(8)
<223> OTHER INFORMATION: Xaa is Dpr

<400> SEQUENCE: 29

Leu His Asn Leu Xaa Thr Glu Xaa Met Ala
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is 7-aminoheptanoic acid

<400> SEQUENCE: 30

Xaa Thr Glu Arg Met Arg Leu His Asn Leu
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is 7-aminoheptanoic acid
<220> FEATURE:
<221> NAME/KEY: MISC_FEATURE
<222> LOCATION: (6)..(6)
<223> OTHER INFORMATION: Xaa is Nva

<400> SEQUENCE: 31

Xaa Thr Glu Arg Met Xaa Leu His Asn Leu
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is 7-aminoheptanoic acid
<220> FEATURE:
<221> NAME/KEY: MISC_FEATURE
<222> LOCATION: (6)..(6)
<223> OTHER INFORMATION: Xaa is Dpr

<400> SEQUENCE: 32

Xaa Thr Glu Arg Met Xaa Leu His Asn Leu
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is 7-aminoheptanoic acid
```

```
<220> FEATURE:
<221> NAME/KEY: MISC_FEATURE
<222> LOCATION: (8)..(8)
<223> OTHER INFORMATION: Xaa is D-His

<400> SEQUENCE: 33

Xaa Thr Glu Arg Met Ala Leu Xaa Asn Leu
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is 7-aminoheptanoic acid
<220> FEATURE:
<221> NAME/KEY: MISC_FEATURE
<222> LOCATION: (8)..(8)
<223> OTHER INFORMATION: Xaa is Orn

<400> SEQUENCE: 34

Xaa Thr Glu Arg Met Ala Leu Xaa Asn Leu
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is 7-aminoheptanoic acid
<220> FEATURE:
<221> NAME/KEY: MISC_FEATURE
<222> LOCATION: (8)..(8)
<223> OTHER INFORMATION: Xaa is D-Asp

<400> SEQUENCE: 35

Xaa Thr Glu Arg Met Ala Leu Xaa Asn Leu
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is 7-aminoheptanoic acid
<220> FEATURE:
<221> NAME/KEY: MISC_FEATURE
<222> LOCATION: (7)..(7)
<223> OTHER INFORMATION: Xaa is 2-amino-4,4-dimethylpentanoic acid

<400> SEQUENCE: 36

Xaa Thr Glu Arg Met Ala Xaa His Asn Leu
1               5                   10

<210> SEQ ID NO 37
<211> LENGTH: 10
<212> TYPE: PRT
<213> ORGANISM: Artificial Sequence
<220> FEATURE:
```

```
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is 7-aminoheptanoic acid
<220> FEATURE:
<221> NAME/KEY: MISC_FEATURE
<222> LOCATION: (7)..(7)
<223> OTHER INFORMATION: Xaa is 1-aminocyclohexanecarboxylic acid

<400> SEQUENCE: 37

Xaa Thr Glu Arg Met Ala Xaa His Asn Leu
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is 7-aminoheptanoic acid

<400> SEQUENCE: 38

Xaa Thr Glu Arg Leu Ala Leu His Asn Leu
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is 7-aminoheptanoic acid
<220> FEATURE:
<221> NAME/KEY: MISC_FEATURE
<222> LOCATION: (5)..(5)
<223> OTHER INFORMATION: Xaa is cyclohexylglycine

<400> SEQUENCE: 39

Xaa Thr Glu Arg Xaa Ala Leu His Asn Leu
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is 7-aminoheptanoic acid

<400> SEQUENCE: 40

Xaa Thr Glu Arg Ala Ala Leu His Asn Leu
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
```

```
<222> LOCATION: (1)..(1)
<223> OTHER INFORMATION: Xaa is 7-aminoheptanoic acid

<400> SEQUENCE: 41

Xaa Thr Glu Arg Gln Ala Leu His Asn Leu
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is 7-aminoheptanoic acid
<220> FEATURE:
<221> NAME/KEY: MISC_FEATURE
<222> LOCATION: (5)..(5)
<223> OTHER INFORMATION: Xaa is Abu

<400> SEQUENCE: 42

Xaa Thr Glu Arg Xaa Ala Leu His Asn Leu
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is 7-aminoheptanoic acid
<220> FEATURE:
<221> NAME/KEY: MISC_FEATURE
<222> LOCATION: (5)..(5)
<223> OTHER INFORMATION: Xaa is Nle

<400> SEQUENCE: 43

Xaa Thr Glu Arg Xaa Ala Leu His Asn Leu
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is 7-aminoheptanoic acid
<220> FEATURE:
<221> NAME/KEY: MISC_FEATURE
<222> LOCATION: (5)..(5)
<223> OTHER INFORMATION: Xaa is 2-amino-4-methoxybutyric acid

<400> SEQUENCE: 44

Xaa Thr Glu Arg Xaa Ala Leu His Asn Leu
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Synthetic construct
<220> FEATURE:
```

```
<221> NAME/KEY: MISC_FEATURE
<222> LOCATION: (1)..(1)
<223> OTHER INFORMATION: Xaa is 7-aminoheptanoic acid
<220> FEATURE:
<221> NAME/KEY: MISC_FEATURE
<222> LOCATION: (5)..(5)
<223> OTHER INFORMATION: Xaa is 2-amino-3-methoxypropanoic acid

<400> SEQUENCE: 45

Xaa Thr Glu Arg Xaa Ala Leu His Asn Leu
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is 5-aminopentanoic acid

<400> SEQUENCE: 46

Xaa Thr Glu Arg Met Ala Leu His Asn Leu Gly
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is 10-aminodecanoic acid

<400> SEQUENCE: 47

Xaa Thr Glu Arg Met Ala Leu His Asn Leu
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is 4Abu

<400> SEQUENCE: 48

Xaa Thr Glu Arg Met Ala Leu His Asn Leu Gly
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is Dpr
<220> FEATURE:
<221> NAME/KEY: MISC_FEATURE
<222> LOCATION: (2)..(2)
<223> OTHER INFORMATION: Xaa is 4Abu
```

```
<400> SEQUENCE: 49

Xaa Xaa Thr Glu Arg Met Ala Leu His Asn Leu
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is 4Abu

<400> SEQUENCE: 50

Xaa Asn Thr Glu Arg Met Ala Leu His Asn Leu
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is bAla

<400> SEQUENCE: 51

Xaa Asn Thr Glu Arg Met Ala Leu His Asn Leu
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is bAla

<400> SEQUENCE: 52

Xaa Ala Thr Glu Arg Met Ala Leu His Asn Leu
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is 4Abu
<220> FEATURE:
<221> NAME/KEY: MISC_FEATURE
<222> LOCATION: (2)..(2)
<223> OTHER INFORMATION: Xaa is Aib

<400> SEQUENCE: 53

Xaa Xaa Thr Glu Arg Met Ala Leu His Asn Leu
1               5                   10
```

```
<210> SEQ ID NO 54
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is 4Abu
<220> FEATURE:
<221> NAME/KEY: MISC_FEATURE
<222> LOCATION: (2)..(2)
<223> OTHER INFORMATION: Xaa is 1-aminocyclopropanecarboxylic acid

<400> SEQUENCE: 54

Xaa Xaa Thr Glu Arg Met Ala Leu His Asn Leu
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is 7-aminoheptanoic acid

<400> SEQUENCE: 55

Xaa Thr Glu Arg Met Gln Leu His Asn Leu
1               5                   10

<210> SEQ ID NO 56
<211> LENGTH: 10
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is (2-(2-aminoethoxy)ethoxy)acetic acid

<400> SEQUENCE: 56

Xaa Thr Glu Arg Met Ala Leu His Asn Leu
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (5)..(5)
<223> OTHER INFORMATION: Xaa is 7-aminoheptanoic acid

<400> SEQUENCE: 57

Leu His Asn Leu Xaa Thr Glu Arg Met Ala
1               5                   10

<210> SEQ ID NO 58
<211> LENGTH: 10
<212> TYPE: PRT
<213> ORGANISM: Artificial Sequence
```

```
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala 10 by peptide bond
<220> FEATURE:
<221> NAME/KEY: MISC_FEATURE
<222> LOCATION: (5)..(5)
<223> OTHER INFORMATION: Xaa is 3-aminomethylphenylacetic acid

<400> SEQUENCE: 58

Leu His Asn Leu Xaa Thr Glu Arg Met Ala
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala 10 by peptide bond
<220> FEATURE:
<221> NAME/KEY: MISC_FEATURE
<222> LOCATION: (5)..(5)
<223> OTHER INFORMATION: Xaa is 4-aminomethylphenylacetic acid

<400> SEQUENCE: 59

Leu His Asn Leu Xaa Thr Glu Arg Met Ala
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (5)..(5)
<223> OTHER INFORMATION: Xaa is 2'-aminomethylbiphenyl-2-ylacetic acid

<400> SEQUENCE: 60

Leu His Asn Leu Xaa Thr Glu Arg Met Ala
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (5)..(5)
<223> OTHER INFORMATION: Xaa is 2-acetylamino-6-aminohexanoic acid

<400> SEQUENCE: 61

Leu His Asn Leu Xaa Thr Glu Arg Met Ala
1               5                   10

<210> SEQ ID NO 62
<211> LENGTH: 10
<212> TYPE: PRT
```

```
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala 10 by peptide bond
<220> FEATURE:
<221> NAME/KEY: MISC_FEATURE
<222> LOCATION: (5)..(5)
<223> OTHER INFORMATION: Xaa is 8-aminooctanoic acid

<400> SEQUENCE: 62

Leu His Asn Leu Xaa Thr Glu Arg Met Ala
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (5)..(5)
<223> OTHER INFORMATION: Xaa is 7-aminoheptanoic acid

<400> SEQUENCE: 63

Leu His Asn Leu Xaa Thr Glu Lys Met Ala
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (5)..(5)
<223> OTHER INFORMATION: Xaa is 7-aminoheptanoic acid
<220> FEATURE:
<221> NAME/KEY: MISC_FEATURE
<222> LOCATION: (6)..(6)
<223> OTHER INFORMATION: Xaa 1-aminocyclopropanecarboxylic acid

<400> SEQUENCE: 64

Leu His Asn Leu Xaa Xaa Glu Arg Met Ala
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (5)..(5)
<223> OTHER INFORMATION: Xaa is 7-aminoheptanoic acid
<220> FEATURE:
<221> NAME/KEY: MISC_FEATURE
<222> LOCATION: (6)..(6)
<223> OTHER INFORMATION: Xaa is 1-aminocyclopentanecarboxylic acid
```

```
<400> SEQUENCE: 65

Leu His Asn Leu Xaa Xaa Glu Arg Met Ala
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (5)..(5)
<223> OTHER INFORMATION: Xaa is 7-aminoheptanoic acid

<400> SEQUENCE: 66

Leu His Asn Leu Xaa Asp Glu Arg Met Ala
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (5)..(5)
<223> OTHER INFORMATION: Xaa is 6-aminohexanoic acid

<400> SEQUENCE: 67

Leu His Asn Leu Xaa Thr Glu Arg Met Ala
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (5)..(5)
<223> OTHER INFORMATION: Xaa is 7-aminoheptanoic acid

<400> SEQUENCE: 68

Leu His Asn Leu Xaa Leu Glu Arg Met Ala
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Xaa1 is linked to Ala10 by peptide bond
<220> FEATURE:
<221> NAME/KEY: MISC_FEATURE
<222> LOCATION: (1)..(1)
<223> OTHER INFORMATION: Xaa is Nle
```

```
<220> FEATURE:
<221> NAME/KEY: MISC_FEATURE
<222> LOCATION: (5)..(5)
<223> OTHER INFORMATION: Xaa is 7-aminoheptanoic acid

<400> SEQUENCE: 69

Xaa His Asn Leu Xaa Thr Glu Arg Met Ala
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Ile1 is linked to Ala10 by peptide bond
<220> FEATURE:
<221> NAME/KEY: MISC_FEATURE
<222> LOCATION: (5)..(5)
<223> OTHER INFORMATION: Xaa is 7-aminoheptanoic acid

<400> SEQUENCE: 70

Ile His Asn Leu Xaa Thr Glu Arg Met Ala
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (5)..(5)
<223> OTHER INFORMATION: Xaa is 9-aminononanoic acid

<400> SEQUENCE: 71

Leu His Asn Leu Xaa Thr Glu Arg Met Ala
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Xaa1 is linked to Ala10 by peptide bond
<220> FEATURE:
<221> NAME/KEY: MISC_FEATURE
<222> LOCATION: (1)..(1)
<223> OTHER INFORMATION: Xaa is cyclohexylalanine
<220> FEATURE:
<221> NAME/KEY: MISC_FEATURE
<222> LOCATION: (5)..(5)
<223> OTHER INFORMATION: Xaa is 7-aminoheptanoic acid

<400> SEQUENCE: 72

Xaa His Asn Leu Xaa Thr Glu Arg Met Ala
1               5                   10

<210> SEQ ID NO 73
<211> LENGTH: 10
<212> TYPE: PRT
<213> ORGANISM: Artificial Sequence
```

```
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (5)..(5)
<223> OTHER INFORMATION: Xaa is 7-aminoheptanoic acid
<220> FEATURE:
<221> NAME/KEY: MISC_FEATURE
<222> LOCATION: (9)..(9)
<223> OTHER INFORMATION: Xaa is cyclohexylalanine

<400> SEQUENCE: 73

Leu His Asn Leu Xaa Thr Glu Arg Xaa Ala
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (5)..(5)
<223> OTHER INFORMATION: Xaa is 7-aminoheptanoic acid

<400> SEQUENCE: 74

Leu His Asn Leu Xaa Thr Glu Arg Ile Ala
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Xaa1 is linked to Ala10 by peptide bond
<220> FEATURE:
<221> NAME/KEY: MISC_FEATURE
<222> LOCATION: (1)..(1)
<223> OTHER INFORMATION: Xaa is Nva
<220> FEATURE:
<221> NAME/KEY: MISC_FEATURE
<222> LOCATION: (5)..(5)
<223> OTHER INFORMATION: Xaa is 7-aminoheptanoic acid

<400> SEQUENCE: 75

Xaa His Asn Leu Xaa Thr Glu Arg Met Ala
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Xaa1 is linked to Ala10 by peptide bond
<220> FEATURE:
<221> NAME/KEY: MISC_FEATURE
<222> LOCATION: (1)..(1)
<223> OTHER INFORMATION: Xaa is cyclohexylglycine
<220> FEATURE:
<221> NAME/KEY: MISC_FEATURE
```

```
<222> LOCATION: (5)..(5)
<223> OTHER INFORMATION: Xaa is 7-aminoheptanoic acid

<400> SEQUENCE: 76

Xaa His Asn Leu Xaa Thr Glu Arg Met Ala
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (5)..(5)
<223> OTHER INFORMATION: Xaa is 7-aminoheptanoic acid

<400> SEQUENCE: 77

Leu His Asn Leu Xaa His Glu Arg Met Ala
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (5)..(5)
<223> OTHER INFORMATION: Xaa is 7-aminoheptanoic acid

<400> SEQUENCE: 78

Leu His Asn Leu Xaa Asn Glu Arg Met Ala
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala11 by peptide bond
<220> FEATURE:
<221> NAME/KEY: MISC_FEATURE
<222> LOCATION: (5)..(5)
<223> OTHER INFORMATION: Xaa is bAla

<400> SEQUENCE: 79

Leu His Asn Leu Xaa Gly Thr Glu Arg Met Ala
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
```

```
<221> NAME/KEY: MISC_FEATURE
<222> LOCATION: (5)..(5)
<223> OTHER INFORMATION: Xaa is 7-aminoheptanoic acid
<220> FEATURE:
<221> NAME/KEY: MISC_FEATURE
<222> LOCATION: (6)..(6)
<223> OTHER INFORMATION: Xaa is Dbu

<400> SEQUENCE: 80

Leu His Asn Leu Xaa Xaa Glu Arg Met Ala
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (5)..(5)
<223> OTHER INFORMATION: Xaa is 7-aminoheptanoic acid

<400> SEQUENCE: 81

Leu His Asn Leu Xaa Gln Glu Arg Met Ala
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (5)..(5)
<223> OTHER INFORMATION: Xaa is 7-aminoheptanoic acid

<400> SEQUENCE: 82

Leu His Asn Leu Xaa Ser Glu Arg Met Ala
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (5)..(5)
<223> OTHER INFORMATION: Xaa is 7-aminoheptanoic acid

<400> SEQUENCE: 83

Leu His Asn Leu Xaa Val Glu Arg Met Ala
1               5                   10

<210> SEQ ID NO 84
<211> LENGTH: 10
<212> TYPE: PRT
<213> ORGANISM: Artificial Sequence
<220> FEATURE:
```

```
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (5)..(5)
<223> OTHER INFORMATION: Xaa is 7-aminoheptanoic acid
<220> FEATURE:
<221> NAME/KEY: MISC_FEATURE
<222> LOCATION: (8)..(8)
<223> OTHER INFORMATION: Xaa is Orn

<400> SEQUENCE: 84

Leu His Asn Leu Xaa Thr Glu Xaa Met Ala
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (5)..(5)
<223> OTHER INFORMATION: Xaa is 7-aminoheptanoic acid
<220> FEATURE:
<221> NAME/KEY: MISC_FEATURE
<222> LOCATION: (8)..(8)
<223> OTHER INFORMATION: Xaa is Dpr

<400> SEQUENCE: 85

Leu His Asn Leu Xaa Thr Glu Xaa Met Ala
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Arg10 by peptide bond
<220> FEATURE:
<221> NAME/KEY: MISC_FEATURE
<222> LOCATION: (5)..(5)
<223> OTHER INFORMATION: Xaa is 7-aminoheptanoic acid

<400> SEQUENCE: 86

Leu His Asn Leu Xaa Thr Glu Arg Met Arg
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Xaa10 by peptide bond
<220> FEATURE:
<221> NAME/KEY: MISC_FEATURE
<222> LOCATION: (5)..(5)
<223> OTHER INFORMATION: Xaa is 7-aminoheptanoic acid
<220> FEATURE:
<221> NAME/KEY: MISC_FEATURE
<222> LOCATION: (10)..(10)
```

```
<223> OTHER INFORMATION: Xaa is Nva

<400> SEQUENCE: 87

Leu His Asn Leu Xaa Thr Glu Arg Met Xaa
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Xaa10 by peptide bond
<220> FEATURE:
<221> NAME/KEY: MISC_FEATURE
<222> LOCATION: (5)..(5)
<223> OTHER INFORMATION: Xaa is 7-aminoheptanoic acid
<220> FEATURE:
<221> NAME/KEY: MISC_FEATURE
<222> LOCATION: (10)..(10)
<223> OTHER INFORMATION: Xaa is Dpr

<400> SEQUENCE: 88

Leu His Asn Leu Xaa Thr Glu Arg Met Xaa
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (2)..(2)
<223> OTHER INFORMATION: Xaa is D-His
<220> FEATURE:
<221> NAME/KEY: MISC_FEATURE
<222> LOCATION: (5)..(5)
<223> OTHER INFORMATION: Xaa is 7-aminoheptanoic acid

<400> SEQUENCE: 89

Leu Xaa Asn Leu Xaa Thr Glu Arg Met Ala
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (2)..(2)
<223> OTHER INFORMATION: Xaa is Orn
<220> FEATURE:
<221> NAME/KEY: MISC_FEATURE
<222> LOCATION: (5)..(5)
<223> OTHER INFORMATION: Xaa is 7-aminoheptanoic acid

<400> SEQUENCE: 90

Leu Xaa Asn Leu Xaa Thr Glu Arg Met Ala
1               5                   10
```

```
<210> SEQ ID NO 91
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (2)..(2)
<223> OTHER INFORMATION: Xaa is D-Asp
<220> FEATURE:
<221> NAME/KEY: MISC_FEATURE
<222> LOCATION: (5)..(5)
<223> OTHER INFORMATION: Xaa is 7-aminoheptanoic acid

<400> SEQUENCE: 91

Leu Xaa Asn Leu Xaa Thr Glu Arg Met Ala
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Xaa1 is linked to Ala10 by peptide bond
<220> FEATURE:
<221> NAME/KEY: MISC_FEATURE
<222> LOCATION: (1)..(1)
<223> OTHER INFORMATION: Xaa is 2-amino-4,4-dimethylbutyric acid
<220> FEATURE:
<221> NAME/KEY: MISC_FEATURE
<222> LOCATION: (5)..(5)
<223> OTHER INFORMATION: Xaa is 7-aminoheptanoic acid

<400> SEQUENCE: 92

Xaa His Asn Leu Xaa Thr Glu Arg Met Ala
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Xaa1 is linked to Ala10 by peptide bond
<220> FEATURE:
<221> NAME/KEY: MISC_FEATURE
<222> LOCATION: (1)..(1)
<223> OTHER INFORMATION: Xaa is 1-aminocyclohexanecarboxylic acid
<220> FEATURE:
<221> NAME/KEY: MISC_FEATURE
<222> LOCATION: (5)..(5)
<223> OTHER INFORMATION: Xaa is 7-aminoheptanoic acid

<400> SEQUENCE: 93

Xaa His Asn Leu Xaa Thr Glu Arg Met Ala
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Synthetic cyclic construct
```

```
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (5)..(5)
<223> OTHER INFORMATION: Xaa is 7-aminoheptanoic acid

<400> SEQUENCE: 94

Leu His Asn Leu Xaa Thr Glu Arg Leu Ala
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (5)..(5)
<223> OTHER INFORMATION: Xaa is 7-aminoheptanoic acid
<220> FEATURE:
<221> NAME/KEY: MISC_FEATURE
<222> LOCATION: (9)..(9)
<223> OTHER INFORMATION: Xaa is cyclohexylglycine

<400> SEQUENCE: 95

Leu His Asn Leu Xaa Thr Glu Arg Xaa Ala
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (5)..(5)
<223> OTHER INFORMATION: Xaa is 7-aminoheptanoic acid

<400> SEQUENCE: 96

Leu His Asn Leu Xaa Thr Glu Arg Ala Ala
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (5)..(5)
<223> OTHER INFORMATION: Xaa is 7-aminoheptanoic acid

<400> SEQUENCE: 97

Leu His Asn Leu Xaa Thr Glu Arg Gln Ala
1               5                   10

<210> SEQ ID NO 98
```

```
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (5)..(5)
<223> OTHER INFORMATION: Xaa is 7-aminoheptanoic acid
<220> FEATURE:
<221> NAME/KEY: MISC_FEATURE
<222> LOCATION: (9)..(9)
<223> OTHER INFORMATION: Xaa is Abu

<400> SEQUENCE: 98

Leu His Asn Leu Xaa Thr Glu Arg Xaa Ala
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (5)..(5)
<223> OTHER INFORMATION: Xaa is 7-aminoheptanoic acid
<220> FEATURE:
<221> NAME/KEY: MISC_FEATURE
<222> LOCATION: (9)..(9)
<223> OTHER INFORMATION: Xaa is Nle

<400> SEQUENCE: 99

Leu His Asn Leu Xaa Thr Glu Arg Xaa Ala
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (5)..(5)
<223> OTHER INFORMATION: Xaa is 7-aminoheptanoic acid
<220> FEATURE:
<221> NAME/KEY: MISC_FEATURE
<222> LOCATION: (9)..(9)
<223> OTHER INFORMATION: Xaa is 2-amino-4-methoxybutyric acid

<400> SEQUENCE: 100

Leu His Asn Leu Xaa Thr Glu Arg Xaa Ala
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Synthetic cyclic construct
```

```
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (5)..(5)
<223> OTHER INFORMATION: Xaa is 7-aminoheptanoic acid
<220> FEATURE:
<221> NAME/KEY: MISC_FEATURE
<222> LOCATION: (9)..(9)
<223> OTHER INFORMATION: Xaa is 2-amino-3-methoxypropionic acid

<400> SEQUENCE: 101

Leu His Asn Leu Xaa Thr Glu Arg Xaa Ala
1               5                   10

<210> SEQ ID NO 102
<211> LENGTH: 11
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala11 by peptide bond
<220> FEATURE:
<221> NAME/KEY: MISC_FEATURE
<222> LOCATION: (6)..(6)
<223> OTHER INFORMATION: Xaa is 5-aminopentanoic acid

<400> SEQUENCE: 102

Leu His Asn Leu Gly Xaa Thr Glu Arg Met Ala
1               5                   10

<210> SEQ ID NO 103
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (5)..(5)
<223> OTHER INFORMATION: Xaa is 10-aminodecanoic acid

<400> SEQUENCE: 103

Leu His Asn Leu Xaa Thr Glu Arg Met Ala
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala11 by peptide bond
<220> FEATURE:
<221> NAME/KEY: MISC_FEATURE
<222> LOCATION: (6)..(6)
<223> OTHER INFORMATION: Xaa is 4Abu

<400> SEQUENCE: 104

Leu His Asn Leu Gly Xaa Thr Glu Arg Met Ala
1               5                   10
```

```
<210> SEQ ID NO 105
<211> LENGTH: 11
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala11 by peptide bond
<220> FEATURE:
<221> NAME/KEY: MISC_FEATURE
<222> LOCATION: (5)..(5)
<223> OTHER INFORMATION: Xaa is Dpr
<220> FEATURE:
<221> NAME/KEY: MISC_FEATURE
<222> LOCATION: (6)..(6)
<223> OTHER INFORMATION: Xaa is 4Abu

<400> SEQUENCE: 105

Leu His Asn Leu Xaa Xaa Thr Glu Arg Met Ala
1               5                   10

<210> SEQ ID NO 106
<211> LENGTH: 11
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala11 by peptide bond
<220> FEATURE:
<221> NAME/KEY: MISC_FEATURE
<222> LOCATION: (5)..(5)
<223> OTHER INFORMATION: Xaa is 4Abu

<400> SEQUENCE: 106

Leu His Asn Leu Xaa Asn Thr Glu Arg Met Ala
1               5                   10

<210> SEQ ID NO 107
<211> LENGTH: 11
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala11 by peptide bond
<220> FEATURE:
<221> NAME/KEY: MISC_FEATURE
<222> LOCATION: (5)..(5)
<223> OTHER INFORMATION: Xaa is bAla

<400> SEQUENCE: 107

Leu His Asn Leu Xaa Asn Thr Glu Arg Met Ala
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala11 by peptide bond
<220> FEATURE:
<221> NAME/KEY: MISC_FEATURE
```

```
<222> LOCATION: (5)..(5)
<223> OTHER INFORMATION: Xaa is bAla

<400> SEQUENCE: 108

Leu His Asn Leu Xaa Ala Thr Glu Arg Met Ala
1               5                   10

<210> SEQ ID NO 109
<211> LENGTH: 11
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala11 by peptide bond
<220> FEATURE:
<221> NAME/KEY: MISC_FEATURE
<222> LOCATION: (5)..(5)
<223> OTHER INFORMATION: Xaa is 4Abu
<220> FEATURE:
<221> NAME/KEY: MISC_FEATURE
<222> LOCATION: (6)..(6)
<223> OTHER INFORMATION: Xaa is Aib

<400> SEQUENCE: 109

Leu His Asn Leu Xaa Xaa Thr Glu Arg Met Ala
1               5                   10

<210> SEQ ID NO 110
<211> LENGTH: 11
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala11 by peptide bond
<220> FEATURE:
<221> NAME/KEY: MISC_FEATURE
<222> LOCATION: (5)..(5)
<223> OTHER INFORMATION: Xaa is 4Abu
<220> FEATURE:
<221> NAME/KEY: MISC_FEATURE
<222> LOCATION: (6)..(6)
<223> OTHER INFORMATION: Xaa is 1-aminocyclopropanecarboxylic acid

<400> SEQUENCE: 110

Leu His Asn Leu Xaa Xaa Thr Glu Arg Met Ala
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Gln10 by peptide bond
<220> FEATURE:
<221> NAME/KEY: MISC_FEATURE
<222> LOCATION: (5)..(5)
<223> OTHER INFORMATION: Xaa is 7-aminoheptanoic acid

<400> SEQUENCE: 111

Leu His Asn Leu Xaa Thr Glu Arg Met Gln
1               5                   10
```

```
<210> SEQ ID NO 112
<211> LENGTH: 10
<212> TYPE: PRT
<213> ORGANISM: Artificial sequence
<220> FEATURE:
<223> OTHER INFORMATION: Synthetic cyclic construct
<220> FEATURE:
<221> NAME/KEY: MISC_FEATURE
<223> OTHER INFORMATION: Leu1 is linked to Ala10 by peptide bond
<220> FEATURE:
<221> NAME/KEY: MISC_FEATURE
<222> LOCATION: (5)..(5)
<223> OTHER INFORMATION: Xaa is (2-(2-aminoethoxy)ethoxy)acetic acid

<400> SEQUENCE: 112

Leu His Asn Leu Xaa Thr Glu Arg Met Ala
1               5                   10

<210> SEQ ID NO 113
<211> LENGTH: 10
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (10)..(10)
<223> OTHER INFORMATION: Xaa is 7-aminoheptanoic acid

<400> SEQUENCE: 113

Thr Glu Arg Met Ala Leu His Asn Leu Xaa
1               5                   10

<210> SEQ ID NO 114
<211> LENGTH: 14
<212> TYPE: PRT
<213> ORGANISM: Artificial sequence
<220> FEATURE:
<223> OTHER INFORMATION: Synthetic cyclic construct
<220> FEATURE:
<221> NAME/KEY: MISC_FEATURE
<223> OTHER INFORMATION: Cys2 is linked to Cys12 by disulfide bond
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (14)..(14)
<223> OTHER INFORMATION: AMIDATION
<300> PUBLICATION INFORMATION:
<301> AUTHORS: S.A. Benard et al.
<302> TITLE: Identification of Peptide Antagonists to Glycoprotein
      Ibalpha That Selectively Inhibit von Willebrand Factor Dependent
      Platelet Aggregation
<303> JOURNAL: Biochemistry
<304> VOLUME: 47
<306> PAGES: 4674-4682
<307> DATE: 2008

<400> SEQUENCE: 114

Ala Cys Thr Glu Arg Met Ala Leu His Asn Leu Cys Gly Gly
1               5                   10
```

CYCLIC PEPTIDES, THEIR PREPARATION AND THEIR USE AS INHIBITORS OF THE PLATELET ADHESION

The present invention relates to compounds of the formula I,

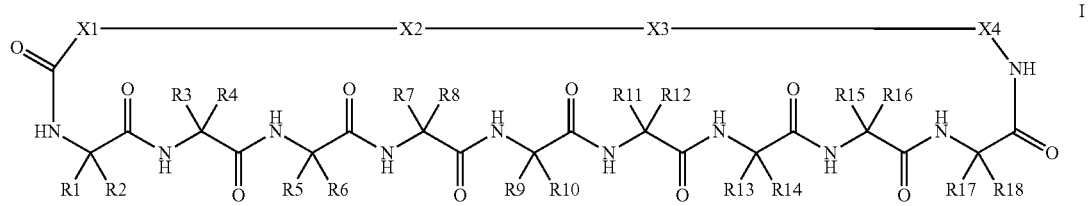

in which R1, R2, R3, R4, R5, R6, R7, R8, R9, R10, R11, R12, R13, R14, R15, R16, R17, R18, X1, X2, X3 and X4 have the meanings indicated below.

The compounds of the formula I are valuable pharmacologically active compounds. They are reversible inhibitors of the interaction between the plasma protein von Willebrand factor (vWF) and the blood platelet receptor glycoprotein Ib-IX-V complex (GPIb). This interaction causes primary adhesion of platelets to the injured subendothelial matrix and consequently platelet aggregation and thrombus formation. Inhibitors of this interaction exhibit an antithrombotic effect and are suitable, for example, for the therapy and prophylaxis of athero-thrombotic diseases, such as prevention or secondary prevention of myocardial infarction, unstable angina, acute coronary syndromes, coronary artery disease, reocclusion following coronary thrombolysis, occlusion during thromboplasty and coronary restenosis, stroke, transient ischemic attacks, pulmonary embolism, left ventricular dysfunction, clinical vascular complications in patients with cardiovascular and cerebrovascular disease, atherosclerosis, as comedication to vascular interventional strategies, and others.

They can in general be applied in conditions in which the interaction between GPIb and vWF leads to undesired physiological impact, or for the cure or prevention of which an inhibition of the interaction between GPIb and vWF is intended. The invention furthermore relates to processes for the preparation of compounds of the formula I, their use, in particular as pharmaceuticals or active ingredients in medicaments, and pharmaceutical compositions comprising them.

Platelet adhesion and thrombus formation are complex processes crucial to haemostasis. The formation of a blood clot is normally the result of tissue injury which initiates the platelet adhesion/aggregation and the coagulation cascade and has the effect of slowing or preventing blood flow in wound healing. However, in certain disease states the formation of blood clots within the circulatory system reaches an undesired extent and is itself the source of morbidity potentially leading to pathological consequences. Circulating platelets become adherent and form an occlusive thrombus either by exposure to atherosclerotic lesions following plaque rupture or in response to pathological shear stress.

Many adhesive proteins and various receptors are involved in this complex progress. An important adhesive plasma protein is vWF, a multimeric glycoprotein with a mature subunit of 2050 amino acids. Two platelet membrane glycoprotein receptors for vWF have been identified. Unactivated platelets bind vWF through the platelet GPIb complex. This interaction is induced physiologically by high shear or by binding of vWF to any surface. Subsequently vWF changes the conformation and presents the A1 binding domain in such a way that interaction becomes possible. After activation, platelets express a second binding site for vWF, the GPIIb-IIIc complex, which is also a binding site for fibrinogen. Platelet activation induces amplification mechanisms which finally lead to a firm platelet attachment.

The essential role of GPIb in platelet adhesion was established with the use of antibodies and by observations on a genetic defect, the Bernard-Soulier syndrome, in which GPIb is absent from platelets. Platelets from Bernard-Soulier patients poorly adhere and moderately aggregate in response to vWF. Also a lot of snake venom proteins are reported which modulate the interaction ob GPIb and vWF.

Specific inhibition of the interaction of GPIb to vWF using monoclonal antibodies or snake venom proteins is an effective means of controlling thrombus formation caused by arterial injury or thrombotic complications. Also for certain small peptides it has been described that they are efficient inhibitors of the GPIb-vWF interaction (Benard, S. A., Smith, T. M., Cunningham, K., Jacob, J., DeSilva, T., Lin, L., Shaw, G. D., Kriz, R., Kelleher, K. S., Biochemistry 47 (16) 4674, 2008). Besides some other compounds, in the article by Benard et al. an optimized synthetic peptide inhibiting GPIb-vWF interaction has been described, which has been designated as OS-1. The characterized peptide OS-1 has the amino acid sequence acetyl-Ala-Cys-Thr-Glu-Arg-Met-Ala-Leu-His-Asn-Leu-Cys-Gly-Gly-$NH_2$ (SEQ ID NO: 114), in which the two cysteine units are linked to each other by formation of a disulfide bond, and thus is a cyclic peptide carrying the exocyclic amino acid and dipeptide moieties acetyl-Ala and Gly-Gly-$NH_2$ with respect to which it is indicated in the article of Benard et al. that they may impact binding affinity. Two cysteine units in the respective positions of the peptide giving rise to a disulfide moiety are present also in the other compounds described by Benard et al. In the article by McEwan, P. A., Andrews, R. K., Emsley, J., Blood 114 (23) 4883, 2009, the structure of a complex of GPIba and OS-1 is described and it is outlined that the disulfide moiety interacts with GPIb, and thus is of relevance for the activity of the compound. In the articles by Benard et al. and McEwan et al. there is no suggestion that compounds which lack the disulfide moiety, or the two cysteine units, and contain instead thereof a structural moiety of completely different nature, and may thus also avoid disadvantages associated with the disulfide moiety such as its susceptibility to cleavage and thereby loss of activity of the compound, and/or which lack the exocyclic amino acid and dipeptide moieties, may also be efficient inhibitors of the GPIb-vWF interaction.

Further, there is experimental evidence suggesting that inhibition of the GPIb-vWF interaction inhibits thrombus formation with a wider safety window than abciximab, an antibody for GPIIb-IIIa which has already been launched (Kageyama, S., Yamamoto, H., Nakazawa, H., Yoshimoto, R., Thrombosis Research 101 (5) (2001) 395-404). However there is still no drug available for patients to inhibit the GPIb-vWF interaction and thus inhibit thrombus formation.

Therefore, since there continues to be a need for safe and effective therapeutic antithrombotic agents to limit or prevent thrombus formation, it is most desirable to develop agents that inhibit an early step in thrombogenesis like inhibition of the GPIb-vWF interaction (cf. Firbas, C., Siller-Matula, J. M., Jilma, B., Expert Review of Cardiovascular Therapy 8 (12) 1689, 2010; Kleinschnitz, C., Pozgajova, M., Pham, M., Bendszus, M., Nieswandt, B., Stoll, G., Circulation 115 (17) 2323, 2007; or Stoll, G., Kleinschnitz, C., Nieswandt, B., Hämostaseologie 30 (3) 136, 2010, for example). A specific inhibitor for the GPIb-vWF interaction, which preferably has further favorable properties such as a suitable stability and duration of action, would have substantial practical value in the practice of medicine. The present invention satisfies the above needs by providing the novel compounds of the formula I which inhibit GPIb-vWF interaction.

In one embodiment, the present invention relates to compounds of the formula I,

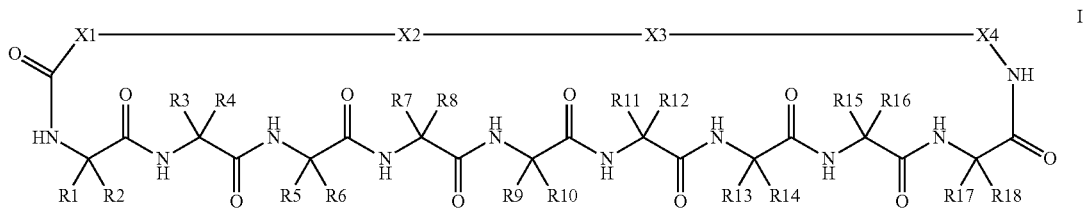

wherein
X1 is —($C_1$-$C_8$)-alkyl-, wherein alkyl is unsubstituted or monosubstituted or disubstituted by one or more substituents independently selected from —NH—C(O)—($C_1$-$C_6$)-alkyl, —($C_1$-$C_6$)-alkyl-$NH_2$, —($C_1$-$C_6$)-alkyl-C(O)—$NH_2$, —($C_1$-$C_6$)-alkyl-C(O)—OH and —($C_1$-$C_6$)-alkyl,
or
X1 is

wherein n is 1, 2, 3, 4 or 5;
X2 is a covalent bond, —($C_1$-$C_8$)-alkyl- or monocyclic or bicyclic 6-membered to 14-membered aryl, wherein aryl is unsubstituted or monosubstituted, disubstituted, trisubstituted or tetrasubstituted independently of one another by R19;
X3 is a covalent bond, —($C_1$-$C_8$)-alkyl- or monocyclic or bicyclic 6-membered to 14-membered aryl, wherein aryl is unsubstituted or monosubstituted, disubstituted, trisubstituted or tetrasubstituted independently of one another by R19;
or
X2-X3 is —NH—C(O)—, —C(O)—NH—, —($C_0$-$C_8$)-alkyl-O—($C_0$-$C_8$)-alkyl- or —($C_0$-$C_8$)-alkyl-S—($C_0$-$C_8$)-alkyl-;
X4 is —($C_1$-$C_8$)-alkyl-, wherein alkyl is unsubstituted or monosubstituted or disubstituted by one or more substituents independently selected from —NH—C(O)—($C_1$-$C_6$)-alkyl, —($C_1$-$C_6$)-alkyl-$NH_2$, —($C_1$-$C_6$)-alkyl-C(O)—$NH_2$, —($C_1$-$C_6$)-alkyl-C(O)—OH and —($C_1$-$C_6$)-alkyl,
or
X4 is

wherein m is 1, 2, 3, 4 or 5;
or
X1-X2-X3-X4 is —($C_1$-$C_8$)-alkyl-O—($C_2$-$C_8$)-alkyl-O—($C_2$-$C_8$)-alkyl-;
R1, R2, R3, R4, R5, R6, R7, R8, R9, R10, R11, R12, R13, R14, R15, R16, R17 and R18
are independently of one another selected from hydrogen, —($C_1$-$C_{10}$)-alkyl, —($C_1$-$C_8$)-alkyl-C(O)—N(R20)-R21, —($C_1$-$C_4$)-alkyl-C(O)—O—R22, —($C_1$-$C_6$)-alkyl-O—R23, —($C_1$-$C_6$)-alkyl-S—R24, —($C_1$-$C_6$)-alkyl-$NH_2$, —($C_1$-$C_6$)-alkyl-C(=NH)—$NH_2$, —($C_1$-$C_6$)-alkyl-NH—C(=NH)—$NH_2$, —($C_0$-$C_4$)-alkyl-($C_3$-$C_8$)-cycloalkyl, —($C_0$-$C_4$)-alkyl-($C_6$-$C_{14}$)-aryl and —($C_0$-$C_4$)-alkyl-heterocyclyl, wherein alkyl in —($C_1$-$C_{10}$)-alkyl is unsubstituted or monosubstituted, disubstituted or trisubstituted independently of one another by halogen, and wherein aryl in —($C_0$-$C_4$)-alkyl-($C_6$-$C_{14}$)-aryl is unsubstituted or monosubstituted, disubstituted or trisubstituted independently of one another by R19, and wherein heterocyclyl in —($C_0$-$C_4$)-alkyl-heterocyclyl is monocyclic or bicyclic and contains 3 to 15 ring carbon atoms, wherein one or more of the ring carbon atoms are replaced by 1, 2, 3 or 4 heteroatoms chosen from nitrogen, sulfur and oxygen, and wherein said heterocyclyl is unsubstituted or monosubstituted, disubstituted or trisubstituted independently of one another by R19;
or R1 and R2 and/or R3 and R4 and/or R5 and R6 and/or R7 and R8 and/or R9 and R10 and/or R11 and R12 and/or R13 and R14 and/or R15 and R16 and/or R17 and R18 form together with the atoms to which they are attached, independently of each other, a ring selected from cyclopropane, cyclobutane, cyclopentane, cyclohexane and cycloheptane;
R19 is halogen, amino, ($C_1$-$C_4$)-alkylamino, di(($C_1$-$C_4$)-alkyl)amino, cyano, —($C_1$-$C_4$)-alkoxy, hydroxyl or —($C_1$-$C_6$)-alkyl;
R20, R21, R22, R23 and R24
are independently of one another selected from hydrogen and —($C_1$-$C_6$)-alkyl;
and their pharmaceutically acceptable salts.

In another embodiment, the invention is directed to compounds of the formula I, wherein
X1 is —($C_1$-$C_8$)-alkyl-, wherein alkyl is unsubstituted or monosubstituted or disubstituted by one or more substituents independently selected from —NH—C(O)—($C_1$-$C_6$)- alkyl, —($C_1$-$C_6$)-alkyl-$NH_2$, —($C_1$-$C_6$)-alkyl-C(O)—$NH_2$, —($C_1$-$C_6$)-alkyl-C(O)—OH and —($C_1$-$C_6$)-alkyl,
or
X1 is

wherein n is 1, 2, 3, 4 or 5;

X2 is a covalent bond, —($C_1$-$C_8$)-alkyl- or monocyclic 6-membered aryl, wherein aryl is unsubstituted or monosubstituted, disubstituted, trisubstituted or tetrasubstituted independently of one another by R19;

X3 is a covalent bond, —($C_1$-$C_8$)-alkyl- or monocyclic 6-membered aryl, wherein aryl is unsubstituted or monosubstituted, disubstituted, trisubstituted or tetrasubstituted independently of one another by R19;

or

X2-X3 is —NH—C(O)—, —C(O)—NH—, —($C_0$-$C_8$)-alkyl-O—($C_0$-$C_8$)-alkyl- or —($C_0$-$C_8$)-alkyl-S—($C_0$-$C_8$)-alkyl-;

X4 is —($C_1$-$C_8$)-alkyl-, wherein alkyl is unsubstituted or monosubstituted or disubstituted by one or more substituents independently selected from —NH—C(O)—($C_1$-$C_6$)-alkyl, —($C_1$-$C_6$)-alkyl-$NH_2$, —($C_1$-$C_6$)-alkyl-C(O)—$NH_2$, —($C_1$-$C_6$)-alkyl-C(O)—OH and —($C_1$-$C_6$)-alkyl,
or
X4 is

wherein m is 1, 2, 3, 4 or 5;
or

X1-X2-X3-X4 is —($C_1$-$C_8$)-alkyl-O—($C_2$-$C_8$)-alkyl-O—($C_2$-$C_8$)-alkyl-;

R1 and R2 are independently of one another selected from hydrogen, —($C_1$-$C_{10}$)-alkyl, —($C_1$-$C_8$)-alkyl-C(O)—N(R20)-R21, —($C_1$-$C_4$)-alkyl-C(O)—O—R22, —($C_1$-$C_6$)-alkyl-OH, —($C_1$-$C_6$)-alkyl-$NH_2$, —($C_1$-$C_6$)-alkyl-C(=NH)—$NH_2$, —($C_1$-$C_6$)-alkyl-NH—C(=NH)—$NH_2$ and —($C_0$-$C_4$)-alkyl-heterocyclyl, wherein alkyl in —($C_1$-$C_{10}$)-alkyl is unsubstituted or monosubstituted disubstituted or trisubstituted independently of one another by halogen, and wherein heterocyclyl in —($C_0$-$C_4$)-alkyl-heterocyclyl is monocyclic or bicyclic and contains 3 to 15 ring carbon atoms, wherein one or more of the ring carbon atoms are replaced by 1, 2, 3 or 4 heteroatoms chosen from nitrogen, sulfur and oxygen, and wherein said heterocyclyl is unsubstituted or monosubstituted, disubstituted or trisubstituted independently of one another by R19,
or R1 and R2 form together with the atom to which they are attached, a ring selected from cyclopropane and cyclopentane;

R3 and R4 are independently of one another selected from hydrogen, —($C_1$-$C_{10}$)-alkyl and —($C_1$-$C_4$)-alkyl-C(O)—O—R22, wherein alkyl in —($C_1$-$C_{10}$)-alkyl is unsubstituted or monosubstituted, disubstituted or trisubstituted independently of one another by halogen;

R5 and R6 are independently of one another selected from hydrogen, —($C_1$-$C_6$)-alkyl-$NH_2$, —($C_1$-$C_6$)-alkyl-C(=NH)—$NH_2$, —($C_1$-$C_6$)-alkyl-NH—C(=NH)—$NH_2$ and —($C_0$-$C_4$)-alkyl-heterocyclyl, wherein heterocyclyl in —($C_0$-$C_4$)-alkyl-heterocyclyl is monocyclic or bicyclic and contains 3 to 15 ring carbon atoms, wherein one or more of the ring carbon atoms are replaced by 1, 2, 3 or 4 heteroatoms chosen from nitrogen, sulfur or oxygen, and wherein said heterocyclyl is unsubstituted or monosubstituted, disubstituted or trisubstituted independently of one another by R19;

R7 and R8 are independently of one another selected from hydrogen, —($C_1$-$C_{10}$)-alkyl, —($C_1$-$C_6$)-alkyl-O—R23, —($C_0$-$C_4$)-alkyl-($C_3$-$C_8$)-cycloalkyl and —($C_0$-$C_4$)-alkyl-($C_6$-$C_{14}$)-aryl, wherein alkyl in —($C_1$-$C_{10}$)-alkyl is unsubstituted or monosubstituted, disubstituted or trisubstituted independently of one another by halogen, and wherein aryl in —($C_0$-$C_4$)-alkyl-($C_6$-$C_{14}$)-aryl is unsubstituted or monosubstituted, disubstituted or trisubstituted independently of one another by R19;

R9 and R10 are independently of one another selected from hydrogen, —($C_1$-$C_{10}$)-alkyl, —($C_1$-$C_6$)-alkyl-C(O)—N(R20)-R21, —($C_1$-$C_4$)-alkyl-C(O)—O—R22, —($C_1$-$C_6$)-alkyl-$NH_2$ and —($C_0$-$C_4$)-alkyl-($C_3$-$C_8$)-cycloalkyl, wherein alkyl in —($C_1$-$C_{10}$)-alkyl is unsubstituted or monosubstituted, disubstituted or trisubstituted independently of one another by halogen;

R11, R12, R17 and R18
are independently of one another selected from hydrogen, —($C_1$-$C_{10}$)-alkyl, —($C_1$-$C_6$)-alkyl-O—R23, —($C_1$-$C_6$)-alkyl-S—R24, —($C_0$-$C_4$)-alkyl-($C_3$-$C_8$)-cycloalkyl and —($C_0$-$C_4$)-alkyl-($C_6$-$C_{14}$)-aryl, wherein alkyl in —($C_1$-$C_{10}$)-alkyl is unsubstituted or monosubstituted, disubstituted or trisubstituted independently of one another by halogen, and wherein aryl in —($C_0$-$C_4$)-alkyl-($C_6$-$C_{14}$)-aryl is unsubstituted or monosubstituted, disubstituted or trisubstituted independently of one another by R19,
or R11 and R12 and/or R17 and R18 form together with the atoms to which they are attached, independently of each other, a ring selected from cyclopropane, cyclobutane, cyclopentane, cyclohexane and cycloheptane;

R13, R14, R15 and R16
are independently of one another selected from hydrogen, —($C_1$-$C_{10}$)-alkyl, —($C_1$-$C_6$)-alkyl-C(O)—N(R20)-R21, —($C_1$-$C_4$)-alkyl-C(O)—O—R22, —($C_1$-$C_6$)-alkyl-$NH_2$ and —($C_0$-$C_4$)-alkyl-heterocyclyl, wherein alkyl in —($C_1$-$C_{10}$)-alkyl is unsubstituted or monosubstituted, disubstituted or trisubstituted independently of one another by halogen, and wherein heterocyclyl in —($C_0$-$C_4$)-alkyl-heterocyclyl is monocyclic or bicyclic and contains 3 to 15 ring carbon atoms, wherein one or more of the ring carbon atoms are replaced by 1, 2, 3 or 4 heteroatoms chosen from nitrogen, sulfur and oxygen, and wherein said heterocyclyl is unsubstituted or monosubstituted, disubstituted or trisubstituted independently of one another by R19;

R19 is halogen, amino, cyano, —($C_1$-$C_4$)-alkoxy, hydroxyl or —($C_1$-$C_6$)-alkyl;

R20, R21, R22, R23 and R24
are independently of one another selected from hydrogen and —($C_1$-$C_6$)-alkyl;
and their pharmaceutically acceptable salts.

In another embodiment, the invention is directed to compounds of the formula I, wherein
X1 is —($C_1$-$C_8$)-alkyl-, wherein alkyl is unsubstituted or monosubstituted or disubstituted by one or more substituents independently selected from —NH—C(O)—($C_1$-$C_6$)-alkyl, —($C_1$-$C_6$)-alkyl-$NH_2$, —($C_1$-$C_6$)-alkyl-C(O)—$NH_2$, —($C_1$-$C_6$)-alkyl-C(O)—OH and —($C_1$-$C_6$)-alkyl,
or
X1 is

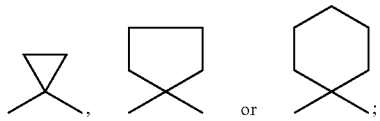

X2 is a covalent bond, —($C_1$-$C_8$)-alkyl- or monocyclic 6-membered aryl, wherein aryl is unsubstituted;
X3 is a covalent bond, —($C_1$-$C_8$)-alkyl- or monocyclic 6-membered aryl, wherein aryl is unsubstituted;
or
X2-X3 is —NH—C(O)—, —C(O)—NH—, —($C_0$-$C_8$)-alkyl-O—($C_0$-$C_8$)-alkyl- or —($C_0$-$C_8$)-alkyl-S—($C_0$-$C_8$)-alkyl-;
X4 is —($C_1$-$C_8$)-alkyl-, wherein alkyl is unsubstituted or monosubstituted or disubstituted by one or more substituents independently selected from —NH—C(O)—($C_1$-$C_6$)-alkyl, —($C_1$-$C_6$)-alkyl-$NH_2$, —($C_1$-$C_6$)-alkyl-C(O)—$NH_2$, —($C_1$-$C_6$)-alkyl-C(O)—OH and —($C_1$-$C_6$)-alkyl,
or
X4 is

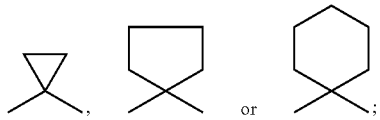

or
X1-X2-X3-X4 is —($C_1$-$C_8$)-alkyl-O—($C_2$-$C_8$)-alkyl-O—($C_2$-$C_8$)-alkyl-;
R1 and R2 are independently of one another selected from hydrogen, —($C_1$-$C_{10}$)-alkyl, —($C_1$-$C_6$)-alkyl-C(O)—N(R20)-R21, —($C_1$-$C_4$)-alkyl-C(O)—O—R22, —($C_1$-$C_6$)-alkyl, —($C_1$-$C_6$)-alkyl-$NH_2$, —($C_1$-$C_6$)-alkyl-C(=NH)—$NH_2$, —($C_1$-$C_6$)-alkyl-NH—C(=NH)—$NH_2$ and —($C_0$-$C_4$)-alkyl-heterocyclyl, wherein alkyl in —($C_1$-$C_{10}$)-alkyl is unsubstituted or monosubstituted, disubstituted or trisubstituted independently of one another by halogen, and wherein heterocyclyl in —($C_0$-$C_4$)-alkyl-heterocyclyl is monocyclic or bicyclic and contains 3 to 15 ring carbon atoms, wherein one or more of the ring carbon atoms are replaced by 1, 2, 3 or 4 heteroatoms chosen from nitrogen, sulfur and oxygen, and wherein said heterocyclyl is unsubstituted or monosubstituted, disubstituted or trisubstituted independently of one another by R19,
or
R1 and R2 form together with the atom to which they are attached, a ring selected from cyclopropane and cyclopentane;
R3 and R4 are independently of one another selected from hydrogen, —($C_1$-$C_{10}$)-alkyl and —($C_1$-$C_4$)-alkyl-C(O)—OH, wherein alkyl in —($C_1$-$C_{10}$)-alkyl is unsubstituted or monosubstituted, disubstituted or trisubstituted independently of one another by halogen;
R5 and R6 are independently of one another selected from hydrogen, —($C_1$-$C_6$)-alkyl-$NH_2$, —($C_1$-$C_6$)-alkyl-NH—C(=NH)—$NH_2$,

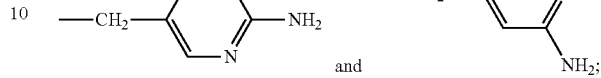

R7 and R8 are independently of one another selected from hydrogen, —($C_1$-$C_{10}$)-alkyl, —($C_1$-$C_6$)-alkyl-O—$CH_3$, —($C_0$-$C_4$)-alkyl-($C_3$-$C_8$)-cycloalkyl and —($C_0$-$C_4$)-alkyl-($C_6$-$C_{14}$)-aryl, wherein alkyl in —($C_1$-$C_{10}$)-alkyl is unsubstituted or monosubstituted, disubstituted or trisubstituted independently of one another by halogen, and wherein aryl in —($C_0$-$C_4$)-alkyl-($C_6$-$C_{14}$)-aryl is unsubstituted or monosubstituted, disubstituted or trisubstituted independently of one another by R19;
R9 and R10 are independently of one another selected from hydrogen, —($C_1$-$C_{10}$)-alkyl, —($C_1$-$C_6$)-alkyl-C(O)—$NH_2$, —($C_1$-$C_4$)-alkyl-C(O)—OH, —($C_1$-$C_6$)-alkyl-O—$CH_3$, —($C_1$-$C_6$)-alkyl-S—$CH_3$, —($C_1$-$C_6$)-alkyl-$NH_2$ and —($C_0$-$C_4$)-alkyl-($C_3$-$C_8$)-cycloalkyl, wherein alkyl in —($C_1$-$C_{10}$)-alkyl is unsubstituted or monosubstituted, disubstituted or trisubstituted independently of one another by halogen;
R11 and R12
are independently of one another selected from hydrogen, —($C_1$-$C_{10}$)-alkyl, —($C_0$-$C_4$)-alkyl-($C_3$-$C_8$)-cycloalkyl and —($C_0$-$C_4$)-alkyl-($C_6$-$C_{14}$)-aryl, wherein aryl is unsubstituted, and wherein alkyl in —($C_1$-$C_{10}$)-alkyl is unsubstituted or monosubstituted, disubstituted or trisubstituted independently of one another by halogen,
or
R11 and R12 form together with the atom to which they are attached, a ring selected from cyclopropane, cyclobutane, cyclopentane, cyclohexane and cycloheptane;
R13 and R14
are independently of one another selected from hydrogen, —($C_1$-$C_{10}$)-alkyl, —($C_1$-$C_6$)-alkyl-C(O)—$NH_2$, —($C_1$-$C_4$)-alkyl-C(O)—OH and —($C_0$-$C_4$)-alkyl-heterocyclyl, wherein alkyl in —($C_1$-$C_{10}$)-alkyl is unsubstituted or monosubstituted, disubstituted or trisubstituted independently of one another by halogen, and wherein heterocyclyl in —($C_0$-$C_4$)-alkyl-heterocyclyl is monocyclic or bicyclic and contains 3 to 15 ring carbon atoms, wherein one or more of the ring carbon atoms are replaced by 1, 2, 3 or 4 heteroatoms chosen from nitrogen, sulfur and oxygen, and wherein said heterocyclyl is unsubstituted or monosubstituted, disubstituted or trisubstituted independently of one another by R19;
R15 and R16
are independently of one another selected from hydrogen, —($C_1$-$C_{10}$)-alkyl, —($C_1$-$C_6$)-alkyl-C(O)—$NH_2$ and —($C_1$-$C_4$)-alkyl-C(O)—OH, wherein alkyl in —($C_1$-$C_{10}$)-alkyl is unsubstituted or monosubstituted, disubstituted or trisubstituted independently of one another by halogen;
R17 and R18
are independently of one another selected from hydrogen, —($C_1$-$C_{10}$)-alkyl, —($C_0$-$C_4$)-alkyl-($C_3$-$C_8$)-cycloalkyl and —($C_0$-$C_4$)-alkyl-($C_6$-$C_{14}$)-aryl, wherein alkyl in —(C₁-C₁₀)-alkyl is unsubstituted or monosubstituted, disubstituted or trisubstituted independently of one another by halogen, and wherein aryl in —(C₀-C₄)-alkyl-(C₆-C₁₄)-aryl is unsubstituted,
or
R17 and R18 form together with the atom to which they are attached, a ring selected from cyclopropane, cyclobutane, cyclopentane, cyclohexane and cycloheptane;
R19 is halogen, amino, cyano, methoxy, hydroxyl or —(C₁-C₆)-alkyl;
R20, R21 and R22
are independently of one another selected from hydrogen and —(C₁-C₆)-alkyl;
and their pharmaceutically acceptable salts.

In another embodiment, the invention is directed to compounds of the formula I, wherein
X1 is —(C₁-C₈)-alkyl-, wherein alkyl is unsubstituted or monosubstituted or disubstituted by one or more substituents independently selected from —NH—C(O)—(C₁-C₆)-alkyl, —(C₁-C₆)-alkyl-NH₂, —(C₁-C₆)-alkyl-C(O)—NH₂, —(C₁-C₆)-alkyl-C(O)—OH and —(C₁-C₆)-alkyl,
or
X1 is

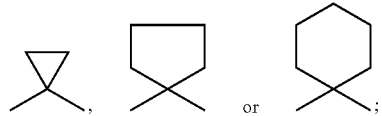

X2 is a covalent bond, —(C₁-C₈)-alkyl- or monocyclic 6-membered aryl, wherein aryl is unsubstituted;
X3 is a covalent bond, —(C₁-C₈)-alkyl- or monocyclic 6-membered aryl, wherein aryl is unsubstituted;
or
X2-X3 is —NH—C(O)—, —C(O)—NH—, —(C₀-C₈)-alkyl-O—(C₀-C₈)-alkyl- or —(C₀-C₈)-alkyl-S—(C₀-C₈)-alkyl-;
X4 is —(C₁-C₈)-alkyl-, wherein alkyl is unsubstituted or monosubstituted or disubstituted by one or more substituents independently selected from —NH—C(O)—(C₁-C₆)-alkyl, —(C₁-C₆)-alkyl-NH₂, —(C₁-C₆)-alkyl-C(O)—NH₂, —(C₁-C₆)-alkyl-C(O)—OH and —(C₁-C₆)-alkyl,
or
X4 is

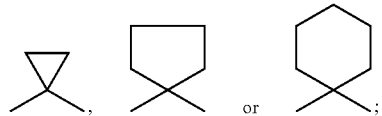

or
X1-X2-X3-X4 is —(C₁-C₈)-alkyl-O—(C₂-C₈)-alkyl-O—(C₂-C₈)-alkyl-;
R1 and R2 are independently of one another selected from hydrogen, —(C₁-C₁₀)-alkyl, —(C₁-C₆)-alkyl-C(O)—N(R20)-R21, —(C₁-C₄)-alkyl-C(O)—O—R22, —(C₁-C₆)-alkyl-OH, —(C₁-C₆)-alkyl-NH₂, —(C₁-C₆)-alkyl-C(=NH)—NH₂, —(C₁-C₆)-alkyl-NH—C(=NH)—NH₂ and —(C₀-C₄)-alkyl-heterocyclyl, wherein alkyl in —(C₁-C₁₀)-alkyl is unsubstituted or monosubstituted, disubstituted or trisubstituted independently of one another by halogen, and wherein heterocyclyl in —(C₀-C₄)-alkyl-heterocyclyl is monocyclic or bicyclic and contains 3 to 15 ring carbon atoms, wherein one or more of the ring carbon atoms are replaced by 1, 2, 3 or 4 heteroatoms chosen from nitrogen, sulfur and oxygen, and wherein said heterocyclyl is unsubstituted or monosubstituted, disubstituted or trisubstituted independently of one another by R19,
or
R1 and R2 form together with the atom to which they are attached, a ring selected from cyclopropane and cyclopentane;
R3 and R4 together with the carbon atom carrying them and the NH group and the CO group attached to the said carbon atom, form the residue of L-glutamic acid or a pharmaceutically acceptable salt or a (C₁-C₄)-alkyl ester thereof;
R5 and R6 are independently of one another selected from hydrogen, —(C₁-C₆)-alkyl-NH₂, —(C₁-C₆)-alkyl-NH—C(=NH)—NH₂,

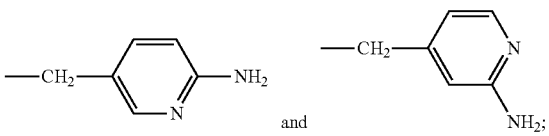

R7 and R8 are independently of one another selected from hydrogen, —(C₁-C₁₀)-alkyl, —(C₁-C₆)-alkyl-O—CH₃, —(C₁-C₆)-alkyl-S—CH₃, —(C₀-C₄)-alkyl-(C₃-C₈)-cycloalkyl and —(C₀-C₄)-alkyl-(C₆-C₁₄)-aryl, wherein alkyl in —(C₁-C₁₀)-alkyl is unsubstituted or monosubstituted, disubstituted or trisubstituted independently of one another by halogen, and wherein aryl in —(C₀-C₄)-alkyl-(C₆-C₁₄)-aryl is unsubstituted or monosubstituted, disubstituted or trisubstituted independently of one another by R19;
R9 and R10 are independently of one another selected from hydrogen, —(C₁-C₁₀)-alkyl, —(C₁-C₆)-alkyl-C(O)—NH₂, —(C₁-C₄)-alkyl-C(O)—OH, —(C₁-C₆)-alkyl-O—CH₃, —(C₁-C₆)-alkyl-S—CH₃, —(C₁-C₆)-alkyl-NH₂ and —(C₀-C₄)-alkyl-(C₃-C₈)-cycloalkyl, wherein alkyl in —(C₁-C₁₀)-alkyl is unsubstituted or monosubstituted, disubstituted or trisubstituted independently of one another by halogen;
R11 and R12
are independently of one another selected from hydrogen, —(C₁-C₁₀)-alkyl, —(C₀-C₄)-alkyl-(C₃-C₈)-cycloalkyl and —(C₀-C₄)-alkyl-(C₆-C₁₄)-aryl, wherein aryl is unsubstituted, and wherein alkyl in —(C₁-C₁₀)-alkyl is unsubstituted or monosubstituted, disubstituted or trisubstituted independently of one another by halogen,
or
R11 and R12 form together with the atom to which they are attached, a ring selected from cyclopropane, cyclobutane, cyclopentane, cyclohexane and cycloheptane;
R13 and R14
are independently of one another selected from hydrogen, —(C₁-C₁₀)-alkyl, —(C₁-C₆)-alkyl-C(O)—NH₂, —(C₁-C₄)-alkyl-C(O)—OH and —(C₀-C₄)-alkyl-heterocyclyl, wherein alkyl in —(C₁-C₁₀)-alkyl is unsubstituted or monosubstituted, disubstituted or trisubstituted independently of one another by halogen, and wherein heterocyclyl in —(C₀-C₄)-alkyl-heterocyclyl is monocyclic or bicyclic and contains 3 to 15 ring carbon atoms, wherein one or more of the ring carbon atoms are replaced by 1, 2, 3 or 4 heteroatoms chosen from nitrogen, sulfur and oxygen, and wherein said heterocyclyl is unsubstituted or monosubstituted, disubstituted or trisubstituted independently of one another by R19;

R15 and R16
together with the carbon atom carrying them and the NH group and the CO group attached to the said carbon atom, form the residue of L-asparagine;

R17 and R18
together with the carbon atom carrying them and the NH group and the CO group attached to the said carbon atom, form the residue of L-leucine;

R19 is halogen, amino, cyano, methoxy, hydroxyl or —($C_1$-$C_6$)-alkyl;

R20, R21 and R22
are independently of one another selected from hydrogen and —($C_1$-$C_6$)-alkyl;

and their pharmaceutically acceptable salts.

In another embodiment, the invention is directed to compounds of the formula I, wherein X1 is —($C_1$-$C_8$)-alkyl-, wherein alkyl is unsubstituted or monosubstituted or disubstituted by one or more substituents independently selected from —NH—C(O)—($C_1$-$C_6$)-alkyl, —($C_1$-$C_6$)-alkyl-$NH_2$, —($C_1$-$C_6$)-alkyl-C(O)—$NH_2$, —($C_1$-$C_6$)-alkyl-C(O)—OH and —($C_1$-$C_6$)-alkyl, or X1 is

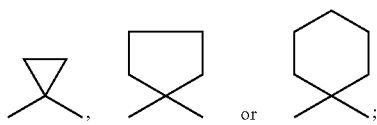

X2 is a covalent bond, —($C_1$-$C_8$)-alkyl- or monocyclic 6-membered aryl, wherein aryl is unsubstituted;

X3 is a covalent bond, —($C_1$-$C_8$)-alkyl- or monocyclic 6-membered aryl, wherein aryl is unsubstituted; or X2-X3 is —NH—C(O)—, —C(O)—NH—, —($C_0$-$C_8$)-alkyl-O—($C_0$-$C_8$)-alkyl- or —($C_0$-$C_8$)-alkyl-S—($C_0$-$C_8$)-alkyl-;

X4 is —($C_1$-$C_8$)-alkyl-, wherein alkyl is unsubstituted or monosubstituted or disubstituted by one or more substituents independently selected from —NH—C(O)—($C_1$-$C_6$)-alkyl, —($C_1$-$C_6$)-alkyl-$NH_2$, —($C_1$-$C_6$)-alkyl-C(O)—$NH_2$, —($C_1$-$C_6$)-alkyl-C(O)—OH and —($C_1$-$C_6$)-alkyl, or X4 is

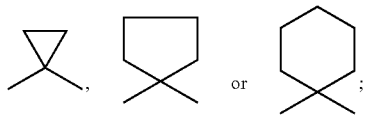

or

X1-X2-X3-X4 is —($C_1$-$C_8$)-alkyl-O—($C_2$-$C_8$)-alkyl-O—($C_2$-$C_8$)-alkyl-;

R1 and R2 are independently of one another selected from hydrogen, —($C_1$-$C_{10}$)-alkyl, —($C_1$-$C_6$)-alkyl-C(O)—N(R20)-R21, —($C_1$-$C_4$)-alkyl-C(O)—O—R22, —($C_1$-$C_6$)-alkyl-C(=NH)—$NH_2$, —($C_1$-$C_6$)-alkyl-NH—C(=NH)—$NH_2$ and —($C_0$-$C_4$)-alkyl-heterocyclyl, wherein alkyl in —($C_1$-$C_{10}$)-alkyl is unsubstituted or monosubstituted, disubstituted or trisubstituted independently of one another by halogen, and wherein heterocyclyl in —($C_0$-$C_4$)-alkyl-heterocyclyl is monocyclic or bicyclic and contains 3 to 15 ring carbon atoms, wherein one or more of the ring carbon atoms are replaced by 1, 2, 3 or 4 heteroatoms chosen from nitrogen, sulfur and oxygen, and wherein said heterocyclyl is unsubstituted or monosubstituted, disubstituted or trisubstituted independently of one another by R19, or R1 and R2 form together with the atom to which they are attached, a ring selected from cyclopropane and cyclopentane;

R3 and R4 together with the carbon atom carrying them and the NH group and the CO group attached to the said carbon atom, form the residue of L-glutamic acid or a pharmaceutically acceptable salt or a ($C_1$-$C_4$)-alkyl ester thereof;

R5 and R6 together with the carbon atom carrying them and the NH group and the CO group attached to the said carbon atom, form the residue of L-arginine, L-2,3-diaminopropionic acid, L-lysine or L-ornithine, or a pharmaceutically acceptable salt thereof;

R7 and R8 are independently of one another selected from hydrogen, —($C_1$-$C_{10}$)-alkyl, —($C_1$-$C_6$)-alkyl-O—$CH_3$, —($C_1$-$C_6$)-alkyl-S—$CH_3$, —($C_0$-$C_4$)-alkyl-($C_3$-$C_8$)-cycloalkyl and —($C_0$-$C_4$)-alkyl-($C_6$-$C_{14}$)-aryl, wherein alkyl in —($C_1$-$C_{10}$)-alkyl is unsubstituted or monosubstituted, disubstituted or trisubstituted independently of one another by halogen, and wherein aryl in —($C_0$-$C_4$)-alkyl-($C_6$-$C_{14}$)-aryl is unsubstituted or monosubstituted, disubstituted or trisubstituted independently of one another by R19;

R9 and R10 together with the carbon atom carrying them and the NH group and the CO group attached to the said carbon atom, form the residue of L-alanine, L-arginine, L-2,3-diaminopropionic acid, L-glutamine or L-norvaline, or a pharmaceutically acceptable salt thereof;

R11 and R12
are independently of one another selected from hydrogen, —($C_1$-$C_{10}$)-alkyl, —($C_0$-$C_4$)-alkyl-($C_3$-$C_8$)-cycloalkyl and —($C_0$-$C_4$)-alkyl-($C_6$-$C_{14}$)-aryl, wherein aryl is unsubstituted, and wherein alkyl in —($C_1$-$C_{10}$)-alkyl is unsubstituted or monosubstituted, disubstituted or trisubstituted independently of one another by halogen, or R11 and R12 form together with the atom to which they are attached, a ring selected from cyclopropane, cyclobutane, cyclopentane, cyclohexane and cycloheptane;

R13 and R14
together with the carbon atom carrying them and the NH group and the CO group attached to the said carbon atom, form the residue of L-histidine, D-histidine, L-ornithine or D-aspartic acid, or a pharmaceutically acceptable salt thereof;

R15 and R16
together with the carbon atom carrying them and the NH group and the CO group attached to the said carbon atom, form the residue of L-asparagine;

R17 and R18
together with the carbon atom carrying them and the NH group and the CO group attached to the said carbon atom, form the residue of L-leucine;

R19 is halogen, amino, cyano, methoxy, hydroxyl or —($C_1$-$C_6$)-alkyl;

R20, R21 and R22
are independently of one another selected from hydrogen and —($C_1$-$C_6$)-alkyl;

and their pharmaceutically acceptable salts.

In another embodiment, the invention is directed to compounds of the formula I, wherein X1 is —(C$_1$-C$_8$)-alkyl-, wherein alkyl is unsubstituted or monosubstituted or disubstituted by one or more substituents independently selected from —NH—C(O)—(C$_1$-C$_6$)-alkyl, —(C$_1$-C$_6$)-alkyl-NH$_2$, —(C$_1$-C$_6$)-alkyl-C(O)—NH$_2$, —(C$_1$-C$_6$)-alkyl-C(O)—OH and —(C$_1$-C$_6$)-alkyl, or X1 is

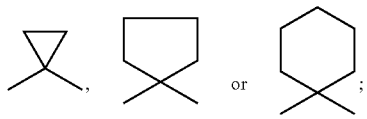

X2 is a covalent bond, —(C$_1$-C$_8$)-alkyl- or monocyclic 6-membered aryl, wherein aryl is unsubstituted;
X3 is a covalent bond, —(C$_1$-C$_8$)-alkyl- or monocyclic 6-membered aryl, wherein aryl is unsubstituted;

or

X2-X3 is —NH—C(O)—, —C(O)—NH—, —(C$_0$-C$_8$)-alkyl-O—(C$_0$-C$_8$)-alkyl- or —(C$_0$-C$_8$)-alkyl-S—(C$_0$-C$_8$)-alkyl-;
X4 is —(C$_1$-C$_8$)-alkyl-, wherein alkyl is unsubstituted or monosubstituted or disubstituted by one or more substituents independently selected from —NH—C(O)—(C$_1$-C$_6$)-alkyl, —(C$_1$-C$_6$)-alkyl-NH$_2$, —(C$_1$-C$_6$)-alkyl-C(O)—NH$_2$, —(C$_1$-C$_6$)-alkyl-C(O)—OH and —(C$_1$-C$_6$)-alkyl, or X4 is

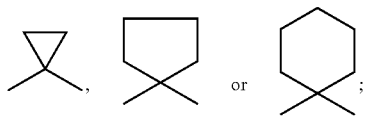

or

X1-X2-X3-X4 is —(C$_1$-C$_8$)-alkyl-O—(C$_2$-C$_8$)-alkyl-O—(C$_2$-C$_8$)-alkyl-;
R1 and R2 together with the carbon atom carrying them and the NH group and the CO group attached to the said carbon atom, form the residue of 1-aminocyclopropane-1-carboxylic acid, 1-aminocyclopentane-1-carboxylic acid, L-asparagine, L-aspartic acid, L-2,3-diaminobutyric acid, L-glutamine, L-histidine, L-leucine, L-serine or L-threonine, or a pharmaceutically acceptable salt or a (C$_1$-C$_4$)-alkyl ester thereof;
R3 and R4 together with the carbon atom carrying them and the NH group and the CO group attached to the said carbon atom, form the residue of L-glutamic acid or a pharmaceutically acceptable salt or a (C$_1$-C$_4$)-alkyl ester thereof;
R5 and R6 together with the carbon atom carrying them and the NH group and the CO group attached to the said carbon atom, form the residue of L-arginine, L-2,3-diaminopropionic acid, L-lysine or L-ornithine, or a pharmaceutically acceptable salt thereof;
R7 and R8 together with the carbon atom carrying them and the NH group and the CO group attached to the said carbon atom, form the residue of L-alanine, L-2-aminobutyric acid, L-2-amino-4-methoxybutyric acid, L-2-amino-3-methoxypropionic acid, L-cyclohexylalanine, L-cyclohexylglycine, L-glutamine, L-isoleucine, L-leucine, L-methionine or L-norleucine;

R9 and R10 together with the carbon atom carrying them and the NH group and the CO group attached to the said carbon atom, form the residue of L-alanine, L-arginine, L-2,3-diaminopropionic acid, L-glutamine or L-norvaline, or a pharmaceutically acceptable salt thereof;
R11 and R12
together with the carbon atom carrying them and the NH group and the CO group attached to the said carbon atom, form the residue of 1-aminocyclohexane-1-carboxylic acid, L-cyclohexylalanine, L-cyclohexylglycine, L-isoleucine, L-leucine, L-neopentylglycine, L-norleucine or L-norvaline;
R13 and R14
together with the carbon atom carrying them and the NH group and the CO group attached to the said carbon atom, form the residue of L-histidine, D-histidine, L-ornithine or D-aspartic acid, or a pharmaceutically acceptable salt thereof;
R15 and R16
together with the carbon atom carrying them and the NH group and the CO group attached to the said carbon atom, form the residue of L-asparagine;
R17 and R18
together with the carbon atom carrying them and the NH group and the CO group attached to the said carbon atom, form the residue of L-leucine;
and their pharmaceutically acceptable salts.

In another embodiment, the invention is directed to compounds of the formula I, wherein
X1 is —(C$_1$-C$_6$)-alkyl-, wherein alkyl is unsubstituted or monosubstituted or disubstituted by one or two substituents independently selected from —NH—C(O)—(C$_1$-C$_6$)-alkyl, —(C$_1$-C$_6$)-alkyl-NH$_2$, —(C$_1$-C$_6$)-alkyl-C(O)—NH$_2$, and —(C$_1$-C$_6$)-alkyl, or X1 is

wherein n is 1, 2, 3 or 4;
X2 is a covalent bond, —(C$_1$-C$_4$)-alkyl- or phenyl, wherein phenyl is unsubstituted;
X3 is a covalent bond or phenyl, wherein phenyl is unsubstituted;

or

X2-X3 is —NH—C(O)— or —C(O)—NH—;
X4 is —(C$_1$-C$_6$)-alkyl-, wherein alkyl is unsubstituted or monosubstituted or disubstituted by one or two substituents independently selected from —NH—C(O)—(C$_1$-C$_6$)-alkyl, —(C$_1$-C$_6$)-alkyl-NH$_2$, —(C$_1$-C$_6$)-alkyl-C(O)—NH$_2$ and —(C$_1$-C$_6$)-alkyl;

or

X1-X2-X3-X4 is —(C$_1$-C$_4$)-alkyl-O—(C$_2$-C$_4$)-alkyl-O—(C$_2$-C$_4$)-alkyl-;
R1 is selected from hydrogen and (C$_1$-C$_4$)-alkyl;
R2 is selected from —(C$_1$-C$_8$)-alkyl, —(C$_1$-C$_6$)-alkyl-C(O)—N(R20)-R21, —(C$_1$-C$_4$)-alkyl-C(O)—O—R22, —(C$_1$-C$_6$)-alkyl-OH, —(C$_1$-C$_6$)-alkyl-NH$_2$, —(C$_1$-C$_6$)-alkyl-NH—C(═NH)—NH$_2$ and —(C$_0$-C$_4$)-alkyl-heterocyclyl, wherein alkyl in —(C$_1$-C$_8$)-alkyl is unsubstituted or monosubstituted, disubstituted or trisubstituted independently of one another by halogen, and wherein heterocyclyl in —(C$_0$-C$_4$)-alkyl-heterocyclyl is monocyclic or bicyclic and contains 5 to 10 ring carbon atoms, wherein one or two of the ring carbon atoms are replaced by heteroatoms chosen from nitrogen, sulfur and oxygen, and wherein said heterocyclyl is unsubstituted or monosubstituted or disubstituted independently of one another by R19, or R1 and R2 form together with the atom to which they are attached, a ring selected from cyclopropane, cyclobutane, cyclopentane and cyclohexane;

R3 is hydrogen;

R4 is —($C_1$-$C_4$)-alkyl-C(O)—O—R22;

R5 is hydrogen;

R6 is selected from —($C_1$-$C_6$)-alkyl-$NH_2$ and —($C_1$-$C_6$)-alkyl-NH—C(=NH)—$NH_2$;

R7 is hydrogen;

R8 is selected from hydrogen, —($C_1$-$C_8$)-alkyl, —($C_1$-$C_6$)-alkyl-C(O)—N(R20)-R21, —($C_1$-$C_6$)-alkyl-O—R23, —($C_0$-$C_4$)-alkyl-($C_3$-$C_7$)-cycloalkyl and —($C_0$-$C_4$)-alkyl-phenyl, wherein alkyl in —($C_1$-$C_8$)-alkyl is unsubstituted or monosubstituted, disubstituted or trisubstituted independently of one another by halogen, and wherein phenyl in —($C_0$-$C_4$)-alkyl-phenyl is unsubstituted or monosubstituted or disubstituted independently of one another by R19;

R9 is hydrogen;

R10 is selected from hydrogen, —($C_1$-$C_8$)-alkyl, —($C_1$-$C_6$)-alkyl-C(O)—$NH_2$, —($C_1$-$C_6$)-alkyl-NH—C(=NH)—$NH_2$ and —($C_1$-$C_6$)-alkyl-$NH_2$, wherein alkyl in —($C_1$-$C_8$)-alkyl is unsubstituted or monosubstituted, disubstituted or trisubstituted independently of one another by halogen;

R11 is selected from hydrogen and ($C_1$-$C_4$)-alkyl;

R12 is selected from —($C_1$-$C_8$)-alkyl, —($C_0$-$C_4$)-alkyl-($C_3$-$C_7$)-cycloalkyl and —($C_0$-$C_4$)-alkyl-phenyl, wherein phenyl is unsubstituted, and wherein alkyl in —($C_1$-$C_8$)-alkyl is unsubstituted or monosubstituted, disubstituted or trisubstituted independently of one another by halogen, or R11 and R12 form together with the atom to which they are attached, a ring selected from cyclopentane, cyclohexane and cycloheptane;

R13 is hydrogen;

R14 is selected from —($C_1$-$C_4$)-alkyl-C(O)—O—R22, —($C_1$-$C_6$)-alkyl-$NH_2$ and —($C_0$-$C_4$)-alkyl-heterocyclyl, wherein heterocyclyl in —($C_0$-$C_4$)-alkyl-heterocyclyl is monocyclic or bicyclic and contains 5 to 10 ring carbon atoms, wherein one or two of the ring carbon atoms are replaced by heteroatoms chosen from nitrogen, sulfur and oxygen, and wherein said heterocyclyl is unsubstituted or monosubstituted or disubstituted independently of one another by R19;

R15 is hydrogen;

R16 is selected from —($C_1$-$C_4$)-alkyl-C(O)—$NH_2$;

R17 is hydrogen;

R18 is selected from —($C_1$-$C_6$)-alkyl, wherein alkyl in —($C_1$-$C_6$)-alkyl is unsubstituted or monosubstituted, disubstituted or trisubstituted independently of one another by halogen;

R19 is halogen or —($C_1$-$C_4$)-alkyl;

R20, R21, R22, R23 and R24
are independently of one another selected from hydrogen and —($C_1$-$C_6$)-alkyl;

and their pharmaceutically acceptable salts.

In another embodiment, the invention is directed to compounds of the formula I, wherein X1 is —($C_1$-$C_6$)-alkyl-, wherein alkyl is unsubstituted or monosubstituted or disubstituted by one or two substituents independently selected from —NH—C(O)—($C_1$-$C_6$)-alkyl, —($C_1$-$C_6$)-alkyl-$NH_2$, —($C_1$-$C_6$)-alkyl-C(O)—$NH_2$, and —($C_1$-$C_6$)-alkyl, or X1 is

wherein n is 1, 2, 3 or 4;

X2 is a covalent bond, —($C_1$-$C_4$)-alkyl- or phenyl, wherein phenyl is unsubstituted;

X3 is a covalent bond or phenyl, wherein phenyl is unsubstituted;

or

X2-X3 is —NH—C(O)— or —C(O)—NH—;

X4 is —($C_1$-$C_6$)-alkyl-, wherein alkyl is unsubstituted or monosubstituted or disubstituted by one or two substituents independently selected from —NH—C(O)—($C_1$-$C_6$)-alkyl and —($C_1$-$C_6$)-alkyl;

or

X1-X2-X3-X4 is —($C_1$-$C_4$)-alkyl-O—($C_2$-$C_4$)-alkyl-O—($C_2$-$C_4$)-alkyl-;

R1 is selected from hydrogen and ($C_1$-$C_4$)-alkyl;

R2 is selected from —($C_1$-$C_8$)-alkyl, —($C_1$-$C_6$)-alkyl-C(O)—N(R20)-R21, —($C_1$-$C_4$)-alkyl-C(O)—O—R22, —($C_1$-$C_6$)-alkyl-OH, —($C_1$-$C_6$)-alkyl-$NH_2$, —($C_1$-$C_6$)-alkyl-NH—C(=NH)—$NH_2$ and —($C_0$-$C_4$)-alkyl-heterocyclyl, wherein alkyl in —($C_1$-$C_8$)-alkyl is unsubstituted or monosubstituted, disubstituted or trisubstituted independently of one another by halogen, and wherein heterocyclyl in —($C_0$-$C_4$)-alkyl-heterocyclyl is monocyclic or bicyclic and contains 5 to 10 ring carbon atoms, wherein one or two of the ring carbon atoms are replaced by heteroatoms chosen from nitrogen, sulfur and oxygen, and wherein said heterocyclyl is unsubstituted or monosubstituted or disubstituted independently of one another by R19, or R1 and R2 form together with the atom to which they are attached, a ring selected from cyclopropane, cyclobutane, cyclopentane and cyclohexane;

R3 and R4 together with the carbon atom carrying them and the NH group and the CO group attached to the said carbon atom, form the residue of L-glutamic acid or a pharmaceutically acceptable salt or a ($C_1$-$C_4$)-alkyl ester thereof;

R5 is hydrogen;

R6 is selected from —($C_1$-$C_6$)-alkyl-$NH_2$ and —($C_1$-$C_6$)-alkyl-NH—C(=NH)—$NH_2$;

R7 is hydrogen;

R8 is selected from hydrogen, —($C_1$-$C_8$)-alkyl, —($C_1$-$C_6$)-alkyl-C(O)—N(R20)-R21, —($C_1$-$C_6$)-alkyl-O—R23, —($C_1$-$C_6$)-alkyl-S—R24, —($C_0$-$C_4$)-alkyl-($C_3$-$C_7$)-cycloalkyl and —($C_0$-$C_4$)-alkyl-phenyl, wherein alkyl in —($C_1$-$C_8$)-alkyl is unsubstituted or monosubstituted, disubstituted or trisubstituted independently of one another by halogen, and wherein phenyl in —($C_0$-$C_4$)-alkyl-phenyl is unsubstituted or monosubstituted or disubstituted independently of one another by R19;

R9 is hydrogen;

R10 is selected from hydrogen, —($C_1$-$C_8$)-alkyl, —($C_1$-$C_6$)-alkyl-C(O)—$NH_2$, —($C_1$-$C_6$)-alkyl-NH—C(=NH)—$NH_2$ and —($C_1$-$C_6$)-alkyl-$NH_2$, wherein alkyl in —($C_1$-

$C_8$)-alkyl is unsubstituted or monosubstituted, disubstituted or trisubstituted independently of one another by halogen;

R11 is selected from hydrogen and $(C_1-C_4)$-alkyl;

R12 is selected from —$(C_1-C_8)$-alkyl, —$(C_0-C_4)$-alkyl-$(C_3-C_7)$-cycloalkyl and —$(C_0-C_4)$-alkyl-phenyl, wherein phenyl is unsubstituted, and wherein alkyl in —$(C_1-C_8)$-alkyl is unsubstituted or monosubstituted, disubstituted or trisubstituted independently of one another by halogen, or R11 and R12 form together with the atom to which they are attached, a ring selected from cyclopentane, cyclohexane and cycloheptane;

R13 is hydrogen;

R14 is selected from —$(C_1-C_4)$-alkyl-C(O)—O—R22, —$(C_1-C_6)$-alkyl-$NH_2$ and —$(C_0-C_4)$-alkyl-heterocyclyl, wherein heterocyclyl in —$(C_0-C_4)$-alkyl-heterocyclyl is monocyclic or bicyclic and contains 5 to 10 ring carbon atoms, wherein one or two of the ring carbon atoms are replaced by heteroatoms chosen from nitrogen, sulfur and oxygen, and wherein said heterocyclyl is unsubstituted or monosubstituted or disubstituted independently of one another by R19;

R15 and R16
  together with the carbon atom carrying them and the NH group and the CO group attached to the said carbon atom, form the residue of L-asparagine;

R17 and R18
  together with the carbon atom carrying them and the NH group and the CO group attached to the said carbon atom, form the residue of L-leucine;

R19 is halogen or —$(C_1-C_4)$-alkyl;

R20, R21, R22, R23 and R24
  are independently of one another selected from hydrogen and —$(C_1-C_6)$-alkyl;

and their pharmaceutically acceptable salts.

In another embodiment, the invention is directed to compounds of the formula I, wherein X1 is —$(C_1-C_6)$-alkyl-, wherein alkyl is unsubstituted or monosubstituted or disubstituted by one or two substituents independently selected from —NH—C(O)—$(C_1-C_6)$-alkyl and —$(C_1-C_6)$-alkyl, or X1 is

wherein n is 1, 2, 3 or 4;

X2 is a covalent bond, —$(C_1-C_4)$-alkyl- or phenyl, wherein phenyl is unsubstituted;

X3 is a covalent bond or phenyl, wherein phenyl is unsubstituted;

or

X2-X3 is —NH—C(O)— or —C(O)—NH—;

X4 is —$(C_1-C_6)$-alkyl-, wherein alkyl is unsubstituted or monosubstituted or disubstituted by one or two substituents independently selected from —NH—C(O)—$(C_1-C_6)$-alkyl, —$(C_1-C_6)$-alkyl-$NH_2$, —$(C_1-C_6)$-alkyl-C(O)—$NH_2$ and —$(C_1-C_6)$-alkyl;

or

X1-X2-X3-X4 is —$(C_1-C_4)$-alkyl-O—$(C_2-C_4)$-alkyl-O—$(C_2-C_4)$-alkyl-;

R1 is selected from hydrogen and $(C_1-C_4)$-alkyl;

R2 is selected from —$(C_1-C_8)$-alkyl, —$(C_1-C_6)$-alkyl-C(O)—N(R20)-R21, —$(C_1-C_4)$-alkyl-C(O)—O—R22, —$(C_1-C_6)$-alkyl-OH, —$(C_1-C_6)$-alkyl-C(O)—$NH_2$, —$(C_1-C_6)$-alkyl-NH—C(=NH)—$NH_2$ and —$(C_0-C_4)$-alkyl-heterocyclyl, wherein alkyl in —$(C_1-C_8)$-alkyl is unsubstituted or monosubstituted, disubstituted or trisubstituted independently of one another by halogen, and wherein heterocyclyl in —$(C_0-C_4)$-alkyl-heterocyclyl is monocyclic or bicyclic and contains 5 to 10 ring carbon atoms, wherein one or two of the ring carbon atoms are replaced by heteroatoms chosen from nitrogen, sulfur and oxygen, and wherein said heterocyclyl is unsubstituted or monosubstituted or disubstituted independently of one another by R19, or R1 and R2 form together with the atom to which they are attached, a ring selected from cyclopropane, cyclobutane, cyclopentane and cyclohexane;

R3 and R4 together with the carbon atom carrying them and the NH group and the CO group attached to the said carbon atom, form the residue of L-glutamic acid or a pharmaceutically acceptable salt or a $(C_1-C_4)$-alkyl ester thereof;

R5 and R6 together with the carbon atom carrying them and the NH group and the CO group attached to the said carbon atom, form the residue of L-arginine, L-2,3-diaminopropionic acid, L-lysine or L-ornithine, or a pharmaceutically acceptable salt thereof;

R7 is hydrogen;

R8 is selected from hydrogen, —$(C_1-C_8)$-alkyl, —$(C_1-C_6)$-alkyl-C(O)—N(R20)-R21, —$(C_1-C_6)$-alkyl-O—R23, —$(C_0-C_4)$-alkyl-$(C_3-C_7)$-cycloalkyl and —$(C_0-C_4)$-alkyl-phenyl, wherein alkyl in —$(C_1-C_8)$-alkyl is unsubstituted or monosubstituted, disubstituted or trisubstituted independently of one another by halogen, and wherein phenyl in —$(C_0-C_4)$-alkyl-phenyl is unsubstituted or monosubstituted or disubstituted independently of one another by R19;

R9 and R10 together with the carbon atom carrying them and the NH group and the CO group attached to the said carbon atom, form the residue of L-alanine, L-arginine, L-2,3-diaminopropionic acid, L-glutamine or L-norvaline, or a pharmaceutically acceptable salt thereof;

R11 is selected from hydrogen and $(C_1-C_4)$-alkyl;

R12 is selected from —$(C_1-C_8)$-alkyl, —$(C_0-C_4)$-alkyl-$(C_3-C_7)$-cycloalkyl and —$(C_0-C_4)$-alkyl-phenyl, wherein phenyl is unsubstituted, and wherein alkyl in —$(C_1-C_8)$-alkyl is unsubstituted or monosubstituted, disubstituted or trisubstituted independently of one another by halogen, or R11 and R12 form together with the atom to which they are attached, a ring selected from cyclopentane, cyclohexane and cycloheptane;

R13 and R14
  together with the carbon atom carrying them and the NH group and the CO group attached to the said carbon atom, form the residue of L-histidine, D-histidine, L-ornithine or D-aspartic acid, or a pharmaceutically acceptable salt or a $(C_1-C_4)$-alkyl ester thereof;

R15 and R16
  together with the carbon atom carrying them and the NH group and the CO group attached to the said carbon atom, form the residue of L-asparagine;

R17 and R18
  together with the carbon atom carrying them and the NH group and the CO group attached to the said carbon atom, form the residue of L-leucine;

R19 is halogen or —$(C_1-C_4)$-alkyl;

R20, R21, R22, R23 and R24
are independently of one another selected from hydrogen and —($C_1$-$C_6$)-alkyl;
and their pharmaceutically acceptable salts.

In another embodiment, the invention is directed to compounds of the formula I, wherein
X1 is —($C_1$-$C_6$)-alkyl-, wherein alkyl is unsubstituted or monosubstituted or disubstituted by one or two substituents independently selected from —NH—C(O)—($C_1$-$C_6$)-alkyl, —($C_1$-$C_6$)-alkyl-$NH_2$, —($C_1$-$C_6$)-alkyl-C(O)—$NH_2$, and —($C_1$-$C_6$)-alkyl,
or
X1 is

wherein n is 1, 2, 3 or 4;
X2 is a covalent bond, —($C_1$-$C_4$)-alkyl- or phenyl, wherein phenyl is unsubstituted;
X3 is a covalent bond or phenyl, wherein phenyl is unsubstituted;
or
X2-X3 is —NH—C(O)— or —C(O)—NH—;
X4 is —($C_1$-$C_6$)-alkyl-, wherein alkyl is unsubstituted or monosubstituted or disubstituted by one or two substituents independently selected from —NH—C(O)—($C_1$-$C_6$)-alkyl and —($C_1$-$C_6$)-alkyl;
or
X1-X2-X3-X4 is —($C_1$-$C_4$)-alkyl-O—($C_2$-$C_4$)-alkyl-O—($C_2$-$C_4$)-alkyl-;
R1 and R2 together with the carbon atom carrying them and the NH group and the CO group attached to the said carbon atom, form the residue of 1-aminocyclopropane-1-carboxylic acid, 1-aminocyclopentane-1-carboxylic acid, L-asparagine, L-aspartic acid, L-2,3-diaminobutyric acid, L-glutamine, L-histidine, L-leucine, L-serine or L-threonine, or a pharmaceutically acceptable salt or a ($C_1$-$C_4$)-alkyl ester thereof;
R3 and R4 together with the carbon atom carrying them and the NH group and the CO group attached to the said carbon atom, form the residue of L-glutamic acid or a pharmaceutically acceptable salt or a ($C_1$-$C_4$)-alkyl ester thereof;
R5 and R6 together with the carbon atom carrying them and the NH group and the CO group attached to the said carbon atom, form the residue of L-arginine, L-2,3-diaminopropionic acid, L-lysine or L-ornithine, or a pharmaceutically acceptable salt thereof;
R7 and R8 together with the carbon atom carrying them and the NH group and the CO group attached to the said carbon atom, form the residue of L-alanine, L-2-aminobutyric acid, L-2-amino-4-methoxybutyric acid, L-2-amino-3-methoxypropionic acid, L-cyclohexylalanine, L-cyclohexylglycine, L-glutamine, L-isoleucine, L-leucine, L-methionine or L-norleucine;
R9 and R10 together with the carbon atom carrying them and the NH group and the CO group attached to the said carbon atom, form the residue of L-alanine, L-arginine, L-2,3-diaminopropionic acid, L-glutamine or L-norvaline, or a pharmaceutically acceptable salt thereof;
R11 and R12
together with the carbon atom carrying them and the NH group and the CO group attached to the said carbon atom, form the residue of 1-aminocyclohexane-1-carboxylic acid, L-cyclohexylalanine, L-cyclohexylglycine, L-isoleucine, L-leucine, L-neopentylglycine, L-norleucine or L-norvaline;
R13 and R14
together with the carbon atom carrying them and the NH group and the CO group attached to the said carbon atom, form the residue of L-histidine, D-histidine, L-ornithine or D-aspartic acid, or a pharmaceutically acceptable salt or a ($C_1$-$C_4$)-alkyl ester thereof;
R15 and R16
together with the carbon atom carrying them and the NH group and the CO group attached to the said carbon atom, form the residue of L-asparagine;
R17 and R18
together with the carbon atom carrying them and the NH group and the CO group attached to the said carbon atom, form the residue of L-leucine;
and their pharmaceutically acceptable salts.

In one embodiment, X1 is —($C_1$-$C_8$)-alkyl-, in another embodiment —($C_1$-$C_6$)-alkyl-, wherein the alkyl groups are unsubstituted or monosubstituted or disubstituted, in another embodiment unsubstituted or monosubstituted, by one or more substituents, for example one or two substituents, which are independently selected from —NH—C(O)—($C_1$-$C_6$)-alkyl, —($C_1$-$C_6$)-alkyl-$NH_2$, —($C_1$-$C_6$)-alkyl-C(O)—$NH_2$, —($C_1$-$C_6$)-alkyl-C(O)—OH and —($C_1$-$C_6$)-alkyl, in another embodiment from —NH—C(O)—($C_1$-$C_6$)-alkyl, —($C_1$-$C_6$)-alkyl-$NH_2$, —($C_1$-$C_6$)-alkyl-C(O)—$NH_2$ and —($C_1$-$C_6$)-alkyl, in another embodiment from —NH—C(O)—($C_1$-$C_6$)-alkyl, —($C_1$-$C_6$)-alkyl-C(O)—$NH_2$ and —($C_1$-$C_6$)-alkyl, in another embodiment from —NH—C(O)—($C_1$-$C_6$)-alkyl and —($C_1$-$C_6$)-alkyl, in another embodiment from —($C_1$-$C_6$)-alkyl-C(O)—$NH_2$ and —($C_1$-$C_6$)-alkyl, or X1 is

wherein n is 1, 2, 3, 4 or 5, in another embodiment 1, 2, 3 or 4, in another embodiment 1, 2 or 3, in another embodiment 1. In another embodiment, X1 is —($C_1$-$C_8$)-alkyl-, in another embodiment —($C_1$-$C_6$)-alkyl-, wherein the alkyl groups are unsubstituted or monosubstituted or disubstituted, in another embodiment unsubstituted or monosubstituted, by one or more substituents, for example one or two substituents, which are independently selected from —NH—C(O)—($C_1$-$C_6$)-alkyl, —($C_1$-$C_6$)-alkyl-$NH_2$, —($C_1$-$C_6$)-alkyl-C(O)—$NH_2$, —($C_1$-$C_6$)-alkyl-C(O)—OH and —($C_1$-$C_6$)-alkyl, in another embodiment from —NH—C(O)—($C_1$-$C_6$)-alkyl, —($C_1$-$C_6$)-alkyl-$NH_2$, —($C_1$-$C_6$)-alkyl-C(O)—$NH_2$ and —($C_1$-$C_6$)-alkyl, in another embodiment from —NH—C(O)—($C_1$-$C_6$)-alkyl, —($C_1$-$C_6$)-alkyl-C(O)—$NH_2$ and —($C_1$-$C_6$)-alkyl, in another embodiment from —NH—C(O)—($C_1$-$C_6$)-alkyl and —($C_1$-$C_6$)-alkyl, in another embodiment from —($C_1$-$C_6$)-alkyl-C(O)—$NH_2$ and —($C_1$-$C_6$)-alkyl, or X1 is

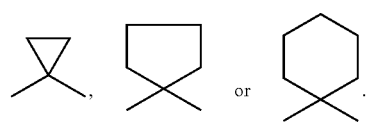

In another embodiment, X1 is —($C_1$-$C_8$)-alkyl-, in another embodiment —($C_1$-$C_6$)-alkyl-, wherein the alkyl groups are unsubstituted or monosubstituted or disubstituted, in another embodiment unsubstituted or monosubstituted, by one or more substituents, for example one or two substituents, which are independently selected from —NH—C(O)—($C_1$-$C_6$)-alkyl, —($C_1$-$C_6$)-alkyl-$NH_2$, —($C_1$-$C_6$)-alkyl-C(O)—$NH_2$, —($C_1$-$C_6$)-alkyl-C(O)—OH and —($C_1$-$C_6$)-alkyl, in another embodiment from —NH—C(O)—($C_1$-$C_6$)-alkyl, —($C_1$-$C_6$)-alkyl-$NH_2$, —($C_1$-$C_6$)-alkyl-C(O)—$NH_2$ and —($C_1$-$C_6$)-alkyl, in another embodiment from —NH—C(O)—($C_1$-$C_6$)-alkyl, —($C_1$-$C_6$)-alkyl-C(O)—$NH_2$ and —($C_1$-$C_6$)-alkyl, in another embodiment from —NH—C(O)—($C_1$-$C_6$)-alkyl and —($C_1$-$C_6$)-alkyl, in another embodiment from —($C_1$-$C_6$)-alkyl-C(O)—$NH_2$ and —($C_1$-$C_6$)-alkyl. In another embodiment, X1 is, for example, methylene, ethylene, propylene, butylene, pentylene or hexylene, wherein methylene is unsubstituted or monosubstituted or disubstituted by one or more substituents independently selected from —NH—C(O)—($C_1$-$C_6$)-alkyl, —($C_1$-$C_6$)-alkyl-$NH_2$, —($C_1$-$C_6$)-alkyl-C(O)—$NH_2$, —($C_1$-$C_6$)-alkyl-C(O)—OH and —($C_1$-$C_6$)-alkyl, in another embodiment from —NH—C(O)—($C_1$-$C_6$)-alkyl, —($C_1$-$C_6$)-alkyl-$NH_2$, —($C_1$-$C_6$)-alkyl-C(O)—$NH_2$ and —($C_1$-$C_6$)-alkyl, in another embodiment from —NH—C(O)—($C_1$-$C_6$)-alkyl, —($C_1$-$C_6$)-alkyl-C(O)—$NH_2$ and —($C_1$-$C_6$)-alkyl, in another embodiment from —NH—C(O)—($C_1$-$C_6$)-alkyl and —($C_1$-$C_6$)-alkyl, in another embodiment from —($C_1$-$C_6$)-alkyl-C(O)—$NH_2$ and —($C_1$-$C_6$)-alkyl. In another embodiment, X1 is —($C_1$-$C_8$)-alkyl-, in another embodiment —($C_1$-$C_6$)-alkyl-, wherein the alkyl groups are unsubstituted and, for example, are selected from the groups methylene, ethylene, propylene, butylene, pentylene, hexylene, heptylene and octylene, in another embodiment from the groups methylene, ethylene, propylene, butylene, pentylene and hexylene.

In one embodiment, X2 is a covalent bond, —($C_1$-$C_8$)-alkyl- or monocyclic 6-membered aryl, wherein aryl is unsubstituted or monosubstituted, disubstituted, trisubstituted or tetrasubstituted, in another embodiment unsubstituted, monosubstituted or disubstituted, in another embodiment unsubstituted or monosubstituted, independently of one another by R19. In another embodiment, X2 is a covalent bond, —($C_1$-$C_8$)-alkyl- or monocyclic 6-membered aryl, wherein aryl is unsubstituted. In one embodiment, the group —($C_1$-$C_8$)-alkyl- representing X2 is —($C_1$-$C_6$)-alkyl-, in another embodiment —($C_1$-$C_4$)-alkyl-. In another embodiment, X2 is a covalent bond, —($C_1$-$C_4$)-alkyl- or unsubstituted phenylene, in another embodiment X2 is a covalent bond or unsubstituted phenylene, in another embodiment X2 is a covalent bond.

In one embodiment, X3 is a covalent bond, —($C_1$-$C_8$)-alkyl- or monocyclic 6-membered aryl, wherein aryl is unsubstituted or monosubstituted, disubstituted, trisubstituted or tetrasubstituted, in another embodiment unsubstituted, monosubstituted or disubstituted, in another embodiment unsubstituted or monosubstituted, independently of one another by R19. In another embodiment, X3 is a covalent bond, —($C_1$-$C_8$)-alkyl- or monocyclic 6-membered aryl, wherein aryl is unsubstituted. In one embodiment, the group —($C_1$-$C_8$)-alkyl- representing X3 is —($C_1$-$C_6$)-alkyl-, in another embodiment —($C_1$-$C_4$)-alkyl-. In another embodiment, X3 is a covalent bond, —($C_1$-$C_4$)-alkyl- or unsubstituted phenylene, in another embodiment X3 is a covalent bond or unsubstituted phenylene, in another embodiment X3 is a covalent bond.

In one embodiment, X4 is —($C_1$-$C_8$)-alkyl-, in another embodiment —($C_1$-$C_6$)-alkyl-, wherein the alkyl groups are unsubstituted or monosubstituted or disubstituted, in another embodiment unsubstituted or monosubstituted, by one or more substituents, for example one or two substituents, which are independently selected from —NH—C(O)—($C_1$-$C_6$)-alkyl, —($C_1$-$C_6$)-alkyl-$NH_2$, —($C_1$-$C_6$)-alkyl-C(O)—$NH_2$, —($C_1$-$C_6$)-alkyl-C(O)—OH and —($C_1$-$C_6$)-alkyl, in another embodiment from —NH—C(O)—($C_1$-$C_6$)-alkyl, —($C_1$-$C_6$)-alkyl-$NH_2$, —($C_1$-$C_6$)-alkyl-C(O)—$NH_2$ and —($C_1$-$C_6$)-alkyl, in another embodiment from —NH—C(O)—($C_1$-$C_6$)-alkyl, —($C_1$-$C_6$)-alkyl-C(O)—$NH_2$ and —($C_1$-$C_6$)-alkyl, in another embodiment from —NH—C(O)—($C_1$-$C_6$)-alkyl and —($C_1$-$C_6$)-alkyl, in another embodiment from —($C_1$-$C_6$)-alkyl-C(O)—$NH_2$ and —($C_1$-$C_6$)-alkyl, or X4 is

wherein m is 1, 2, 3, 4 or 5, in another embodiment 1, 2, 3 or 4, in another embodiment 1, 2 or 3, in another embodiment 1. In another embodiment, X4 is —($C_1$-$C_8$)-alkyl-, in another embodiment —($C_1$-$C_6$)-alkyl-, wherein the alkyl groups are unsubstituted or monosubstituted or disubstituted, in another embodiment unsubstituted or monosubstituted, by one or more substituents, for example one or two substituents, which are independently selected from —NH—C(O)—($C_1$-$C_6$)-alkyl, —($C_1$-$C_6$)-alkyl-C(O)—$NH_2$, —($C_1$-$C_6$)-alkyl-C(O)—$NH_2$, —($C_1$-$C_6$)-alkyl-C(O)—OH and —($C_1$-$C_6$)-alkyl, in another embodiment from —NH—C(O)—($C_1$-$C_6$)-alkyl, —($C_1$-$C_6$)-alkyl-$NH_2$, —($C_1$-$C_6$)-alkyl-C(O)—$NH_2$ and —($C_1$-$C_6$)-alkyl, in another embodiment from —NH—C(O)—($C_1$-$C_6$)-alkyl, —($C_1$-$C_6$)-alkyl-C(O)—$NH_2$ and —($C_1$-$C_6$)-alkyl, in another embodiment from —NH—C(O)—($C_1$-$C_6$)-alkyl and —($C_1$-$C_6$)-alkyl, in another embodiment from —($C_1$-$C_6$)-alkyl-C(O)—$NH_2$ and —($C_1$-$C_6$)-alkyl, or X4 is

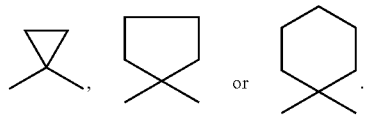

In another embodiment, X4 is —($C_1$-$C_8$)-alkyl-, in another embodiment —($C_1$-$C_6$)-alkyl-, wherein the alkyl groups are unsubstituted or monosubstituted or disubstituted, in another embodiment unsubstituted or monosubstituted, by one or more substituents, for example one or two substituents, which are independently selected from —NH—C(O)—($C_1$-$C_6$)-alkyl, —($C_1$-$C_6$)-alkyl-$NH_2$, —($C_1$-$C_6$)-alkyl-C(O)—$NH_2$, —($C_1$-$C_6$)-alkyl-C(O)—OH and —($C_1$-$C_6$)-alkyl, in another embodiment from —NH—C(O)—($C_1$-$C_6$)-alkyl, —($C_1$-$C_6$)-alkyl-$NH_2$, —($C_1$-$C_6$)-alkyl-C(O)—$NH_2$ and —($C_1$-$C_6$)-alkyl, in another embodiment from —NH—C(O)—($C_1$-$C_6$)-alkyl, —($C_1$-$C_6$)-alkyl-C(O)—$NH_2$ and —($C_1$-$C_6$)-alkyl, in another embodiment from —NH—C(O)—($C_1$-$C_6$)-alkyl and —($C_1$-$C_6$)-alkyl, in another embodiment from —($C_1$-$C_6$)-alkyl-C(O)—$NH_2$ and —($C_1$-$C_6$)-alkyl. In another embodiment, X4 is, for example, methylene, ethylene, propylene, butylene, pentylene or hexylene, wherein methylene is unsubstituted or monosubstituted or disubstituted by one or more substituents independently selected from —NH—C(O)—($C_1$-$C_6$)-alkyl, —($C_1$-$C_6$)-alkyl-$NH_2$, —($C_1$-$C_6$)-alkyl-C(O)—$NH_2$, —($C_1$-$C_6$)-alkyl-C(O)—OH and —($C_1$-$C_6$)-alkyl, in another embodiment from —NH—C(O)—($C_1$-$C_6$)-alkyl, —($C_1$-$C_6$)-alkyl-$NH_2$, —($C_1$-$C_6$)- alkyl-C(O)—NH$_2$ and —(C$_1$-C$_6$)-alkyl, in another embodiment from —NH—C(O)—(C$_1$-C$_6$)-alkyl, —(C$_1$-C$_6$)-alkyl-C(O)—NH$_2$ and —(C$_1$-C$_6$)-alkyl, in another embodiment from —NH—C(O)—(C$_1$-C$_6$)-alkyl and —(C$_1$-C$_6$)-alkyl, in another embodiment from —(C$_1$-C$_6$)-alkyl-C(O)—NH$_2$ and —(C$_1$-C$_6$)-alkyl. In another embodiment, X4 is —(C$_1$-C$_8$)-alkyl-, in another embodiment —(C$_1$-C$_6$)-alkyl-, in another embodiment —(C$_1$-C$_4$)-alkyl, wherein the alkyl groups are unsubstituted and, for example, are selected from the groups methylene, ethylene, propylene, butylene, pentylene, hexylene, heptylene and octylene, in another embodiment from the groups methylene, ethylene, propylene, butylene, pentylene and hexylene.

In one embodiment, X2-X3 is —NH—C(O)—, —C(O)—NH—, —(C$_0$-C$_8$)-alkyl-O—(C$_0$-C$_8$)-alkyl- or —(C$_0$-C$_8$)-alkyl-S—(C$_0$-C$_8$)-alkyl-, in another embodiment —NH—C(O)—, —C(O)—NH— or —(C$_0$-C$_8$)-alkyl-O—(C$_0$-C$_8$)-alkyl-, in another embodiment —NH—C(O)— or —C(O)—NH—, in another embodiment —C(O)—NH—, in another embodiment —NH—C(O)—.

In one embodiment, the group —(C$_1$-C$_8$)-alkyl-O—(C$_2$-C$_8$)-alkyl-O—(C$_2$-C$_8$)-alkyl-representing X1-X2-X3-X4 is the group —(C$_1$-C$_8$)-alkyl-O—(C$_2$-C$_8$)-alkyl-O—(C$_2$-C$_6$)-alkyl-, in another embodiment the group —(C$_1$-C$_4$)-alkyl-O—(C$_2$-C$_4$)-alkyl-O—(C$_2$-C$_4$)-alkyl-, in another embodiment the group —(C$_1$-C$_2$)-alkyl-O—(C$_2$-C$_3$)-alkyl-O—(C$_2$-C$_3$)-alkyl-, in another embodiment the group —CH$_2$—O—CH$_2$—CH$_2$—O—CH$_2$—CH$_2$—, wherein in the said groups the terminal alkyl moiety at the left side is bonded to the CO group to which X1 is bonded in formula I, and the terminal alkyl moiety at the right side is bonded to the NH group to which X4 is bonded in formula I. In one embodiment, the central alkyl moiety in the said groups, which is bonded to two oxygen atoms, comprises a chain of at least two carbon atoms to the terminal carbon atoms of which the oxygen atoms are bonded, and the alkyl moiety at the left side in the said groups, which is bonded to an oxygen atom and the group NH, comprises a chain of at least two carbon atoms to the terminal carbon atoms of which the oxygen atom and the group NH are bonded. One embodiment of the invention comprises compounds of the formula I in which the groups X1, X2, X3 and X4 are defined as in any of the definitions of the individual groups X1, X2, X3 and X4 or the combined group X2-X3, but not as in the definition of the combined group X1-X2-X3-X4, i.e., in this embodiment X1-X2-X3-X4 is not the group —(C$_1$-C$_8$)-alkyl-O—(C$_2$-C$_8$)-alkyl-O—(C$_2$-C$_8$)-alkyl- or any of the other mentioned embodiments of this group. Another embodiment of the invention comprises compounds of the formula I in which the groups X1, X2, X3 and X4 are defined as in any of the definitions of the individual groups X1, X2, X3 and X4, but not as in the definitions of the combined groups X2-X3 and X1-X2-X3-X4, i.e., in this embodiment X1-X2-X3-X4 is not the group —(C$_1$-C$_8$)-alkyl-O—(C$_2$-C$_8$)-alkyl-O—(C$_2$-C$_8$)-alkyl- or any of the other mentioned embodiments of this group, and X2-X3 is not is —NH—C(O)—, —C(O)—NH—, —(C$_0$-C$_8$)-alkyl-O—(C$_0$-C$_8$)-alkyl- or —(C$_0$-C$_8$)-alkyl-S—(C$_0$-C$_8$)-alkyl- and any of the other mentioned embodiments of these groups.

In case R1 and R2 form together with the atom to which they are attached a ring, in one embodiment the ring is selected from cyclopropane, cyclobutane, cyclopentane and cyclohexane, in another embodiment from cyclopropane, cyclobutane and cyclopentane, in another embodiment from cyclopentane and cyclohexane, in another embodiment from cyclopropane and cyclobutane, in another embodiment from cyclopropane and cyclopentane.

In one embodiment, R1 and R2 are independently of one another selected from hydrogen, —(C$_1$-C$_{10}$)-alkyl, —(C$_1$-C$_6$)-alkyl-C(O)—N(R20)-R21, —(C$_1$-C$_4$)-alkyl-C(O)—O—R22, —(C$_1$-C$_6$)-alkyl-OH, —(C$_1$-C$_6$)-alkyl-NH$_2$, —(C$_1$-C$_6$)-alkyl-C(=NH)—NH$_2$, —(C$_1$-C$_6$)-alkyl-NH—C(=NH)—NH$_2$ and —(C$_0$-C$_4$)-alkyl-heterocyclyl, wherein alkyl in —(C$_1$-C$_{10}$)-alkyl is unsubstituted or monosubstituted, disubstituted or trisubstituted independently of one another by halogen and wherein heterocyclyl in —(C$_0$-C$_4$)-alkyl-heterocyclyl is monocyclic or bicyclic and contains 3 to 15 ring carbon atoms and wherein one or more of the ring carbon atoms are replaced by 1, 2, 3 or 4 heteroatoms chosen from nitrogen, sulfur and oxygen, and wherein said heterocyclyl is unsubstituted or monosubstituted, disubstituted or trisubstituted independently of one another by R19, or R1 and R2 form together with the atom to which they are attached a ring selected from cyclopropane and cyclopentane.

In another embodiment one of R1 and R2, for example R1, is hydrogen or —(C$_1$-C$_4$)-alkyl, in another embodiment hydrogen, and the other, for example R2, is selected from —(C$_1$-C$_{10}$)-alkyl, —(C$_1$-C$_6$)-alkyl-C(O)—N(R20)-R21, —(C$_1$-C$_4$)-alkyl-C(O)—O—R22, —(C$_1$-C$_6$)-alkyl-OH, —(C$_1$-C$_6$)-alkyl-NH$_2$, —(C$_1$-C$_6$)-alkyl-C(=NH)—NH$_2$, —(C$_1$-C$_6$)-alkyl-NH—C(=NH)—NH$_2$ and —(C$_0$-C$_4$)-alkyl-heterocyclyl, in another embodiment from —(C$_1$-C$_{10}$)-alkyl, —(C$_1$-C$_6$)-alkyl-C(O)—N(R20)-R21, —(C$_1$-C$_4$)-alkyl-C(O)—O—R22, —(C$_1$-C$_6$)-alkyl-OH, —(C$_1$-C$_6$)-alkyl-NH$_2$, —(C$_1$-C$_6$)-alkyl-NH—C(=NH)—NH$_2$ and —(C$_0$-C$_4$)-alkyl-heterocyclyl, in another embodiment from —(C$_1$-C$_{10}$)-alkyl, —(C$_1$-C$_6$)-alkyl-C(O)—N(R20)-R21, —(C$_1$-C$_4$)-alkyl-C(O)—O—R22, —(C$_1$-C$_6$)-alkyl-OH, —(C$_1$-C$_6$)-alkyl-NH$_2$ and —(C$_0$-C$_4$)-alkyl-heterocyclyl, wherein alkyl in —(C$_1$-C$_{10}$)-alkyl is unsubstituted or monosubstituted, disubstituted or trisubstituted independently of one another by halogen and wherein heterocyclyl in —(C$_0$-C$_4$)-alkyl-heterocyclyl is monocyclic or bicyclic and contains 3 to 15 ring carbon atoms, in another embodiment 5 to 10 ring carbon atoms, and wherein one or more of the ring carbon atoms are replaced by 1, 2, 3 or 4 heteroatoms chosen from nitrogen, sulfur and oxygen, and in another embodiment one or two ring carbon atoms are replaced by heteroatoms chosen from nitrogen, sulfur and oxygen, and wherein said heterocyclyl is unsubstituted or monosubstituted, disubstituted or trisubstituted, in another embodiment unsubstituted, monosubstituted or disubstituted, in another embodiment unsubstituted or monosubstituted, independently of one another by R19, or R1 and R2 form together with the atom to which they are attached a ring selected from cyclopropane, cyclobutane, cyclopentane and cyclohexane, in another embodiment from cyclopropane and cyclopentane.

In another embodiment one of R1 and R2, for example R1, is hydrogen or —(C$_1$-C$_4$)-alkyl, in another embodiment hydrogen, and the other, for example R2, is selected from —(C$_1$-C$_{10}$)-alkyl, —(C$_1$-C$_6$)-alkyl-C(O)—N(R20)-R21, —(C$_1$-C$_4$)-alkyl-C(O)—O—R22, —(C$_1$-C$_6$)-alkyl-OH, —(C$_1$-C$_6$)-alkyl-NH$_2$ and —(C$_0$-C$_4$)-alkyl-heterocyclyl, wherein alkyl in —(C$_1$-C$_{10}$)-alkyl is unsubstituted or monosubstituted, disubstituted or trisubstituted independently of one another by halogen, for example fluorine and wherein heterocyclyl in —(C$_0$-C$_4$)-alkyl-heterocyclyl is monocyclic or bicyclic and contains 3 to 15 ring carbon atoms, in another embodiment 5 to 10 ring carbon atoms, and wherein one or more of the ring carbon atoms are replaced by 1, 2, 3 or 4 heteroatoms chosen from nitrogen, sulfur and oxygen, and in another embodiment one or two ring carbon atoms are replaced by heteroatoms chosen from nitrogen, sulfur and oxygen, and wherein said heterocyclyl is unsubstituted, or R1 and R2 form together with the atom to which they are attached a ring selected from cyclopropane, cyclobutane, cyclopentane and cyclohexane, in another embodiment from cyclopropane and cyclopentane.

In one embodiment, —($C_1$-$C_{10}$)-alkyl representing R1 or R2 is —($C_1$-$C_8$)-alkyl, in another embodiment —($C_1$-$C_6$)-alkyl, which are unsubstituted or substituted as indicated, and in another embodiment are unsubstituted. In one embodiment, the group —($C_0$-$C_4$)-alkyl-heterocyclyl representing R1 or R2 is —($C_1$-$C_4$)-alkyl-heterocyclyl, in another embodiment —($C_1$-$C_2$)-alkyl-heterocyclyl, in another embodiment —$CH_2$-heterocyclyl. In one embodiment, heterocyclyl occurring in R1 or R2 is monocyclic or bicyclic, in another embodiment monocyclic, and contains 5 to 10 ring carbon atoms, in another embodiment 5 to 9 ring carbon atoms, wherein one or two of the ring carbon atoms are replaced by nitrogen atoms as ring heteroatoms, and wherein heterocyclyl is aromatic. In one embodiment, heterocyclyl occurring in R1 or R2 is imidazolyl, for example 1H-imidazol-4-yl.

In one embodiment, R1 and R2 together with the carbon atom carrying them and the NH group and the CO group attached to the said carbon atom, form the residue of 1-aminocyclopropane-1-carboxylic acid, 1-aminocyclopentane-1-carboxylic acid, L-asparagine, L-aspartic acid, L-2,3-diaminobutyric acid, L-glutamine, L-histidine, L-leucine, L-serine or L-threonine, or a pharmaceutically acceptable salt or a ($C_1$-$C_4$)-alkyl ester thereof, wherein these residues of amino acids, like the residues of amino acids occurring in respective other positions of the compounds of formula I, are formally obtained by removal of a hydrogen atom and the OH group from the amino group and the CO—OH group, respectively, in the moiety $H_2N$—CH—CO—OH, and are bonded via the resulting —NH group and CO— group in usual peptide manner to the neighboring CO group and NH group, respectively.

In one embodiment, R3 and R4 are independently of one another selected from hydrogen, —($C_1$-$C_{10}$)-alkyl and —($C_1$-$C_4$)-alkyl-C(O)—O—R22. In another embodiment one of R3 and R4, for example R3, is hydrogen and the other, for example R4, is selected from —($C_1$-$C_{10}$)-alkyl and —($C_1$-$C_4$)-alkyl-C(O)—O—R22, wherein alkyl in —($C_1$-$C_{10}$)-alkyl is unsubstituted or monosubstituted, disubstituted or trisubstituted independently of one another by halogen. In another embodiment one of R3 and R4, for example R3, is hydrogen and the other, for example R4, is selected from —($C_1$-$C_4$)-alkyl-C(O)—O—R22, in another embodiment from —$CH_2$—$CH_2$—C(O)—O—R22. In one embodiment, R3 and R4 together with the carbon atom carrying them and the NH group and the CO group attached to the said carbon atom, form the residue of L-glutamic acid or a pharmaceutically acceptable salt or a ($C_1$-$C_4$)-alkyl ester thereof, in another embodiment the residue of L-glutamic acid or a pharmaceutically acceptable salt thereof.

In one embodiment, R5 and R6 are independently of one another selected from hydrogen, —($C_1$-$C_6$)-alkyl-$NH_2$, —($C_1$-$C_6$)-alkyl-C(=NH)—$NH_2$, —($C_1$-$C_6$)-alkyl-NH—C(=NH)—$NH_2$ and —($C_0$-$C_4$)-alkyl-heterocyclyl, wherein heterocyclyl in —($C_0$-$C_4$)-alkyl-heterocyclyl is monocyclic or bicyclic and contains 3 to 15 ring carbon atoms and wherein one or more of the ring carbon atoms are replaced by 1, 2, 3 or 4 heteroatoms chosen from nitrogen, sulfur or oxygen, and wherein said heterocyclyl is unsubstituted or monosubstituted, disubstituted or trisubstituted independently of one another by R19. In another embodiment R5 and R6 are independently selected from hydrogen, —($C_1$-$C_6$)-alkyl-$NH_2$, —($C_1$-$C_6$)-alkyl-NH—C(=NH)—$NH_2$,

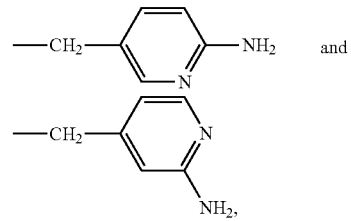

in another embodiment from hydrogen, —($C_1$-$C_6$)-alkyl-$NH_2$ and —($C_1$-$C_6$)-alkyl-NH—C(=NH)—$NH_2$. In another embodiment one of R5 and R6, for example R5, is hydrogen and the other, for example R6, is selected from —($C_1$-$C_6$)-alkyl-$NH_2$, —($C_1$-$C_6$)-alkyl-C(=NH)—$NH_2$, —($C_1$-$C_6$)-alkyl-NH—C(=NH)—$NH_2$,

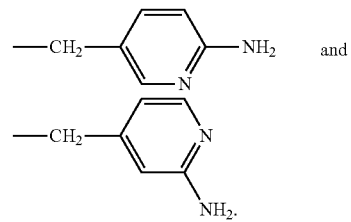

In another embodiment one of R5 and R6, for example R5, is hydrogen and the other, for example R6, is selected from —($C_1$-$C_6$)-alkyl-$NH_2$ and —($C_1$-$C_6$)-alkyl-NH—C(=NH)—$NH_2$, in another embodiment from —($C_1$-$C_6$)-alkyl-NH—C(=NH)—$NH_2$.

In one embodiment, R5 and R6 together with the carbon atom carrying them and the NH group and the CO group attached to the said carbon atom, form the residue of L-arginine, L-2,3-diaminopropionic acid, L-lysine or L-ornithine, or a pharmaceutically acceptable salt thereof.

In one embodiment, R7 and R8 are independently of one another selected from hydrogen, —($C_1$-$C_{10}$)-alkyl, —($C_1$-$C_6$)-alkyl-C(O)—N(R20)-R21, —($C_1$-$C_6$)-alkyl-O—R23, —($C_1$-$C_6$)-alkyl-S—R24, —($C_0$-$C_4$)-alkyl-($C_3$-$C_8$)-cycloalkyl and —($C_0$-$C_4$)-alkyl-($C_6$-$C_{14}$)-aryl, in another embodiment from hydrogen, —($C_1$-$C_{10}$)-alkyl, —($C_1$-$C_6$)-alkyl-O—R23, —($C_1$-$C_6$)-alkyl-S—R24, —($C_0$-$C_4$)-alkyl-($C_3$-$C_8$)-cycloalkyl and —($C_0$-$C_4$)-alkyl-($C_6$-$C_{14}$)-aryl, in another embodiment from hydrogen, —($C_1$-$C_{10}$)-alkyl, —($C_1$-$C_6$)-alkyl-O—R23, —($C_1$-$C_6$)-alkyl-S—R24, —($C_0$-$C_4$)-alkyl-($C_3$-$C_8$)-cycloalkyl, in another embodiment from —($C_1$-$C_{10}$)-alkyl, —($C_1$-$C_6$)-alkyl-C(O)—N(R20)-R21, —($C_1$-$C_6$)-alkyl-O—R23, —($C_1$-$C_6$)-alkyl-S—R24 and —($C_0$-$C_4$)-alkyl-($C_3$-$C_8$)-cycloalkyl, in another embodiment from —($C_1$-$C_{10}$)-alkyl, —($C_1$-$C_6$)-alkyl-O—R23, —($C_1$-$C_6$)-alkyl-S—R24 and —($C_0$-$C_4$)-alkyl-($C_3$-$C_8$)-cycloalkyl, wherein alkyl in —($C_1$-$C_{10}$)-alkyl is unsubstituted or monosubstituted, disubstituted or trisubstituted independently of one another by halogen and wherein aryl in —($C_0$-$C_4$)-alkyl-($C_6$-$C_{14}$)-aryl is unsubstituted or monosubstituted, disubstituted or trisubstituted independently of one another by R19.

In another embodiment one of R7 and R8, for example R7, is hydrogen and the other, for example R8, is selected from hydrogen, —($C_1$-$C_{10}$)-alkyl, —($C_1$-$C_6$)-alkyl-C(O)—N(R20)-R21, —($C_1$-$C_6$)-alkyl-O—R23, —($C_1$-$C_6$)-alkyl-S—R24, —($C_0$-$C_4$)-alkyl-($C_3$-$C_8$)-cycloalkyl and —($C_0$-$C_4$)-alkyl-($C_6$-$C_{14}$)-aryl, in another embodiment from hydrogen, —($C_1$-$C_{10}$)-alkyl, —($C_1$-$C_6$)-alkyl-O—R23, —($C_1$-$C_6$)- alkyl-S—R24, —($C_0$-$C_4$)-alkyl-($C_3$-$C_8$)-cycloalkyl and —($C_0$-$C_4$)-alkyl-($C_6$-$C_{14}$)-aryl, in another embodiment from hydrogen, —($C_1$-$C_{10}$)-alkyl, —($C_1$-$C_6$)-alkyl-O—R23, —($C_1$-$C_6$)-alkyl-S—R24, —($C_0$-$C_4$)-alkyl-($C_3$-$C_8$)-cycloalkyl, in another embodiment from —($C_1$-$C_{10}$)-alkyl, —($C_1$-$C_6$)-alkyl-C(O)—N(R20)-R21, —($C_1$-$C_6$)-alkyl-O—R23, —($C_1$-$C_6$)-alkyl-S—R24 and —($C_0$-$C_4$)-alkyl-($C_3$-$C_8$)-cycloalkyl, in another embodiment from —($C_1$-$C_{10}$)-alkyl, —($C_1$-$C_6$)-alkyl-O—R23, —($C_1$-$C_6$)-alkyl-S—R24 and —($C_0$-$C_4$)-alkyl-($C_3$-$C_8$)-cycloalkyl, wherein alkyl in —($C_1$-$C_{10}$)-alkyl is unsubstituted or monosubstituted, disubstituted or trisubstituted independently of one another by halogen, for example fluorine, and wherein aryl in —($C_0$-$C_4$)-alkyl-($C_6$-$C_{14}$)-aryl is unsubstituted or monosubstituted, disubstituted or trisubstituted independently of one another by R19.

In one embodiment, —($C_1$-$C_{10}$)-alkyl representing R7 or R8 is —($C_1$-$C_8$)-alkyl, in another embodiment —($C_1$-$C_6$)-alkyl. In one embodiment, ($C_3$-$C_8$)-cycloalkyl occurring in R7 or R8 is ($C_3$-$C_7$)-cycloalkyl, in another embodiment ($C_5$-$C_7$)-cycloalkyl, in another embodiment ($C_5$-$C_6$)-cycloalkyl, in another embodiment cyclohexyl. In one embodiment, aryl occurring in R7 or R8 is phenyl.

In one embodiment, R7 and R8 together with the carbon atom carrying them and the NH group and the CO group attached to the said carbon atom, form the residue of L-alanine, L-2-aminobutyric acid, L-2-amino-4-methoxybutyric acid, L-2-amino-3-methoxypropionic acid, L-cyclohexylalanine, L-cyclohexylglycine, L-glutamine, L-isoleucine, L-leucine, L-methionine or L-norleucine.

In one embodiment, R9 and R10 are independently of one another selected from hydrogen, —($C_1$-$C_{10}$)-alkyl, —($C_1$-$C_6$)-alkyl-C(O)—N(R20)-R21, —($C_1$-$C_4$)-alkyl-C(O)—O——R22, —($C_1$-$C_6$)-alkyl-O—R23, —($C_1$-$C_6$)-alkyl-S—R24, —($C_1$-$C_6$)-alkyl-$NH_2$, —($C_1$-$C_6$)-alkyl-NH—C(=NH)—$NH_2$ and —($C_0$-$C_4$)-alkyl-($C_3$-$C_8$)-cycloalkyl, in another embodiment from hydrogen, —($C_1$-$C_{10}$)-alkyl, —($C_1$-$C_6$)-alkyl-C(O)—N(R20)-R21, —($C_1$-$C_4$)-alkyl-C(O)—O—R22, —($C_1$-$C_6$)-alkyl-O—R23, —($C_1$-$C_6$)-alkyl-S—R24, —($C_1$-$C_6$)-alkyl-$NH_2$ and —($C_0$-$C_4$)-alkyl-($C_3$-$C_8$)-cycloalkyl, in another embodiment from hydrogen, —($C_1$-$C_{10}$)-alkyl, —($C_1$-$C_6$)-alkyl-C(O)—N(R20)-R21, —($C_1$-$C_6$)-alkyl-$NH_2$, —($C_1$-$C_6$)-alkyl-NH—C(=NH)—$NH_2$ and —($C_0$-$C_4$)-alkyl-($C_3$-$C_8$)-cycloalkyl, in another embodiment from hydrogen, —($C_1$-$C_{10}$)-alkyl, —($C_1$-$C_6$)-alkyl-C(O)—N(R20)-R21, —($C_1$-$C_6$)-alkyl-$NH_2$ and —($C_1$-$C_6$)-alkyl-NH—C(=NH)—$NH_2$, in another embodiment from hydrogen, —($C_1$-$C_{10}$)-alkyl, —($C_1$-$C_6$)-alkyl-C(O)—N(R20)-R21 and —($C_1$-$C_6$)-alkyl-$NH_2$, wherein alkyl in —($C_1$-$C_{10}$)-alkyl is unsubstituted or monosubstituted, disubstituted or trisubstituted independently of one another by halogen.

In another embodiment one of R9 and R10, for example R9, is hydrogen and the other, for example R10, is selected from hydrogen, —($C_1$-$C_{10}$)-alkyl, —($C_1$-$C_6$)-alkyl-C(O)—N(R20)-R21, —($C_1$-$C_4$)-alkyl-C(O)—O—R22, —($C_1$-$C_6$)-alkyl-O—R23, —($C_1$-$C_6$)-alkyl-S—R24, —($C_1$-$C_6$)-alkyl-$NH_2$, —($C_1$-$C_6$)-alkyl-NH—C(=NH)—$NH_2$ and —($C_0$-$C_4$)-alkyl-($C_3$-$C_8$)-cycloalkyl, in another embodiment from hydrogen, —($C_1$-$C_{10}$)-alkyl, —($C_1$-$C_6$)-alkyl-C(O)—N(R20)-R21, —($C_1$-$C_4$)-alkyl-C(O)—O—R22, R24, —($C_1$-$C_6$)-alkyl-$NH_2$ and —($C_0$-$C_4$)-alkyl-($C_3$-$C_8$)-cycloalkyl, in another embodiment from hydrogen, —($C_1$-$C_{10}$)-alkyl, —($C_1$-$C_6$)-alkyl-C(O)—N(R20)-R21, —($C_1$-$C_6$)-alkyl-$NH_2$, —($C_1$-$C_6$)-alkyl-NH—C(=NH)—$NH_2$ and —($C_0$-$C_4$)-alkyl-($C_3$-$C_8$)-cycloalkyl, in another embodiment from hydrogen, —($C_1$-$C_{10}$)-alkyl, —($C_1$-$C_6$)-alkyl-C(O)—N(R20)-R21, —($C_1$-$C_6$)-alkyl-$NH_2$ and —($C_1$-$C_6$)-alkyl-NH—C(=NH)—$NH_2$, in another embodiment from hydrogen, —($C_1$-$C_{10}$)-alkyl, —($C_1$-$C_6$)-alkyl-C(O)—N(R20)-R21 and —($C_1$-$C_6$)-alkyl-$NH_2$, wherein alkyl in —($C_1$-$C_{10}$)-alkyl is unsubstituted or monosubstituted, disubstituted or trisubstituted independently of one another by halogen. In another embodiment one of R9 and R10, for example R9, is hydrogen and the other, for example R10, is selected from —($C_1$-$C_{10}$)-alkyl and —($C_0$-$C_4$)-alkyl-($C_3$-$C_8$)-cycloalkyl. In another embodiment one of R9 and R10, for example R9, is hydrogen and the other, for example R10, is selected from —($C_1$-$C_{10}$)-alkyl, in another embodiment from —($C_1$-$C_6$)-alkyl, in another embodiment from —($C_1$-$C_4$)-alkyl.

In one embodiment, R9 and R10 together with the carbon atom carrying them and the NH group and the CO group attached to the said carbon atom, form the residue of L-alanine, L-arginine, L-2,3-diaminopropionic acid, L-glutamine or L-norvaline, or a pharmaceutically acceptable salt thereof;

In one embodiment, R11, R12, R17 and R18 are independently of one another selected from hydrogen, —($C_1$-$C_{10}$)-alkyl, —($C_0$-$C_4$)-alkyl-($C_3$-$C_8$)-cycloalkyl and —($C_0$-$C_4$)-alkyl-($C_6$-$C_{14}$)-aryl, wherein alkyl in —($C_1$-$C_{10}$)-alkyl is unsubstituted or monosubstituted, disubstituted or trisubstituted independently of one another by halogen and wherein aryl in —($C_0$-$C_4$)-alkyl-($C_6$-$C_{14}$)-aryl is unsubstituted or monosubstituted, disubstituted or trisubstituted independently of one another by R19, or R11 and R12 or R17 and R18 form together with the atoms to which they are attached a ring selected from cyclopropane, cyclobutane, cyclopentane, cyclohexane and cycloheptane.

In one embodiment, R11 and R12 are independently of one another selected from hydrogen, —($C_1$-$C_{10}$)-alkyl, —($C_0$-$C_4$)-alkyl-($C_3$-$C_8$)-cycloalkyl and —($C_0$-$C_4$)-alkyl-($C_6$-$C_{14}$)-aryl, wherein alkyl in —($C_1$-$C_{10}$)-alkyl is unsubstituted or monosubstituted, disubstituted or trisubstituted independently of one another by halogen and wherein aryl is unsubstituted, or R11 and R12 form together with the atom to which they are attached a ring selected from cyclopropane, cyclobutane, cyclopentane, cyclohexane and cycloheptane. In another embodiment one of R11 and R12, for example R11, is selected from hydrogen and ($C_1$-$C_4$)-alkyl, and in another embodiment is hydrogen, and the other, for example R12, is selected from —($C_1$-$C_{10}$)-alkyl, —($C_0$-$C_4$)-alkyl-($C_3$-$C_8$)-cycloalkyl and —($C_0$-$C_4$)-alkyl-($C_6$-$C_{14}$)-aryl, in another embodiment from —($C_1$-$C_{10}$)-alkyl and —($C_0$-$C_4$)-alkyl-($C_3$-$C_8$)-cycloalkyl, wherein alkyl in —($C_1$-$C_{10}$)-alkyl is unsubstituted or monosubstituted, disubstituted or trisubstituted independently of one another by halogen and wherein aryl is unsubstituted, or R11 and R12 form together with the atom to which they are attached a ring selected from cyclopropane, cyclobutane, cyclopentane, cyclohexane and cycloheptane. In another embodiment one of R11 and R12, for example R11, is selected from hydrogen and ($C_1$-$C_4$)-alkyl, and in another embodiment is hydrogen, and the other, for example R12, is selected from —($C_1$-$C_{10}$)-alkyl and —($C_0$-$C_4$)-alkyl-($C_3$-$C_8$)-cycloalkyl, wherein alkyl in —($C_1$-$C_{10}$)-alkyl is unsubstituted or monosubstituted, disubstituted or trisubstituted independently of one another by halogen, for example by fluorine. In one embodiment, —($C_1$-$C_{10}$)-alkyl representing R11 or R12 is —($C_1$-$C_8$)-alkyl, in another embodiment —($C_1$-$C_6$)-alkyl. In one embodiment, ($C_3$-$C_8$)-cycloalkyl occurring in R11 or R12 is ($C_3$-$C_7$)-cycloalkyl, in another embodiment ($C_5$-$C_7$)-cycloalkyl, in another embodiment ($C_5$-$C_6$)-cycloalkyl, in another embodiment cyclohexyl. In one embodiment, a ring formed by R11 and R12 together with the atom to which they are attached, is selected from cyclopentane, cyclohexane and cycloheptane, in another embodiment from cyclopentane and cyclohexane, in another embodiment it is cyclohexane. In one embodiment, aryl occurring in R11 or R12 is phenyl.

In one embodiment, R11 and R12 together with the carbon atom carrying them and the NH group and the CO group attached to the said carbon atom, form the residue of 1-aminocyclohexane-1-carboxylic acid, L-cyclohexylalanine, L-cyclohexylglycine, L-isoleucine, L-leucine, L-neopentylglycine, L-norleucine or L-norvaline;

In one embodiment, R13, R14, R15 and R16 are independently of one another selected from hydrogen, —($C_1$-$C_{10}$)-alkyl, —($C_1$-$C_6$)-alkyl-C(O)—N(R20)-R21, —($C_1$-$C_4$)-alkyl-C(O)—O—R22, —($C_1$-$C_6$)-alkyl-NH$_2$ and —($C_0$-$C_4$)-alkyl-heterocyclyl, wherein alkyl in —($C_1$-$C_{10}$)-alkyl is unsubstituted or monosubstituted, disubstituted or trisubstituted independently of one another by halogen and wherein heterocyclyl in —($C_0$-$C_4$)-alkyl-heterocyclyl is monocyclic or bicyclic and contains 3 to 15 ring carbon atoms and wherein one or more of the ring carbon atoms are replaced by 1, 2, 3 or 4 heteroatoms chosen from nitrogen, sulfur and oxygen, and wherein said heterocyclyl is unsubstituted or monosubstituted, disubstituted or trisubstituted independently of one another by R19.

In one embodiment, R13 and R14 are independently of one another selected from hydrogen, —($C_1$-$C_{10}$)-alkyl, —($C_1$-$C_6$)-alkyl-C(O)—N(R20)-R21, —($C_1$-$C_4$)-alkyl-C(O)—O—R22 and —($C_0$-$C_4$)-alkyl-heterocyclyl, in another embodiment from hydrogen, —($C_1$-$C_{10}$)-alkyl, —($C_1$-$C_6$)-alkyl-C(O)—NH$_2$, —($C_1$-$C_4$)-alkyl-C(O)—OH and —($C_0$-$C_4$)-alkyl-heterocyclyl, in another embodiment from hydrogen, —($C_1$-$C_{10}$)-alkyl, —($C_1$-$C_4$)-alkyl-C(O)—O—R22 and —($C_0$-$C_4$)-alkyl-heterocyclyl, wherein alkyl in —($C_1$-$C_{10}$)-alkyl is unsubstituted or monosubstituted, disubstituted or trisubstituted independently of one another by halogen and wherein heterocyclyl in —($C_0$-$C_4$)-alkyl-heterocyclyl is monocyclic or bicyclic and contains 3 to 15 ring carbon atoms and wherein one or more of the ring carbon atoms are replaced by 1, 2, 3 or 4 heteroatoms chosen from nitrogen, sulfur and oxygen, and wherein said heterocyclyl is unsubstituted or monosubstituted, disubstituted or trisubstituted independently of one another by R19.

In another embodiment one of R13 and R14, for example R13, is hydrogen and the other, for example R14, is selected from hydrogen, —($C_1$-$C_{10}$)-alkyl, —($C_1$-$C_6$)-alkyl-C(O)—N(R20)-R21, —($C_1$-$C_4$)-alkyl-C(O)—O—R22 and —($C_0$-$C_4$)-alkyl-heterocyclyl, in another embodiment from —($C_1$-$C_{10}$)-alkyl, —($C_1$-$C_6$)-alkyl-C(O)—NH$_2$, —($C_1$-$C_4$)-alkyl-C(O)—OH and —($C_0$-$C_4$)-alkyl-heterocyclyl, in another embodiment from hydrogen, —($C_1$-$C_{10}$)-alkyl, —($C_1$-$C_4$)-alkyl-C(O)—O—R22 and —($C_0$-$C_4$)-alkyl-heterocyclyl, in another embodiment from —($C_1$-$C_4$)-alkyl-C(O)—O—R22 and —($C_0$-$C_4$)-alkyl-heterocyclyl, in another embodiment from —($C_1$-$C_4$)-alkyl-C(O)—OH and —($C_0$-$C_4$)-alkyl-heterocyclyl, in another embodiment from —($C_1$-$C_4$)-alkyl-C(O)—OH, —($C_1$-$C_6$)-alkyl-NH$_2$ and —($C_0$-$C_4$)-alkyl-heterocyclyl, in another embodiment from —($C_1$-$C_4$)-alkyl-C(O)—OH, —($C_1$-$C_4$)-alkyl-NH$_2$ and —($C_0$-$C_4$)-alkyl-heterocyclyl, and in another embodiment is —($C_0$-$C_4$)-alkyl-heterocyclyl, wherein alkyl in —($C_1$-$C_{10}$)-alkyl is unsubstituted or monosubstituted, disubstituted or trisubstituted independently of one another by halogen, for example by fluorine, and wherein heterocyclyl in —($C_0$-$C_4$)-alkyl-heterocyclyl is monocyclic or bicyclic and contains 3 to 15 ring carbon atoms, in another embodiment 5 to 10 ring carbon atoms, and wherein one or more of the ring carbon atoms are replaced by 1, 2, 3 or 4 heteroatoms chosen from nitrogen, sulfur and oxygen, and in another embodiment one or two ring carbon atoms are replaced by heteroatoms chosen from nitrogen, sulfur and oxygen, and wherein said heterocyclyl is unsubstituted or monosubstituted, disubstituted or trisubstituted, in another embodiment unsubstituted or monosubstituted, independently of one another by R19.

In one embodiment, —($C_1$-$C_{10}$)-alkyl representing R13 or R14 is —($C_1$-$C_8$)-alkyl, in another embodiment —($C_1$-$C_6$)-alkyl, which are unsubstituted or substituted as indicated, and in another embodiment are unsubstituted. In one embodiment, the group —($C_0$-$C_4$)-alkyl-heterocyclyl representing R13 or R14 is —($C_1$-$C_4$)-alkyl-heterocyclyl, in another embodiment —($C_1$-$C_2$)-alkyl-heterocyclyl, in another embodiment —CH$_2$-heterocyclyl. In one embodiment, heterocyclyl occurring in R13 or R14 is monocyclic or bicyclic, in another embodiment monocyclic, and contains 5 to 10 ring carbon atoms, in another embodiment 5 to 9 ring carbon atoms, wherein one or two of the ring carbon atoms are replaced by nitrogen atoms as ring heteroatoms, and wherein heterocyclyl is aromatic. In one embodiment, heterocyclyl occurring in R13 or R14 is selected from imidazolyl and indolyl, for example 1H-imidazol-4-yl and 1H-indol-3-yl, respectively, and in another embodiment is imidazolyl, for example 1H-imidazol-4-yl. In one embodiment, one of R13 and R14, for example R13, is hydrogen and the other, for example R14, is selected from —CH$_2$-imidazolyl and —CH$_2$-indolyl, and in another embodiment is —CH$_2$-imidazolyl, wherein imidazolyl is unsubstituted or monosubstituted or disubstituted independently of one another by R19 and wherein indolyl is unsubstituted or monosubstituted, disubstituted or trisubstituted independently of one another by R19.

In one embodiment, R13 and R14 together with the carbon atom carrying them and the NH group and the CO group attached to the said carbon atom, form the residue of L-histidine, D-histidine, L-ornithine or D-aspartic acid, or a pharmaceutically acceptable salt or a ($C_1$-$C_4$)-alkyl ester thereof;

In one embodiment, R15 and R16 are independently of one another selected from hydrogen, —($C_1$-$C_{10}$)-alkyl, —($C_1$-$C_6$)-alkyl-C(O)—N(R20)-R21 and —($C_1$-$C_4$)-alkyl-C(O)—O—R22, in another embodiment from hydrogen, —($C_1$-$C_{10}$)-alkyl, —($C_1$-$C_6$)-alkyl-C(O)—NH$_2$ and —($C_1$-$C_4$)-alkyl-C(O)—OH, wherein alkyl in —($C_1$-$C_{10}$)-alkyl is unsubstituted or monosubstituted, disubstituted or trisubstituted independently of one another by halogen. In another embodiment one of R15 and R16, for example R15, is hydrogen and the other, for example R16, is selected from —($C_1$-$C_{10}$)-alkyl, —($C_1$-$C_6$)-alkyl-C(O)—N(R20)-R21 and —($C_1$-$C_4$)-alkyl-C(O)—O—R22, in another embodiment from —($C_1$-$C_6$)-alkyl-C(O)—N(R20)-R21 and —($C_1$-$C_4$)-alkyl-C(O)—O—R22, in another embodiment from —($C_1$-$C_{10}$)-alkyl, —($C_1$-$C_6$)-alkyl-C(O)—NH$_2$ and —($C_1$-$C_4$)-alkyl-C(O)—OH, in another embodiment from —($C_1$-$C_6$)-alkyl-C(O)—NH$_2$ and —($C_1$-$C_4$)-alkyl-C(O)—OH, wherein alkyl in —($C_1$-$C_{10}$)-alkyl is unsubstituted or monosubstituted, disubstituted or trisubstituted independently of one another by halogen, for example fluorine.

In another embodiment one of R15 and R16, for example R15, is hydrogen and the other, for example R16, is selected from —($C_1$-$C_6$)-alkyl-C(O)—N(R20)-R21, in another embodiment from —($C_1$-$C_4$)-alkyl-C(O)—N(R20)-R21, in another embodiment from —CH$_2$—CH$_2$—C(O)—N(R20)-R21, in another embodiment from —($C_1$-$C_6$)-alkyl-C(O)—NH$_2$, in another embodiment from —($C_1$-$C_4$)-alkyl-C(O)—NH$_2$, and in another embodiment is —CH$_2$—CH$_2$—C(O)—NH$_2$. In one embodiment, R3 and R4 together with the carbon atom carrying them and the NH group and the CO group attached to the said carbon atom, form the residue of L-asparagine.

In one embodiment, R17 and R18 are independently of one another selected from hydrogen, —($C_1$-$C_{10}$)-alkyl, —($C_0$-$C_4$)-alkyl-($C_3$-$C_8$)-cycloalkyl and —($C_0$-$C_4$)-alkyl-($C_6$-$C_{14}$)-aryl, wherein alkyl in —($C_1$-$C_{10}$)-alkyl is unsubstituted or monosubstituted, disubstituted or trisubstituted independently of one another by halogen and wherein aryl in —($C_0$-$C_4$)-alkyl-($C_6$-$C_{14}$)-aryl is unsubstituted, or R17 and R18 form together with the atom to which they are attached a ring selected from cyclopropane, cyclobutane, cyclopentane, cyclohexane and cycloheptane. In another embodiment, one of R17 and R18, for example R17, is hydrogen and the other, for example R18, is selected from —($C_1$-$C_{10}$)-alkyl, —($C_0$-$C_4$)-alkyl-($C_3$-$C_8$)-cycloalkyl and —($C_0$-$C_4$)-alkyl-($C_6$-$C_{14}$)-aryl, wherein alkyl in —($C_1$-$C_{10}$)-alkyl is unsubstituted or monosubstituted, disubstituted or trisubstituted independently of one another by halogen and wherein aryl in —($C_0$-$C_4$)-alkyl-($C_6$-$C_{14}$)-aryl is unsubstituted, or R17 and R18 form together with the atom to which they are attached a ring selected from cyclopropane, cyclobutane, cyclopentane, cyclohexane and cycloheptane. In another embodiment, one of R17 and R18, for example R17, is hydrogen and the other is selected from —($C_1$-$C_{10}$)-alkyl and —($C_0$-$C_4$)-alkyl-($C_3$-$C_8$)-cycloalkyl, wherein alkyl in —($C_1$-$C_{10}$)-alkyl is unsubstituted or monosubstituted, disubstituted or trisubstituted independently of one another by halogen, or R17 and R18 form together with the atoms to which they are attached a ring selected from cyclopropane and cyclopentane. In another embodiment, one of R17 and R18, for example R17, is hydrogen and the other is selected from —($C_1$-$C_{10}$)-alkyl, wherein alkyl in —($C_1$-$C_{10}$)-alkyl is unsubstituted or monosubstituted, disubstituted or trisubstituted independently of one another by halogen, for example fluorine, and in another embodiment is unsubstituted.

In one embodiment, —($C_1$-$C_{10}$)-alkyl representing R17 or R18 is —($C_1$-$C_8$)-alkyl, in another embodiment —($C_1$-$C_6$)-alkyl. In one embodiment, ($C_3$-$C_8$)-cycloalkyl occurring in R17 or R18 is ($C_3$-$C_7$)-cycloalkyl, in another embodiment ($C_5$-$C_7$)-cycloalkyl, in another embodiment ($C_3$-$C_6$)-cyclopropyl, in another embodiment ($C_5$-$C_6$)-cycloalkyl. In one embodiment, aryl occurring in R17 or R88 is phenyl. In one embodiment, R17 and R18 together with the carbon atom carrying them and the NH group and the CO group attached to the said carbon atom, form the residue of L-leucine.

In one embodiment, R19 is halogen, amino, cyano, —($C_1$-$C_4$)-alkoxy, hydroxyl or —($C_1$-$C_6$)-alkyl, in another embodiment halogen, —($C_1$-$C_4$)-alkoxy or —($C_1$-$C_4$)-alkyl, in another embodiment halogen or —($C_1$-$C_4$)-alkyl, in another embodiment halogen, in another embodiment halogen, amino, methoxy, hydroxyl or methyl, wherein the definitions of all groups R19 are independent of one another.

In one embodiment, R20, R21, R22, R23 and R24 are independently of one another selected from hydrogen and ($C_1$-$C_6$)-alkyl, in another embodiment from hydrogen and ($C_1$-$C_4$)-alkyl, in another embodiment from hydrogen and ($C_1$-$C_3$)-alkyl, in another embodiment from hydrogen and methyl, and in another embodiment are hydrogen, in another embodiment are ($C_1$-$C_4$)-alkyl, in another embodiment are ($C_1$-$C_3$)-alkyl, and in another embodiment are methyl, wherein the definitions of all groups R20, R21, R22, R23 and R24 are independent of each other.

A subject of the invention are all compounds of the formula I wherein any one or more structural elements such as groups, residues, substituents and numbers are defined as in any of the specified embodiments or definitions of the elements, or have one or more of the specific meanings which are mentioned herein as examples of elements, wherein all combinations of one or more definitions of compounds or elements and/or specified embodiments and/or specific meanings of elements are a subject of the present invention.

In general, the meaning of any group, residue, heteroatom, number, etc., which can occur more than once in the compounds of the formula I, is independent of the meaning of this group, residue, heteroatom, number etc. in any other occurrence. All groups, residues, heteroatoms, numbers etc., which can occur more than once in the compounds of the formula I can be identical or different.

Alkyl residues may be straight-chain or branched. This applies also when they carry substituents, for example hydroxyl residues, or occur as substituents of other residues, for example in alkylamino residues or alkoxy residues. Examples of alkyl residues are methyl, ethyl, n-propyl, isopropyl (=1-methylethyl), n-butyl, isobutyl (=2-methylpropyl), sec-butyl (=1-methylpropyl), tert-butyl (=1,1-dimethylethyl), n-pentyl, isopentyl, tert-pentyl, neopentyl and hexyl. In one embodiment, alkyl residues are methyl, ethyl, n-propyl, isopropyl, n-butyl, isobutyl, sec-butyl and tert-butyl. Unless stated otherwise, one or more, for example 1, 2, 3, 4, 5, 6, 7, 8, 9, 10, 11, 12, 13 or 14, hydrogen atoms in alkyl residues may be substituted by fluorine atoms. Examples of such fluoroalkyl residues are trifluoromethyl, 2,2,2-trifluoroethyl, pentafluoroethyl, heptafluoroisopropyl. Substituted alkyl residues may be substituted in any positions. In one embodiment, alkyl which is unsubstituted or monosubstituted, disubstituted or trisubstituted by halogen is, independently of any other alkyl, alkyl which unsubstituted or monosubstituted, disubstituted or trisubstituted by fluorine. The term alkyl as used herein comprises monovalent alkyl groups and divalent alkyl groups, which latter groups can also be designated as alkanediyl groups or alkylene groups or for which the two valences may be indicated by two hyphens, such as in —($C_1$-$C_8$)-alkyl-, for example. But since it is evident from the circumstances of a specific case whether an alkyl group, or any other group occurring in the compounds of the formula I, is a monovalent group or a divalent group, such an express indication of the valence or a particular designation is not needed. The term $C_0$, which occurs in groups such ($C_0$-$C_8$)-alkyl, for example, denotes a covalent bond, i.e. a single bond, linking the two adjacent groups. Thus, in the case of the group ($C_0$-$C_8$)-alkyl occurring in a denotation of X2-X3, for example, the two groups bonded to ($C_0$-$C_8$)-alkyl are liked to one another by a covalent bond of by a divalent ($C_1$-$C_8$)-alkyl group.

Examples of cycloalkyl residues are cyclopropyl, cyclobutyl, cyclopentyl, cyclohexyl and cycloheptyl. In cycloalkyl residues, one or more, for example 1, 2, 3, 4, 5, 6, 7, 8, 9, 10, 11 or 12, hydrogen atoms may be substituted by fluorine atoms. Substituted cycloalkyl residues may be substituted in any positions. Cycloalkyl residues may also be present in branched form as alkylcycloalkyl or cycloalkylalkyl, for example methylcyclohexyl or cyclohexylmethyl.

The term aryl refers to a monocyclic or polycyclic, for example monocyclic or bicyclic, hydrocarbon residue in which at least one carbocyclic ring is present that has a conjugated pi electron system. In a ($C_6$-$C_{14}$)-aryl group, i.e. a 6-membered to 14-membered aryl group, from 6 to 14 ring carbon atoms are present. Examples of ($C_6$-$C_{14}$)-aryl groups are phenyl, naphthyl, biphenylyl, fluorenyl or anthracenyl. In one embodiment, aryl groups are ($C_6$-$C_{10}$)-aryl, such as phenyl or naphthyl, in another embodiment phenyl. Aryl groups can be bonded via any desired position, and in substituted aryl groups the substituents can be located in any desired position. In monosubstituted phenyl groups the substituent can be located in the 2-position, the 3-position or the 4-position. If a phenyl group carries two substituents, they can be located in 2,3-position, 2,4-position, 2,5-position, 2,6-position, 3,4-position or 3,5-position. In phenyl groups carrying three substituents the substituents can be located in 2,3,4-position, 2,3,5-position, 2,3,6-position, 2,4,5-position, 2,4,6-position, or 3,4,5-position. Naphthyl groups can be 1-naphthyl and 2-naphthyl. In substituted naphthyl groups the substituents can be located in any positions, for example in monosubstituted 1-naphthyl groups in the 2-, 3-, 4-, 5-, 6-, 7-, or 8-position and in monosubstituted 2-naphthyl groups in the 1-, 3-, 4-, 5-, 6-, 7-, or 8-position. Biphenylyl groups can be biphenyl-2-yl, biphenyl-3-yl or biphenyl-4-yl. Fluorenyl groups can be bonded via the 1-, 2-, 3-, 4- or 9-position. In monosubstituted fluorenyl groups bonded via the 9-position the substituent is preferably present in the 1-, 2-, 3- or 4-position. The above statements relating to aryl groups correspondingly apply to divalent groups derived from aryl groups, which may also be designated as arylene groups, for example phenylene which can be unsubstituted or substituted 1,2-phenylene, 1,3-phenylene or 1,4-phenylene, or naphthylene which can be unsubstituted or substituted 1,2-naphthalenediyl, 1,3-naphthalenediyl, 1,4-naphthalenediyl, 1,5-naphthalenediyl, 1,6-naphthalenediyl, 1,7-naphthalenediyl, 1,8-naphthalenediyl, 2,3-naphthalenediyl, 2,6-naphthalenediyl or 2,7-naphthalenediyl.

The terms heterocyclyl refer to saturated or partially unsaturated or aromatic heterocycles, which can be monocyclic or polycyclic, for example monocyclic or bicyclic, and in which one or more of the 3 to 15 ring carbon atoms are replaced by 1, 2, 3 or 4 heteroatoms chosen from nitrogen, oxygen or sulfur, and in one embodiment 1, 2, 3 or 4, in another embodiment 1, 2 or 3, in another embodiment 1 or 2, in another embodiment 1, of the ring carbon atoms are replaced with heteroatoms which are independently of one another chosen from nitrogen, oxygen and sulfur, where all occurrences of heterocyclyl groups in the compounds of the formula are independent of each other. Examples of heterocyclyl groups are acridinyl, 8-aza-bicyclo[3.2.1]oct-3-yl, azaindole (1H-pyrrolopyridinyl), azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benzisoxazolyl, benzisothiazolyl, carbazolyl, 4aH-carbazolyl, carbolinyl, chromanyl, chromenyl, cinnolinyl, decahydrochinolinyl, 2,3-dihydrobenzo[1,4]dioxinyl, 3,4-dihydro-2H-benzo[1,4]oxazinyl, 4,5-dihydro-1,3-oxazolyl, dihydropyridine, 4,5-dihydro-1,3-thiazolyl, dioxazolyl, dioxazinyl, 1,3-dioxolanyl, 1,3-dioxolenyl, 3,3-dioxo[1,3,4]oxathiazinyl, 6H-1,5,2-dithiazinyl, dihydrofuro[2,3-b]-tetrahydrofuranyl, furanyl, furazanyl, imidazolidinyl, imidazolinyl, 2-imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl (perhydro-1,4-oxazinyl), naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, 1,3-oxazolidinyl, oxazolinyl, oxazolyl, oxetanyl, oxocanyl, perhydroazepinyl, perhydro-1,4-dioxanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, 1,2,3,4-tetrahydroisoquinolinyl, tetrahydroquinolinyl, 1,2,3,4-tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, 1,3-thiazolidinyl, thiazolinyl, thienyl, thietanyl, thienothiazolyl, thienooxazolyl, thienoimidazolyl, thietanyl, thiomorpholinyl (perhydro-1,4-thiazinyl), thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl, xanthenyl. In one embodiment heterocyclyl is selected from imidazolyl, pyridinyl and indolyl, in another embodiment from imidazolyl and pyridinyl, in another embodiment from imidazolyl and indolyl, and in another embodiment it is imidazolyl.

The heterocyclyl group may be bonded via any ring carbon atom, and in the case of nitrogen heterocycles via any suitable ring nitrogen atom, if applicable. Thus, for example, a pyrrolyl group can be pyrrol-1-yl, pyrrol-2-yl or pyrrol-3-yl, a pyrrolidinyl group can be pyrrolidin-1-yl (=pyrrolidino), pyrrolidin-2-yl or pyrrolidin-3-yl, a pyridinyl group can be pyridin-2-yl, pyridin-3-yl or pyridin-4-yl, a piperidinyl group can be piperidin-1-yl (=piperidino), piperidin-2-yl, piperidin-3-yl or piperidin-3-yl. Furyl can be furan-2-yl or fur-3-yl, thienyl can be thiophen-2-yl or thiophen-3-yl, imidazolyl can be imidazol-1-yl, imidazol-2-yl, imidazol-4-yl or imidazol-5-yl, 1,3-oxazolylcan be 1,3-oxazol-2-yl, 1,3-oxazol-4-yl or 1,3-oxazol-5-yl, 1,3-thiazolyl can be 1,3-thiazol-2-yl, 1,3-thiazol-4-yl or 1,3-thiazol-5-yl, pyrimidinyl can be pyrimidin-2-yl, pyrimidin-4-yl (=pyrimidin-6-yl) or pyrimidin-5-yl, piperazinyl can be piperazin-1-yl (=piperazin-4-yl=piperazino) or piperazin-2-yl. Indolyl can be indol-1-yl, indol-2-yl, indol-3-yl, indol-4-yl, indol-5-yl, indol-6-yl or indol-7-yl. Similarly, benzimidazolyl, benzoxazolyl and benzothiazol groups can be bonded via the 2-position and via any of the positions 4, 5, 6, and 7. Quinolinyl can be quinolin-2-yl, quinolin-3-yl, quinolin-4-yl, quinolin-5-yl, quinolin-5-yl, quinolin-7-yl or quinolin-8-yl, isoqinolinyl can be isoquinolin-1-yl, isoquinolin-3-yl, isoquinolin-4-yl, isoquinolin-5-yl, isoquinolin-6-yl, isoquinolin-7-yl or isoquinolin-8-yl. In addition to being bonded via any of the positions indicated for quinolinyl and isoquinolinyl, 1,2,3,4-tetrahydroquinolinyl and 1,2,3,4-tetrahydroisoquinolinyl can also be bonded via the nitrogen atoms in 1-position and 2-position, respectively. Substituents in heterocyclyl groups can be present in any desired position provided that a stable molecule results. The explanations relating to the heterocyclic group correspondingly apply to divalent heterocyclic groups including divalent heteroaromatic groups which may be bonded via any two ring carbon atoms and in the case of nitrogen heterocycles via any carbon atom and any suitable ring nitrogen atom or via any two suitable nitrogen atoms. For example, a pyridinediyl group can be pyridin-2,3-diyl, pyridin-2,4-diyl, pyridin-2,5-diyl, pyridin-2,6-diyl, pyridin-3,4-diyl or pyridin-3,5-diyl, a piperidinediyl group can be, among others, piperidin-1,2-diyl, piperidin-1,3-diyl, piperidin-1,4-diyl, piperidin-2,3-diyl, piperidin-2,4-diyl or piperidin-3,5-diyl, a piperazinediyl group can be, among others, piperazin-1,3-diyl, piperazin-1,4-diyl, piperazin-2,3-diyl, piperazin-2,5-diyl, etc.

Halogen is fluorine, chlorine, bromine or iodine, in one embodiment fluorine, chlorine or bromine, in another embodiment fluorine or chlorine, in another embodiment fluorine.

The present invention also encompasses pharmaceutically acceptable salts of the compounds of formula I. Depending on the specific case, the compounds of the formula I may exist in the from of acids or their salts formed with bases, or in the form of bases or their addition salts with acids, for example as acetic acid salt. Such salts form part of the invention. Addition salts with acids, for example, may be prepared with pharmaceutically acceptable acids according to standard procedures. Also the salts with other acids, for example trifluoroacetic acid salts, which are useful for purifying or isolating compounds of the formula I, form part of the invention.

Optically active carbon atoms present in the compounds of the formula I can independently of each other have R configuration or S configuration. The compounds of the formula I can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formula I, and it comprises all ratios of the stereoisomers in the mixtures. In case the compounds of the formula I can be present as E isomers or Z isomers, or cis isomers or trans isomers, the invention relates both to pure E isomers and pure Z isomers and to E/Z mixtures in all ratios, and pure cis isomers and pure trans isomers and to cis/trans mixtures in all ratios. The invention also comprises all tautomeric forms of the compounds of the formula I.

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formula I can also be obtained by employing stereochemically uniform starting materials or by using stereoselective reactions.

In one embodiment, one or two or three or four or five or six or seven or eight or nine centers of asymmetry formed by the carbon atoms to which R1, R2, R3, R4, R5, R6, R7, R8, R9, R10, R11, R12, R13, R14, R15, R16, R17 and R18 are attached, may have R configuration and the others may have S configuration.

In another embodiment one or two or three or four or five or six or seven or eight centers of asymmetry formed by the carbon atoms to which R1, R2, R3, R4, R5, R6, R7, R8, R9, R10, R11, R12, R13, R14, R15, R16, R17 and R18 are attached, may have R configuration and the others may have S configuration.

In another embodiment one or two or three or four or five or six or seven centers of asymmetry formed by the carbon atoms to which R1, R2, R3, R4, R5, R6, R7, R8, R9, R10, R11, R12, R13, R14, R15, R16, R17 and R18 are attached, may have R configuration and the others may have S configuration.

In another embodiment one or two or three or four or five or six centers of asymmetry formed by the carbon atoms to which R1, R2, R3, R4, R5, R6, R7, R8, R9, R10, R11, R12, R13, R14, R15, R16, R17 and R18 are attached, may have R configuration and the others may have S configuration.

In another embodiment one or two or three or four or five centers of asymmetry formed by the carbon atoms to which R1, R2, R3, R4, R5, R6, R7, R8, R9, R10, R11, R12, R13, R14, R15, R16, R17 and R18 are attached, may have R configuration and the others may have S configuration.

In another embodiment one or two or three or four centers of asymmetry formed by the carbon atoms to which R1, R2, R3, R4, R5, R6, R7, R8, R9, R10, R11, R12, R13, R14, R15, R16, R17 and R18 are attached, may have R configuration and the others may have S configuration.

In another embodiment one or two or three centers of asymmetry formed by the carbon atoms to which R1, R2, R3, R4, R5, R6, R7, R8, R9, R10, R11, R12, R13, R14, R15, R16, R17 and R18 are attached, may have R configuration and the others may have S configuration.

In another embodiment one or two centers of asymmetry formed by the carbon atoms to which R1, R2, R3, R4, R5, R6, R7, R8, R9, R10, R11, R12, R13, R14, R15, R16, R17 and R18 are attached, may have R configuration and the others may have S configuration.

In another embodiment one center of asymmetry formed by the carbon atoms to which R1, R2, R3, R4, R5, R6, R7, R8, R9, R10, R11, R12, R13, R14, R15, R16, R17 and R18 are attached, may have R configuration and the others may have S configuration.

In another embodiment the centers of asymmetry formed by the carbon atoms to which R1, R2, R3, R4, R5, R6, R7, R8, R9, R10, R11, R12, R13, R14, R15, R16, R17 and R18 are attached, may have S configuration.

In one embodiment, the invention relates to one or more of the specific cyclic peptide compounds of the formula I disclosed herein, and their pharmaceutically acceptable salts, for example one or more compounds selected from the compounds of the following formulae, which are the compounds of the illustrating examples described below:

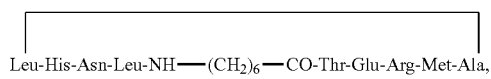 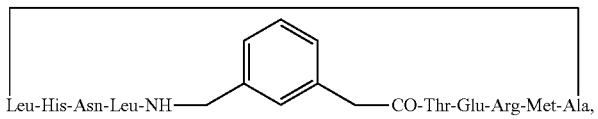

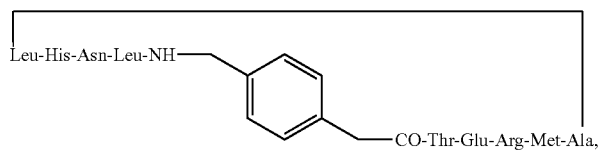

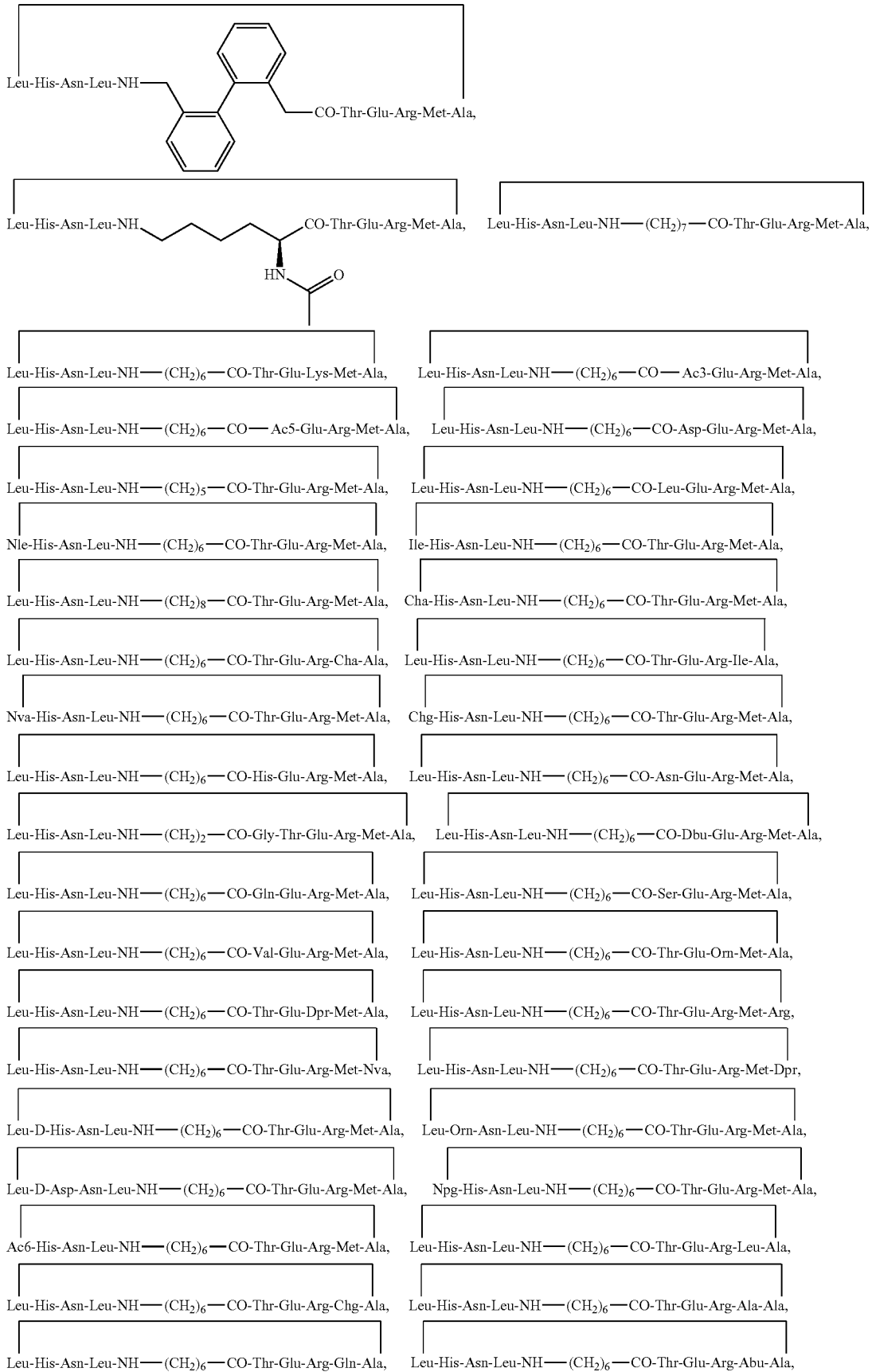

-continued

Leu-His-Asn-Leu-NH—(CH$_2$)$_6$—CO-Thr-Glu-Arg-Nle-Ala,  Leu-His-Asn-Leu-NH—(CH$_2$)$_6$—CO-Thr-Glu-Arg-Amb-Ala,

Leu-His-Asn-Leu-NH—(CH$_2$)$_6$—CO-Thr-Glu-Arg-Amp-Ala,  Leu-His-Asn-Leu-Gly-NH—(CH$_2$)$_4$—CO-Thr-Glu-Arg-Met-Ala,

Leu-His-Asn-Leu-NH—(CH$_2$)$_9$—CO-Thr-Glu-Arg-Met-Ala,  Leu-His-Asn-Leu-Gly-NH—(CH$_2$)$_3$—CO-Thr-Glu-Arg-Met-Ala,

Leu-His-Asn-Leu-Dpr-NH—(CH$_2$)$_3$—CO-Thr-Glu-Arg-Met-Ala,  Leu-His-Asn-Leu-NH—(CH$_2$)$_3$—CO-Asn-Thr-Glu-Arg-Met-Ala,

Leu-His-Asn-Leu-NH—(CH$_2$)$_2$—CO-Asn-Thr-Glu-Arg-Met-Ala,  Leu-His-Asn-Leu-NH—(CH$_2$)$_2$—CO-Ala-Thr-Glu-Arg-Met-Ala,

Leu-His-Asn-Leu-NH—(CH$_2$)$_3$—CO-Aib-Thr-Glu-Arg-Met-Ala,  Leu-His-Asn-Leu-NH—(CH$_2$)$_3$—CO-Ach3-Thr-Glu-Arg-Met-Ala,

Leu-His-Asn-Leu-NH—(CH$_2$)$_6$—CO-Thr-Glu-Arg-Met-Gln, and

Leu-His-Asn-Leu-NH—(CH$_2$)$_2$—O—(CH$_2$)$_2$—O—CH$_2$—CO-Thr-Glu-Arg-Met-Ala, and the pharmaceutically acceptable salt thereof, wherein the meaning of the groups in the formulae is as defined herein and, for example, Abu is L-2-aminobutyric acid, Ac3 is 1-aminocyclopropane-1-carboxylic acid, Ac5 is 1-aminocyclopentane-1-carboxylic acid, Ac6 is 1-aminocyclohexane-1-carboxylic acid, Aib is 2-aminoisobutyric acid, Amb is L-2-amino-4-methoxybutyric acid, Amp is L-2-amino-3-methoxypropionic acid, Cha is L-cyclohexylalanine, Chg is L-cyclohexylglycine, Dbu is L-2,4-diaminobutyric acid, Dpr is L-2,3-diaminopropionic acid, Nle is L-norleucine (=L-2-aminohexanoic acid), Npg is L-neopentylglycine (=L-2-amino-4,4-dimethylpentanoic acid), Nva is L-norvaline (=L-2-aminopentanoic acid), or the divalent residue of the specified amino acid which is bonded to the neighboring groups by peptide bonds, respectively, or otherwise the meaning of the groups in the formulae is their common meaning, and wherein the line with two rectangular bends indicates the peptide bond (=amide bond) between the N-terminal and the C-terminal amino acids of the depicted sequence. In another manner, the compounds of the invention may be represented by formulae like the following one, which shows by way of example the compound of the first of the formulae above, i.e. the compound of example 1, and in which the CO group depicted in the formula is bonded to the amino group of the neighboring amino acid Thr, the NH group depicted in the formula is bonded to the carboxy group of the neighboring amino acid Leu, and otherwise the other amino acids are linked to the neighboring amino acids in usual peptide manner.

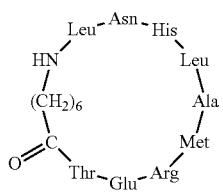

The present invention also relates to processes of preparation by which the compounds of the formula I are obtainable.

The compounds of the formula I can be prepared by a variety of synthetic schemes, which are well known in the art for peptide synthesis. The reactions described herein that are carried out in the synthesis of the compounds of the formula I, can generally be carried out according to the methods of conventional solution phase chemistry or solid phase chemistry. In one embodiment, the method for making the compounds of the invention in solution or on solid support is in accordance with conventional Fmoc-based techniques. The synthesis on solid support can be done manually or by various automatic peptide synthesizers which are commercially available and are used in accordance with known protocols. For example, the compounds of the formula I can be synthesized by solid-phase technology comprising the following steps:

1) attaching a compound of the formula Fmoc-NH—X4-X3-X2-X1-C(O)—OH, wherein Fmoc is 9H-fluoren-9-yl-methoxycarbonyl and X1, X2, X3 and X4 are as herein defined before, to a 2-chlorotrityl chloride resin and then cleaving off the protecting group Fmoc,
2) activating the next compound of the formula Fmoc-NH—C(R17)(R18)-C(O)—OH, attaching it to the compound which was attached to the resin the preceding step, and then cleaving off the protecting group Fmoc of the new N-terminal amino group,
3) repeating the procedure as described in step 2) above with Fmoc-NH—C(R15)(R16)-C(O)—OH,
4) subsequently repeating the procedure step by step until finally the new N-terminal amino group is prepared by attaching a compound of the formula Fmoc-NH—C(R1)(R2)-C(O)—OH, and then cleaving off the protecting group Fmoc of the new N-terminal amino group, where in between each step there are washing steps,
5) cleaving off the compound obtained according to steps 1) through 4) above from the resin by means of trifluoroacetic acid (TFA), for example 1% TFA in dichloromethane (DCM), or by means of HFIP (1,1,1,3,3,3-hexafluoro-2-propanol), to give a peptide of linear side chain-protected structure which comprises the amino acid residues which where used in steps 1) through 4),
6) activating the deprotected carboxylic acid of the C-terminal amino acid and cyclizing to the deprotected amino group of the N-terminal amino acid, and removing then the side-chain protection groups, for example in the presence of concentrated TFA, to give the compound of the formula I.

Instead of starting the assembly of the amino sequence present in the desired compound of the formula with the attachment of the compound of the formula Fmoc-NH—X4-X3-X2-X1-C(O)—OH to the resin, also another amino acid present in the desired compound of the formula I can be attached to the resin in the first step 1), for example a compound of the formula Fmoc-C(R9)(R10)-C(O)—OH, after deprotection then a compound of the formula Fmoc-C(R7)(R8)-C(O)—OH attached, and so on, and finally a compound of the formula Fmoc-C(R11)(R12)-C(O)—OH attached and, after cleavage from the resin, the respective peptide of linear side chain-protected structure obtained, which is then cyclized to give the compound of the formula I.

The applied solid phase technology uses an insoluble polymer for support during organic synthesis. The polymer-supported peptide chain permits the use of simple washing and filtration steps. For performing the synthesis, in the first step 1) the resin in a peptide synthesis vessel can gently be shaken with a solution of 2.1 equivalents of an Fmoc-protected amino acid and 4 equivalents diisopropylethylamine (DIEA) in dimethylformamide (DMF) for 3 h at 25° C., for example, the solvent then removed from the resin and the resin washed subsequently with DCM, DMF, isopropanol and cyclohexane. The Fmoc protecting group at the N-terminal end can then be removed by treating the resin with a mixture of DMF and piperidine for 5 minutes, for example, the solvent removed and this step repeated for 10 minutes, for example, the solvent removed and the resin washed with DCM, DMF, isopropanol and cyclohexane. For steps 2) to 4), 3 equivalents of the corresponding Fmoc-protected amino acid can be activated by diisopropylcarbodiimide (DIC)/1-hydroxybenzotriazole (HOBt), for example, and coupled to the deprotected amino acid or peptide attached to the resin which was obtained in the previous step, the solvent removed, the step repeated with 3 equivalents of the corresponding Fmoc protected amino acid, after 3 h the solvent removed and the resin washed subsequently with DCM, DMF, isopropanol and cyclohexane. The Fmoc protecting group at the N-terminal end can then be removed by treating the resin with a mixture of DMF and piperidine for 5 minutes, for example. When the synthesis of the linear peptide chain is completed, the linear peptide can be cleaved from the resin by treatment with HFIP, for example, and collected by filtration and evaporation of the solvent. Alternatively, the solid phase synthesis can be done with a microwave assisted peptide synthesizer, for example CEM Liberty, and 2.2 equivalents of the Fmoc-protected amino acids used for coupling and the activation of the Fmoc-protected amino acids be performed with 2-(1H-benzotriazole-1-yl)-1,1,3,3-tetramethyluronium hexafluorophosphate (HBTU)/HOBt in DMF.

Alternatively the compounds of the formula I can be synthesized by traditional solution chemistry comprising the coupling of protected amino acids, deprotection and cyclization to the target molecules by standard procedures known in the art.

Various general methods for the formation of an amide bond that can be employed in the synthesis of the compounds of formula I, are well known to those skilled in the art, for example from peptide chemistry. An amide coupling step can favorably be carried out by employing a free carboxylic acid and activating that carboxylic acid group, preferably in situ, by means of a customary coupling reagent such as a carbodiimide like dicyclohexylcarbodiimide (DCC) or diisopropylcarbodiimide (DIC), or an N,N'-carbonyldiazole like N,N'-carbonyldiimidazole, or an uronium salt like O-((cyano(ethoxycarbonyl)methylene)amino)-1,1,3,3-tetramethyluronium tetrafluoroborate (TOTU) or 2-(1H-benzotriazole-1-yl)-1,1,3,3-tetramethyluronium hexafluorophosphate (HBTU) or 2-(1H-benzotriazole-1-yl)-1,1,3,3-tetramethyluronium tetrafluoroborate (TBTU) or 2-(7-aza-1H-benzotriazole-1-yl)-1,1,3,3-tetramethyluronium tetrafluoroborate (TATU) or 2-(7-aza-1H-benzotriazole-1-yl)-1,1,3,3-tetramethyluronium hexafluorophosphate (HATU) or 2-(6-chloro-1H-benzotriazole-1-yl)-1,1,3,3-tetramethyluronium hexafluorophosphate (HCTU), or a chloroformic acid ester like ethyl chloroformate or isobutyl chloroformate, or tosyl chloride, or propylphosphonic acid anhydride, or others, and then reacting the activated carboxylic acid derivative with an amino compound. An amide bond can also be formed by reacting an amino compound with a carboxylic acid halide, in particular a carboxylic acid chloride, which can be prepared in a separate step or in situ from a carboxylic acid and, for example, thionyl chloride, or an carboxylic acid ester or thioester, for example a methyl ester, ethyl ester, phenyl ester, nitrophenyl ester, pentafluorophenyl ester, methylthio ester, phenylthio ester or pyridin-2-ylthio ester.

The activation reactions and coupling reactions are usually performed in the presence of an inert solvent (or diluent), for example in the presence of an aprotic solvent like dimethylformamide (DMF), tetrahydrofuran (THF), dimethyl sulfoxide (DMSO), hexamethyl phosphoric triamide (HMPT), 1,2-dimethoxyethane (DME), dioxane, or others, or in a mixture of such solvents. Depending on the specific process, the reaction temperature may be varied over a wide range and be, for example, from about −20° C. to the boiling temperature of the solvent or diluent. The preferred reaction temperature is between 0° C. and 30° C. Depending on the specific process, the coupling reactions may also be driven by microwave energy. Also depending on the specific process, it may be necessary or advantageous to add in a suitable amount one or more auxiliary agents, for example a base like a tertiary amine, such as N-ethylmorpholine, triethylamine or diisopropylethylamine, or an alkali metal alcoholate, such as sodium methoxide or potassium tert-butoxide, for adjusting the pH or neutralizing an acid that is formed or for liberating the free base of an amino compound that is employed in the form of an acid addition salt, or an N-hydroxyazole like 1-hydroxybenzotriazole, or a catalyst like 4-dimethylaminopyridine. Details on methods for the preparation of activated carboxylic acid derivatives and the formation of amide bonds and ester bonds as well as source literature are given in various standard references like, for example, March, J., Advanced Organic Chemistry, 4th ed., John Wiley & Sons, 1992; or Houben-Weyl, Methoden der organischen Chemie (Methods of Organic Chemistry), Georg Thieme Verlag.

As mentioned, in the synthesis of the compounds of the formula I generally standard protective groups techniques are used, and protective groups that may still be present in the products such as those obtained in the coupling reactions removed by standard procedures. For example, Fmoc is a preferred protecting group for an amino group in solid phase peptide synthesis. It can be introduced by reaction of an amino group with Fmoc-O-succinimide (Fmoc-OSu) in dioxane/water in the presence of $NaHCO_3$, for example. Deprotection can be done by treatment with piperidine in DMF. As another example, tert-butyl (tBu) protecting groups may be mentioned, in particular a tert-butoxycarbonyl (Boc) group which protects an amino group, or a tert-butyl ester group which is a protected form of a carboxylic acid, which can be deprotected, i.e. converted into the amino group or the carboxylic acid group, by treatment with trifluoroacetic acid, for example. Another preferred protecting group is the trityl group (Trt), which is a protecting group for the side chains of different amino acids. For example, the side chain of Asn, Gln, Ser, Thr, Tyr and His can be protected by the trityl group in order to prevent unwanted side reactions. The trityl protected groups can be deprotected with trifluoroacetic acid, for example. A further preferred protecting group is the 2,2,4,6,7-pentamethyldihydro-benzofuran-5-sulfonyl group (Pbf), which is a protecting group for the side chain of Arg. The Pbf-protected side chain can be deprotected by concentrated trifluoroacetic acid, for example. Another protecting group for the Arg side chain is the 2,2,5,7,8-pentamethylchroman-6-sulfonyl group (Pmc). After the coupling reaction, functional groups can also be generated from suitable precursor groups. In addition, a conversion into a physiologically tolerable or pharmaceutically acceptable salt of a compound of the formula I can then be carried out by known processes.

In general, a reaction mixture containing a final compound of the formula I or an intermediate is worked up and, if desired, the product is then purified by customary processes known to those skilled in the art. For example, a synthesized compound can be purified using well known methods such as crystallization, chromatography or reversed phase-high performance liquid chromatography (RP-HPLC) or other methods of separation based, for example, on the size, charge or hydrophobicity of the compound. Similarly, well known methods such as NMR, IR and mass spectrometry (MS) can be used for characterizing a compound of the invention.

The starting compounds of the formula I and other compounds which are employed in the synthesis of the compounds of formula I for introducing certain structural units, are commercially available or can be readily prepared from commercially available compounds by or analogously to procedures described below or in the literature which is readily available to those skilled in the art.

The compounds of the present invention inhibit the initial step of the thrombogenesis. In particular, they are inhibitors of the interaction between the platelet surface glycoprotein GPIb complex and the plasma protein von Willebrand factor. More particular, they are inhibitors of the interaction between the GPIb complex and the A1 domain of the von Willebrand factor.

The activity of compounds of the formula I can be shown by procedures known in the art, for example by determining their inhibition of the binding of platelets to vWF A1 domain in an appropriate assay. To this end, assay plates can be coated with vWF-A1 domain. After washing-off excess protein and blocking of the coated assay plates, the test compounds are added, for example at a concentration of 10 µM. Then fluorescence-labeled thrombocytes are added and incubated for 90 minutes. In a complex washing procedure all non-bound thrombocytes are removed and the plates are measured, for example in a laser-based reader Acumen Explorer or a bulk reader like Spectramax. For most active compounds, generally a dose response testing is done to determine $IC_{50}$ values (concentration at which the binding of platelets to vWF A1 domain is inhibited by 50%).

The activity of the compounds of the formula I can also be shown by measurement of platelet function with the PFA-100 Analyzer (Siemens Healthcare Diagnostics GmbH), for example, which measures platelet plug formation in a small, whole blood sample and reports a "closure time". It challenges platelets under high shear flow conditions similar to the physiologic environment in which platelets normally function, and simulates in vitro the function of platelets in primary hemostasis by measuring the PFA-100 closure time. Further, the activity of the compounds of the formula I can be determined by impedance aggregometry. Aggregometry is based on the principle that blood platelets are non-thrombogenic in their resting state, but expose receptors on their surface when they get activated which allow them to attach on vascular injuries and artificial surfaces. Platelet agglutination is induced by ristocetin, which is a specific agonist for GPIb-vWF interaction.

The compounds according to the invention can therefore be used for preparing medicaments, especially medicaments which are inhibitors of the interaction between GPIb and vWF. Accordingly, one aspect of the present invention relates to the compounds of the formula I and their pharmaceutically acceptable salts for use as pharmaceuticals. In another of its aspects the invention provides medicaments which comprise a compound of the formula I or a pharmaceutically acceptable salt thereof. These medicaments can be employed therapeutically or prophylactically for influencing platelet aggregation and for the treatment of diseases such as, for example, cardiovascular disorders, thromboembolic diseases or restenoses, wherein treatment includes the therapy as well as the prophylaxis, prevention and secondary prevention of diseases, and more specifically of disease states such as abnormal thrombus formation, myocardial infarction, acute myocardial infarction, unstable angina, acute coronary syndrome, coronary artery disease, reocclusion following coronary thrombolysis, occlusion during thromboplasty, coronary restenosis, thromboembolism, pulmonary embolism, left ventricular dysfunction, clinical vascular complications in patients with cardiovascular and cerebrovascular disease, acute vessel closure associated with thrombolytic therapy or percutaneous transluminal coronary angioplasty, transient ischemic attacks, stroke, atherosclerosis, pathologic thrombus formation occurring in the veins of the lower extremities following abdominal, knee and hip surgery, a risk of pulmonary thromboembolism, or disseminated systemic intravascular coagulatopathy occurring in vascular systems during septic shock, certain viral infections or cancer, for example, or as comedication to vascular interventional strategies.

In one of its aspects, the invention relates to a compound of formula I or a pharmaceutically acceptable salt thereof for the treatment of abnormal thrombus formation, acute myocardial infarction, unstable angina, thromboembolism, acute vessel closure associated with thrombolytic therapy or percutaneous transluminal coronary angioplasty, transient ischemic attacks, stroke, intermittent claudication or bypass grafting of the coronary or peripheral arteries, vessel luminal narrowing, restenosis post coronary or venous angioplasty, maintenance of vascular access patency in long-term hemodialysis patients, pathologic thrombus formation occurring in the veins of the lower extremities following abdominal, knee and hip surgery, a risk of pulmonary thromboembolism, disseminated systemic intravascular coagulatopathy occurring in vascular systems during septic shock, certain viral infections or cancer, coronary heart disease, myocardial infarction, angina pectoris, vascular restenosis, restenosis following angioplasty, adult respiratory distress syndrome, multi-organ failure, disseminated intravascular clotting disorder, or deep vein or proximal vein thrombosis which can occur following surgery.

In another of its aspects, the invention relates to the use of a compound of the formula I or a pharmaceutically acceptable salt thereof for preparing a medicament for the treatment of abnormal thrombus formation, acute myocardial infarction, unstable angina, thromboembolism, acute vessel closure associated with thrombolytic therapy or percutaneous transluminal coronary angioplasty, transient ischemic attacks, stroke, intermittent claudication or bypass grafting of the coronary or peripheral arteries, vessel luminal narrowing, restenosis post coronary or venous angioplasty, maintenance of vascular access patency in long-term hemodialysis patients, pathologic thrombus formation occurring in the veins of the lower extremities following abdominal, knee and hip surgery, a risk of pulmonary thromboembolism, disseminated systemic intravascular coagulatopathy occurring in vascular systems during septic shock, certain viral infections or cancer, coronary heart disease, myocardial infarction, angina pectoris, vascular restenosis, restenosis following angioplasty, adult respiratory distress syndrome, multi-organ failure, disseminated intravascular clotting disorder, or deep vein or proximal vein thrombosis which can occur following surgery.

In another of its aspects, the invention relates to a method for the treatment of abnormal thrombus formation, acute myocardial infarction, unstable angina, thromboembolism, acute vessel closure associated with thrombolytic therapy or percutaneous transluminal coronary angioplasty, transient ischemic attacks, stroke, intermittent claudication or bypass grafting of the coronary or peripheral arteries, vessel luminal narrowing, restenosis post coronary or venous angioplasty, maintenance of vascular access patency in long-term hemodialysis patients, pathologic thrombus formation occurring in the veins of the lower extremities following abdominal, knee and hip surgery, a risk of pulmonary thromboembolism, disseminated systemic intravascular coagulatopathy occurring in vascular systems during septic shock, certain viral infections or cancer, coronary heart disease, myocardial infarction, angina pectoris, vascular restenosis, restenosis following angioplasty, adult respiratory distress syndrome, multi-organ failure, disseminated intravascular clotting disorder, or deep vein or proximal vein thrombosis which can occur following surgery, which comprises administering to a patient an effective dose of a compound according to the invention or a pharmaceutically acceptable salt thereof.

According to another of its aspects, the present invention relates to pharmaceutical compositions, or pharmaceutical preparations, comprising as active principle a compound of the formula I and/or a pharmaceutically acceptable salt thereof. These pharmaceutical compositions comprise an effective dose of at least one compound of the formula I or a pharmaceutically acceptable salt thereof, and at least one pharmaceutically acceptable excipient. The said excipients are selected, in accordance with the pharmaceutical form and method of administration desired, from the customary excipients, which are known to a person skilled in the art.

In the pharmaceutical compositions of the present invention for oral, sublingual, subcutaneous, intramuscular, intravenous, topical, local, intratracheal, intranasal, transdermal or rectal administration, the active principle of formula I above or its salt may be administered in a unit administration form, in a mixture with conventional pharmaceutical excipients, to animals and to human beings for the treatment of disorders or diseases. The unit administration forms appropriate include oral forms such as tablets, soft or hard gel capsules, powders, granules and oral solutions or suspensions, sublingual, buccal, intratracheal, intraocular and intranasal administration forms, forms for inhalative, topical, transdermal, subcutaneous, intramuscular or intravenous administration, rectal administration forms and implants. For topical application it is possible to use the compounds according to the invention in creams, gels, ointments or lotions.

The pharmaceutical compositions according to the invention are prepared in a manner known per se and familiar to one skilled in the art, pharmaceutically acceptable inert inorganic and/or organic carrier substances and/or additives being used in addition to the compound(s) of the formula I and/or its (their) pharmaceutically acceptable salts. For the production of pills, tablets, coated tablets and hard gelatin capsules it is possible to use, for example, lactose, corn starch or derivatives thereof, talc, stearic acid or its salts, etc. Carrier substances for soft gelatin capsules and suppositories are, for example, fats, waxes, semisolid and liquid polyols, natural or hardened oils, etc. Suitable carrier substances for the production of solutions, for example injection solutions, or of emulsions or syrups are, for example, water, saline, alcohols, glycerol, polyols, sucrose, invert sugar, glucose, vegetable oils, etc. Suitable carrier substances for microcapsules, implants or rods are, for example, copolymers of glycolic acid and lactic acid. The pharmaceutical compositions normally contain about 0.5 to about 90% by weight of the compounds of the formula I and/or their pharmaceutically acceptable salts. The amount of the active ingredient of the formula I and/or its pharmaceutically acceptable salts in the pharmaceutical compositions normally is from about 0.5 to about 1000 mg, preferably from about 1 to about 500 mg.

In addition to the active ingredients of the formula I and/or their physiologically acceptable salts and to carrier substances, the pharmaceutical compositions can contain one or more additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula I and/or their pharmaceutically acceptable salts. In case a pharmaceutical composition contains two or more compounds of the formula I the selection of the individual compounds can aim at a specific overall pharmacological profile of the pharmaceutical composition. For example, a highly potent compound with a shorter duration of action may be combined with a long-acting compound of lower potency. The flexibility permitted with respect to the choice of substituents in the compounds of the formula I allows a great deal of control over the biological and physico-chemical properties of the compounds and thus allows the selection of such desired compounds. Furthermore, in addition to at least one compound of the formula I and/or its pharmaceutically acceptable salts, the pharmaceutical compositions can also contain one or more other therapeutically or prophylactically active ingredients. As an example, a unit administration form of a compound according to the invention in tablet form may comprise the following components:

| | |
|---|---|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

When using the compounds of the formula I, the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from 0.01 mg/kg to 100 mg/kg, preferably from 0.1 mg/kg to 50 mg/kg, in particular from 0.1 mg/kg to 10 mg/kg, in each case in mg per kg of body weight. The daily dose can be divided, in particular in the case of the administration of relatively large amounts, into several, for example 2, 3 or 4, part administrations. There may be particular cases in which higher or lower dosages are appropriate, where such dosages do not depart from the scope of the invention. According to usual practice, the dosage that is appropriate for each patient is determined by the doctor according to the mode of administration and the weight and response of the said patient.

A compound of the formula I can also advantageously be used as an antiaggregant outside an individual. For example, an effective amount of a compound of the invention can be contacted with a freshly drawn blood sample to prevent aggregation of the blood sample. Further, a compound of the formula I or a salt thereof can be used for diagnostic purposes, for example in in vitro diagnoses, and as an auxiliary in biochemical investigations. For example, a compound of the formula I can be used in an assay to identify the presence of the GPIb receptor or to isolate the GPIb receptor containing tissue in a substantially purified form. A compound of the invention can be labeled with, for example, a radioisotope, and the labeled compound bound to the GPIb receptor is then detected using a routine method useful for detecting the particular label. Thus, a compound of the formula I or a salt thereof can be used as a probe to detect the location or amount of GPIb receptors activity in vivo, in vitro or ex vivo.

Furthermore, the compounds of the formula I can be used as synthesis intermediates for the preparation of other compounds, in particular of other pharmaceutical active ingredients, which are obtainable from the compounds of the formula I, for example by introduction of substituents or modification of functional groups.

The general synthetic sequences for preparing the compounds useful in the present invention our outlined in the examples given below. Both an explanation of, and the actual procedure for, the various aspects of the present invention are described where appropriate.

List of Abbreviations
Abu 2-Aminobutyric acid
4Abu 4-Aminobutyric acid
Ac Acetyl
Ac3 1-Aminocyclopropane-1-carboxylic acid
Ac5 1-Aminocyclopentane-1-carboxylic acid
Ac6 1-Aminocyclohexane-1-carboxylic acid
Aib 2-Aminoisobutyric acid
Ala Alanine
Amb 2-Amino-4-methoxybutyric acid
Amp 2-Amino-3-methoxypropionic acid
Arg Arginine
Asn Asparagine
Asp Aspartic acid
bAla beta-Alanine
Boc tert-Butyloxycarbonyl
calc. Calculated
Cha Cyclohexylalanine
Chg Cyclohexylglycine
Cys Cysteine
Dbu 2,4-Diaminobutyric acid
DCC N,N'-Dicyclohexylcarbodiimide
DCM Dichloromethane
DIEA Diisopropylethylamine
DIC N,N'-Diisopropylcarbodiimide
DME 1,2-Dimethoxyethane
DMF N,N-Dimethylformamide
DMSO Dimethyl sulfoxide
Dpr 2,3-Diaminopropionic acid
DTE Dithioerythritol
D-Asp D-Aspartic acid
D-His D-Histidine
Fmoc 9H-Fluoren-9-ylmethoxycarbonyl
Gln Glutamine
Glu Glutamic acid
Gly Glycine
HATU 2-(7-Aza-1H-benzotriazole-1-yl)-1,1,3,3-tetramethyluronium hexafluorophosphate
HBTU 2-(1H-Benzotriazole-1-yl)-1,1,3,3-tetramethyluronium hexafluorophosphate
HFIP 1,1,1,3,3,3-Hexafluoro-2-propanol
His Histidine
HOBt 1-Hydroxybenzotriazole
Ile Isoleucine
Leu Leucine
Lys Lysine
Met Methionine
MS Mass spectrometry
MW Molecular weight
Nle Norleucine
Npg Neopentylglycine
Nva Norvaline
obs. Observed
Orn Ornithine
Pbf 2,2,4,6,7-Pentamethyldihydro-benzofuran-5-sulfonyl
HPLC High performance liquid chromatography
Ser Serine
tBu tert-Butyl
THF Tetrahydrofuran
TFA Trifluoroacetic acid
Thr Threonine
Trt Trityl
Val Valine Unless specified otherwise, the optionally modified three letter code of chiral amino acids, or of the respective amino acid residues, which occurs in the structures and names of compounds, indicates that the amino acid moiety in the example compounds and the respective starting material has L configuration at the chiral center in α position, which except for certain cases such as cysteine corresponds to S configuration. Thus, for example, Ala, denotes L-alanine or L-alanyl, H₂N-Ala-OH denotes L-alanine, Glu(tBu) denotes L-glutamic acid or L-glutamyl which are protected in the side chain by tert-butyl, or Fmoc-His(Boc)-OH denotes L-histidine which is protected at the amino group in α position by 9-fluorenylmethoxycarbonyl and in the side chain by tert-butoxycarbonyl. Unless specified otherwise, such as in the case of a D-His moiety, for example, all chiral amino acids present in the following example compounds have L configuration.

The examples which follow describe the preparation of certain compounds in accordance with the invention. These examples are not limitative, and merely illustrate the present invention.

EXAMPLES

When in the final step of the synthesis of a compound an acid such as trifluoroacetic acid or acetic acid was used, for example when a compound was purified by chromatography using an eluent which contained such an acid, in some cases, depending on the work-up procedure, for example the details of a freeze-drying process, the compound was obtained partially or completely in the form of a salt of the acid used, for example in the form of the acetic acid salt or trifluoroacetic acid salt.

Peptide Synthesis Procedures and General Synthesis Procedures

Preparation of compounds of the present invention as described in the following examples is meant to be illustrative rather than limiting. Starting materials used in the synthesis were obtained from chemical vendors such as Aldrich, Sigma, Fluka, Novabiochem, Bachem peptides&elephants and Advanced Chemtech. During the synthesis, the functional groups of the amino acid derivatives used were protected by blocking groups to prevent side reaction during the coupling steps. Examples of suitable protecting groups and their use are described in The Peptides: Analysis, Synthesis, Biology, vol. 9, Special Methods in Peptide Synthesis, part C, Udenfriend, S., and Meienhofer, J., (editors), Academic Press, San Diego, 1987.

General solid-phase peptide synthesis was used to produce the compounds of the invention. Such methods are described, for example, in Steward, J. M., and Young, J. D., Solid Phase Peptide Synthesis, Freeman & Co., San Francisco, 1969. The amino acid sequences as described in the following examples were assembled by standard Fmoc chemistry utilizing a Peptide Synthesizer or suitable peptide synthesis vessels for manual peptide synthesis. The solid support was 2-chlorotrityl chloride resin. The automated or manual assembly was carried out by using the standard DIC/HOBt or alternatively HBTU/HOBt chemistry protocol.

The stepwise chain synthesis started from the C-terminal end of a linear peptide and was accomplished in 10 or 11 steps, depending on the number of peptide bonds to be formed. In step 1,2-chlorotrityl chloride resin was treated with 2.1 equivalents of an Fmoc-protected amino acid and 4 equivalents of DIEA in DCM as the solvent for 3 h. Then, the solvent was removed from the resin and the resin was washed one after another with DCM (2×), DMF (2×), isopropanol (2×) and cyclohexane (2×). Then, Fmoc at the N-terminal end was removed by treating the resin with a 4:1 mixture of DMF and piperidine for 5 minutes. This process was repeated for 10 minutes for complete side chain deprotection. Then, the solvent was removed and the resin was washed one after another with DMF (2×) and DCM (2×). In step 2, 3 equivalents of an Fmoc-protected amino acid were activated by DIC/HOBt and coupled to the deprotected peptide resin from step 1. The solvent was removed and the resin was again treated with 3 equivalents of the activated Fmoc protected amino acid. Then, Fmoc was removed by treating the resin with a 4:1 mixture of DMF and piperidine for 5 minutes. This process was repeated for 10 minutes for complete amino group deprotection. Then, the solvent was removed from the resin and the resin was washed one after another with DMF (2×), isopropanol (2×) and DCM (2×). Appropriate steps were carried out until step 10, the coupling of the last Fmoc protected amino acid. Then, Fmoc at the N-terminal end of the peptide sequence was removed by treating the resin with a 4:1 mixture of DMF and piperidine for 5 minutes. This process was repeated for 10 minutes for complete amino group deprotection. The linear side chain protected peptide was cleaved from the resin by treatment with HFIP in DCM for 30 minutes at room temperature. The resin was filtered from the cleaved peptide and the cleavage procedure was repeated once more. The combined solutions were then evaporated under vacuum and the linear peptide was used for the cyclization step. The carboxylic acid moiety of the C-terminal amino acid was activated by HATU/DIEA and cyclized to the amino group of the N-terminal amino acid. Then, the side chain protection groups were removed with TFA/DTE in DCM at room temperature. The solvent was removed and the peptide purification was accomplished using standard preparative HPLC techniques. Following the side chain deprotection, the peptide was dissolved in water loaded onto a reversed phase C18 HPLC column and eluted with an aqueous 0.1% trifluoroacetic acid/acetonitrile (v/v) gradient while monitoring at 225 nm. After collecting the fractions containing the intended synthetic product, the peptide solution was lyophilized and the peptide was subjected to an identification process, which included analytical HPLC and/or mass spectral analysis and/or NMR to confirm that the correct compound was synthesized. The trifluoroacetic acid salt can be converted into a salt of another acid by an additional chromatographic step in which an eluent containing such an acid is used. Unless stated otherwise, the example compounds described below were isolated as trifluoroacetic acid salt, which salt is not specified in the formulae and names of the compounds.

Example 1

Cyclo[Leu-His-Asn-Leu-NH—(CH$_2$)$_6$—CO-Thr-Glu-Arg-Met-Ala]

Leu-His-Asn-Leu-NH—(CH$_2$)$_6$—CO-Thr-Glu-Arg-Met-Ala

A) Linear Peptide Synthesis:

(SEQ ID NO: 1)
H$_2$N-Leu-His(Boc)-Asn-Leu-NH-(CH$_2$)$_6$—CO-Thr(tBu)-

Glu(tBu)-Arg(Pbf)-Met-Ala-OH

Starting material: 2-Chlorotrityl chloride resin
Resin attachment: DIEA/DCM (1. step)
Coupling: DIC/HOBt (2. step-10. step)
Deprotection: Piperidine
Cleavage from resin: HFIP
1. Step: Fmoc-Ala-OH
2. Step: Fmoc-Met-OH
3. Step: Fmoc-Arg(Pbf)-OH
4. Step: Fmoc-Glu(tBu)-OH
5. Step: Fmoc-Thr(tBu)-OH
6. Step: Fmoc-NH—(CH$_2$)$_6$—CO—OH
7. Step: Fmoc-Leu-OH
8. Step: Fmoc-Asn-OH
9. Step: Fmoc-His(Boc)-OH
10. Step: Fmoc-Leu-OH Yield: 1.497 g (cleaved from resin and used without further purification)

B) Cyclic Peptide Synthesis:

(SEQ ID NO: 57)
Cyclo[Leu-His-Asn-Leu-NH-(CH$_2$)$_6$—CO-Thr-Glu-Arg-

Met-Ala]

A solution of 1.497 g (0.893 mmol) of the linear peptide of example 1, step A) in 200 ml of DMF was slowly added over a period of 60 min to a solution of 1.019 g (3 eq., 2.679 mmol) of HATU and 4.44 ml (30 eq., 26.79 mmol) of DIEA in 36 ml of DMF at room temperature and stirring. After further 12 h at room temperature the solvent was evaporated and the residue was treated with a saturated aqueous solution of NaHCO$_3$.

The aqueous solution was extracted with DCM. The separated organic layer was dried (MgSO$_4$) and evaporated. The residue was loaded onto a preparative reversed phase C18 column, eluted with an aqueous 0.1% trifluoroacetic acid/acetonitrile (v/v) gradient, and the fractions containing the target product were collected and lyophilized. The product (77 mg) was treated with 0.613 ml of trifluoroacetic acid and 6.155 mg of DTE in 15 ml of DCM for 8 h at room temperature. After evaporation, the residue was loaded onto a preparative reversed phase C18 column, eluted with an aqueous 0.1% trifluoroacetic acid/acetonitrile (v/v) gradient, and the fractions containing the target product were collected and lyophilized to yield 37 mg of the title compound.

MS: MW calc. 1192.63; MW obs. 1193.58 (M+1)$^+$.

Example 1

Acetic Acid Salt

Cyclo[Leu-His-Asn-Leu-NH—(CH$_2$)$_6$—CO-Thr-Glu-Arg-Met-Ala]

Leu-His-Asn-Leu-NH—(CH$_2$)$_6$—CO-Thr-Glu-Arg-Met-Ala

A) Linear Peptide Synthesis:

```
                                          (SEQ ID NO: 113)
H2N-Thr(tBu)-Glu(tBu)-Arg(Pbf)-Met-Ala-Leu-

His(Trt)-Asn(Trt)-Leu-NH-(CH2)6-CO-OH
```

Starting material: 2-Chlorotrityl chloride resin
Resin attachment: DIEA/DCM (1. step)
  Coupling: DIC/HOBt (2. step-10. step)
Deprotection: Piperidine
Cleavage from resin: TFA (1%) in DCM followed by TFA (2%) in DMF
1. Step: Fmoc-NH—(CH$_2$)$_6$—CO—OH
2. Step: Fmoc-Leu-OH
3. Step: Fmoc-Asn(Trt)-OH
4. Step: Fmoc-His(Trt)-OH
5. Step: Fmoc-Leu-OH
6. Step: Fmoc-Ala-OH
7. Step: Fmoc-Met-OH
8. Step: Fmoc-Arg(Pbf)-OH
9. Step: Fmoc-Glu(tBu)-OH
10. Step: Fmoc-Thr(tBu)-OH Yield: 5.9 g (cleaved from resin and used without further purification)

B) Cyclic Peptide Synthesis:

```
                                           (SEQ ID NO: 57)
Cyclo[Leu-His-Asn-Leu-NH-(CH2)6-CO-Thr-Glu-Arg- Met-Ala]
```

Prepared as in Example 1B, except that a further chromatographic step as final step was added in which the eluent contained acetic acid. The product was collected and lyophilized to yield 1.5 g of the title compound as acetic acid salt.

Example 2

```
Cyclo[Leu-His-Asn-Leu-NH-X4-X3-X2-X1-CO-Thr-Glu-

Arg-Met-Ala],
``` wherein

—X4—X3—X2—X1— in example 2 is

[m-xylylene / 1,3-disubstituted benzene structure]

Leu-His-Asn-Leu-NH—X4—X3—X2—X1—CO-Thr-Glu-Arg-Met-Ala

A) Linear Peptide Synthesis

```
                                            (SEQ ID NO: 2)
H2N-Leu-His(Boc)-Asn-Leu-NH-X4-X3-X2-X1-CO-

Thr(tBu)-Glu(tBu)-Arg(Pbf)-Met-Ala-OH
```

Prepared as in Example 1A, except that Fmoc-7-aminoheptanoic acid in step 6 was replaced with Fmoc-(3-aminomethyl-phenyl)-acetic acid. Yield: 0.749 g (cleaved from resin and used without further purification).

B) Cyclic Peptide Synthesis:

```
                                           (SEQ ID NO: 58)
Cyclo[Leu-His-Asn-Leu-NH-X4-X3-X2-X1-CO-Thr-Glu- Arg-Met-Ala]
```

Prepared as in Example 1B. Yield: 69 mg of the title compound.

MS: MW calc. 1213.43; MW obs. 1213.76 (M+1)$^+$.

Example 3

```
Cyclo[Leu-His-Asn-Leu-NH-X4-X3-X2-X1-CO-Thr-Glu-

Arg-Met-Ala]
``` wherein

—X4—X3—X2—X1— in example 3 is

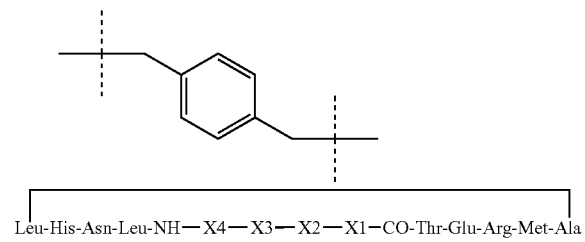

Leu-His-Asn-Leu-NH—X4—X3—X2—X1—CO-Thr-Glu-Arg-Met-Ala

A) Linear Peptide Synthesis:

(SEQ ID NO: 3)
H₂N-Leu-His(Boc)-Asn-Leu-NH-X4-X3-X2-X1-CO-

Thr(tBu)-Glu(tBu)-Arg(Pbf)-Met-Ala-OH

Prepared as in Example 1A, except that Fmoc-7-aminoheptanoic acid in step 6 was replaced with Fmoc-(4-aminomethyl-phenyl)-acetic acid. Yield: 0.757 g (cleaved from resin and used without further purification).
B) Cyclic Peptide Synthesis:

(SEQ ID NO: 59)
Cyclo[Leu-His-Asn-Leu-NH-X4-X3-X2-X1-CO-Thr-Glu-

Arg-Met-Ala]

Prepared as in Example 1B. Yield: 8.2 mg of the title compound.
MS: MW calc. 1213.43; MW obs. 1213.69 (M+1)⁺.

Example 4

Cyclo[Leu-His-Asn-Leu-NH-X4-X3-X2-X1-CO-Thr-Glu-

Arg-Met-Ala]

wherein

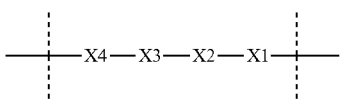

in example 4 is

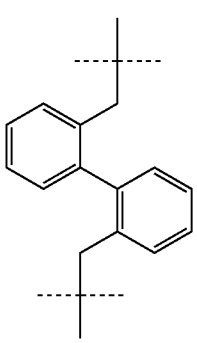

Leu-His-Asn-Leu-NH—X4—X3—X2—X1—CO-Thr-Glu-Arg-Met-Ala

A) Linear Peptide Synthesis:

(SEQ ID NO: 4)
H₂N-Leu-His(Boc)-Asn-Leu-NH-X4-X3-X2-X1-CO-

Thr(tBu)-Glu(tBu)-Arg(Pbf)-Met-Ala-OH

Prepared as in Example 1A, except that Fmoc-7-aminoheptanoic acid in step 6 was replaced with [2'-(Fmoc-aminomethyl)-biphenyl-2-yl]-acetic acid. Yield: 1.67 g (cleaved from resin and used without further purification).
B) Cyclic Peptide Synthesis:

(SEQ ID NO: 60)
Cyclo[Leu-His-Asn-Leu-NH-X4-X3-X2-X1-CO-Thr-Glu-

Arg-Met-Ala]

Prepared as in Example 1B. Yield: 7.3 mg of the title compound.
MS: MW calc. 1289.53; MW obs. 1289.62 (M+1)⁺.

Example 5

Cyclo[Leu-His-Asn-Leu-NH-X4-X3-X2-X1-CO-Thr-Glu-

Arg-Met-Ala]

wherein

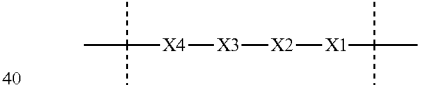

in example 5 is

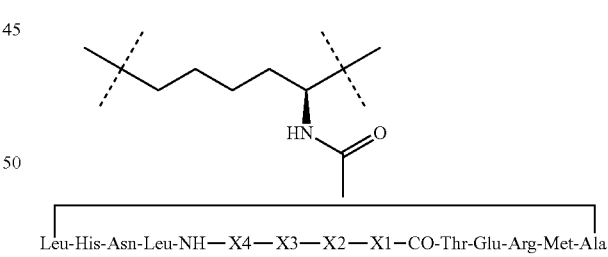

Leu-His-Asn-Leu-NH—X4—X3—X2—X1—CO-Thr-Glu-Arg-Met-Ala

A) Linear Peptide Synthesis:

(SEQ ID NO: 5)
H₂N-X4-X3-X2-X1-CO-Thr(tBu)-Glu(tBu)-Arg(Pbf)-Met-

Ala-Leu-His(Trt)-Asn(Trt)-Leu-OH

Starting material: 2-Chlorotrityl chloride resin
Resin attachment: DIEA/DCM (1. step)
Coupling: DIC/HOBt (2. step-10. step)
Deprotection: Piperidine
Cleavage from resin: HFIP 1. Step: Fmoc-Leu-OH
2. Step: Fmoc-Asn(Trt)-OH
3. Step: Fmoc-His(Trt)-OH
4. Step: Fmoc-Leu-OH
5. Step: Fmoc-Ala-OH
6. Step: Fmoc-Met-OH
7. Step: Fmoc-Arg(Pbf)-OH
8. Step: Fmoc-Glu(tBu)-OH
9. Step: Fmoc-Thr(tBu)-OH
10. Step: Fmoc-NH—X4-X3-X2-X1-CO—OH=Ac-Lys(Fmoc)-OH
Yield: 1.94 g (cleaved from resin and used without further purification)

B) Cyclic Peptide Synthesis:

(SEQ ID NO: 61)
Cyclo[Leu-His-Asn-Leu-NH-X4-X3-X2-X1-CO-Thr-Glu-Arg-Met-Ala]

A solution of 1.94 g (0.922 mmol) of the linear peptide of example 5, step A) in 180 ml of DMF was slowly added over a period of 75 min to a solution of 1.052 g (3 eq., 2.767 mmol) of HATU and 0.457 ml (3 eq., 2.767 mmol) of DIEA in 15 ml of DMF and 170 ml of DCM at room temperature and stirring. After further 12 h at room temperature the solvent was evaporated and the residue was treated with a saturated aqueous solution of $NaHCO_3$. The aqueous solution was extracted with DCM. The separated organic layer was dried ($MgSO_4$) and evaporated. The residue was loaded onto a preparative reversed phase C18 column, eluted with an aqueous 0.1% trifluoroacetic acid/acetonitrile (v/v) gradient, and the fractions containing the target product were collected and lyophilized. The product (65 mg, 3%) was treated with 1 ml of trifluoroacetic acid and 3.606 mg of DTE in 3 ml of DCM for 8 h at room temperature. After evaporation, the residue was loaded onto a preparative reversed phase C18 column, eluted with an aqueous 0.1% trifluoroacetic acid/acetonitrile (v/v) gradient, and the fractions containing the target product were collected and lyophilized to yield 3 mg of the title compound.
MS: MW calc. 1236.47; MW obs. 1236.92 $(M+1)^+$.

Example 6

Cyclo[Leu-His-Asn-Leu-NH—$(CH_2)_7$—CO-Thr-Glu-Arg-Met-Ala]
Leu-His-Asn-Leu-NH—$(CH_2)_7$—CO-Thr-Glu-Arg-Met-Ala A) Linear Peptide Synthesis:

(SEQ ID NO: 6)
$H_2N-(CH_2)_7-CO-Thr(tBu)-Glu(tBu)-Arg(Pbf)-Met-Ala-Leu-His(Trt)-Asn(Trt)-Leu-OH$

Prepared as in Example 5A, except that Ac-Lys(Fmoc)-OH in step 10 was replaced with Fmoc-8-amino-octanoic acid. Yield: 1.393 g (cleaved from resin and used without further purification).

B) Cyclic Peptide Synthesis:

(SEQ ID NO: 62)
Cyclo[Leu-His-Asn-Leu-NH-$(CH_2)_7$-CO-Thr-Glu-Arg-Met-Ala]

Prepared as in Example 5B. Yield: 50 mg of the title compound.
MS: MW calc. 1207.47; MW obs. 1207.80 $(M+1)^+$.

Example 7

Cyclo[Leu-His-Asn-Leu-NH—$(CH_2)_6$—CO-Thr-Glu-Lys-Met-Ala]
Leu-His-Asn-Leu-NH—$(CH_2)_6$—CO-Thr-Glu-Lys-Met-Ala A) Linear Peptide Synthesis:

(SEQ ID NO: 7)
$H_2N-(CH_2)_6-CO-Thr(tBu)-Glu(tBu)-Lys(Boc)-Met-Ala-Leu-His(Trt)-Asn(Trt)-Leu-OH$

Prepared as in Example 5A, except that Fmoc-Arg(Pbf)-OH in step 7 was replaced with Fmoc-Lys(Boc)-OH and Ac-Lys(Fmoc)-OH in step 10 was replaced with Fmoc-7-amino-heptanoic acid. Yield: 1.8 g (cleaved from resin and used without further purification).

B) Cyclic Peptide Synthesis:

(SEQ ID NO: 63)
Cyclo[Leu-His-Asn-Leu-NH-$(CH_2)_6$-CO-Thr-Glu-Lys-Met-Ala]

Prepared as in Example 5B. Yield: 30 mg of the title compound.
MS: MW calc. 1165.43; MW obs. 1165.79 $(M+1)^+$.

Example 8

Cyclo[Leu-His-Asn-Leu-NH—$(CH_2)_6$—CO-Ac3-Glu-Arg-Met-Ala]
Leu-His-Asn-Leu-NH—$(CH_2)_6$—CO-Ac3-Glu-Arg-Met-Ala A) Linear Peptide Synthesis:

(SEQ ID NO: 8)
$H_2N-(CH_2)_6-CO-Ac3-Glu(tBu)-Arg(Pbf)-Met-Ala-Leu-His(Trt)-Asn(Trt)-Leu-OH$

Prepared as in Example 5A, except that Fmoc-Thr(tBu)-OH in step 9 was replaced with Fmoc-1-aminocyclopropane-1-carboxylic acid (Fmoc-Ac3-OH) and Ac-Lys(Fmoc)-OH in step 10 was replaced with Fmoc-7-amino-heptanoic acid. Yield: 2.25 g (cleaved from resin and used without further purification).

B) Cyclic Peptide Synthesis:

(SEQ ID NO: 64)
Cyclo[Leu-His-Asn-Leu-NH-$(CH_2)_6$-CO-Ac3-Glu-Arg-Met-Ala]

Prepared as in Example 5B. Yield: 70 mg of the title compound.

MS: MW calc. 1175.43; MW obs. 1176.05 (M+1)+.

Example 9

Cyclo[Leu-His-Asn-Leu-NH—(CH$_2$)$_6$—CO-Ac5-Glu-Arg-Met-Ala]

A) Linear Peptide Synthesis:

(SEQ ID NO: 9)
H$_2$N—(CH$_2$)$_6$—CO-Ac5-Glu(tBu)-Arg(Pbf)-Met-Ala-Leu-His(Trt)-Asn(Trt)-Leu-OH

Prepared as in Example 8A, except that Fmoc-1-aminocyclopropane-1-carboxylic acid in step 9 was replaced with Fmoc-1-aminocyclopentane-1-carboxylic acid (Fmoc-Ac5-OH). Yield: 1.9 g (cleaved from resin and used without further purification).

B) Cyclic Peptide Synthesis:

(SEQ ID NO: 65)
Cyclo[Leu-His-Asn-Leu-NH-(CH$_2$)$_6$-CO-Ac5-Glu-Arg-Met-Ala]

Prepared as in Example 5B. Yield: 78 mg of the title compound.

MS: MW calc. 1203.48; MW obs. 1204.01 (M+1)+.

Example 10

Cyclo[Leu-His-Asn-Leu-NH—(CH$_2$)$_6$—CO-Asp-Glu-Arg-Met-Ala]

A) Linear Peptide Synthesis:

(SEQ ID NO: 10)
H$_2$N—(CH$_2$)$_6$—CO-Asp(tBu)-Glu(tBu)-Arg(Pbf)-Met-Ala-Leu-His(Trt)-Asn(Trt)-Leu-OH

Prepared as in Example 8A, except that Fmoc-1-Aminocyclopropane-1-carboxylic acid in step 9 was replaced with Fmoc-Asp(tBu)-OH. Yield: 2.55 g (cleaved from resin and used without further purification).

B) Cyclic Peptide Synthesis:

(SEQ ID NO: 66)
Cyclo[Leu-His-Asn-Leu-NH-(CH$_2$)$_6$-CO-Asp-Glu-Arg-Met-Ala]

Prepared as in Example 5B. Yield: 31 mg of the title compound.

MS: MW calc. 1207.43; MW obs. 1208.97 (M+1)+.

Example 11

Cyclo[Leu-His-Asn-Leu-NH—(CH$_2$)$_5$—CO-Thr-Glu-Arg-Met-Ala]

A) Linear Peptide Synthesis:

(SEQ ID NO: 11)
H$_2$N—(CH$_2$)$_5$—CO-Thr(tBu)-Glu(tBu)-Arg(Pbf)-Met-Ala-Leu-His(Trt)-Asn(Trt)-Leu-OH

Prepared as in Example 5A, except that Ac-Lys(Fmoc)-OH in step 10 was replaced with Fmoc-6-amino-hexanoic acid. Yield: 1.3 g (cleaved from resin and used without further purification).

B) Cyclic Peptide Synthesis:

(SEQ ID NO: 67)
Cyclo[Leu-His-Asn-Leu-NH-(CH$_2$)$_5$-CO-Thr-Glu-Arg-Met-Ala]

Prepared as in Example 5B. Yield: 15 mg of the title compound.

MS: MW calc. 1179.42; MW obs. 1180.09 (M+1)+.

Example 12

Cyclo[Leu-His-Asn-Leu-NH—(CH$_2$)$_6$—CO-Leu-Glu-Arg-Met-Ala]

A) Linear Peptide Synthesis:

(SEQ ID NO: 12)
H$_2$N—(CH$_2$)$_6$—CO-Leu-Glu(tBu)-Arg(Pbf)-Met-Ala-Leu-His(Trt)-Asn(Trt)-Leu-OH

Prepared as in Example 8A, except that Fmoc-1-aminocyclopropane-1-carboxylic acid in step 9 was replaced with Fmoc-Leu-OH. Yield: 3.0 g (cleaved from resin and used without further purification).

B) Cyclic Peptide Synthesis:

(SEQ ID NO: 68)
Cyclo[Leu-His-Asn-Leu-NH-(CH$_2$)$_6$-CO-Leu-Glu-Arg-Met-Ala]

Prepared as in Example 5B. Yield: 24 mg of the title compound.
MS: MW calc. 1191.42; MW obs. 1192.13 (M+1)⁺.

Example 13

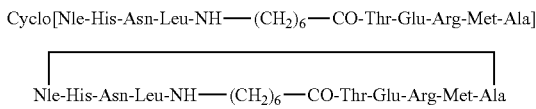

A) Linear Peptide Synthesis:

(SEQ ID NO: 13)
H₂N-Thr(tBu)-Glu(tBu)-Arg(Pbf)-Met-Ala-Nle-His(Trt)-Asn(Trt)-Leu-NH-(CH₂)₆-CO-OH

Starting material: 2-Chlorotrityl chloride resin
Resin attachment: DIEA/DCM (1. step)
Coupling: DIC/HOBt (2. step-10. step)
Deprotection: Piperidine
Cleavage from resin: HFIP
1. Step: Fmoc-NH—(CH₂)₆—CO—OH
2. Step: Fmoc-Leu-OH
3. Step: Fmoc-Asn(Trt)-OH
4. Step: Fmoc-His(Trt)-OH
5. Step: Fmoc-Nle-OH
6. Step: Fmoc-Ala-OH
7. Step: Fmoc-Met-OH
8. Step: Fmoc-Arg(Pbf)-OH
9. Step: Fmoc-Glu(tBu)-OH
10. Step: Fmoc-Thr(tBu)OH Yield: 3.44 g (cleaved from resin and used without further purification)

B) Cyclic Peptide Synthesis:

(SEQ ID NO: 69)
Cyclo[Nle-His-Asn-Leu-NH-(CH₂)₆-CO-Thr-Glu-Arg-Met-Ala]

Prepared as in Example 5B. Yield: 10 mg of the title compound.
MS: MW calc. 1193.44; MW obs. 1194.11 (M+1)⁺.

Example 14

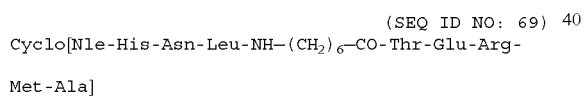

A) Linear Peptide Synthesis:

(SEQ ID NO: 14)
H₂N-Thr(tBu)-Glu(tBu)-Arg(Pbf)-Met-Ala-Ile-His(Trt)-Asn(Trt)-Leu-NH-(CH₂)₆-CO-OH

Prepared as in Example 13A, except that Fmoc-norleucine (Fmoc-Nle-OH) in step 5 was replaced with Fmoc-isoleucine. Yield: 2.33 g (cleaved from resin and used without further purification).

B) Cyclic Peptide Synthesis:

(SEQ ID NO: 70)
Cyclo[Ile-His-Asn-Leu-NH-(CH₂)₆-CO-Thr-Glu-Arg-Met-Ala]

Prepared as in Example 5B. Yield: 25 mg of the title compound.
MS: MW calc. 1193.44; MW obs. 1194.11 (M+1)⁺.

Example 15

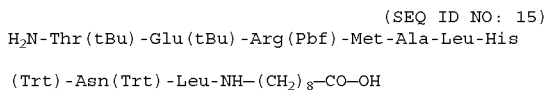

A) Linear Peptide Synthesis:

(SEQ ID NO: 15)
H₂N-Thr(tBu)-Glu(tBu)-Arg(Pbf)-Met-Ala-Leu-His(Trt)-Asn(Trt)-Leu-NH-(CH₂)₈-CO-OH

Prepared as in Example 13A, except that Fmoc-7-aminoheptanoic acid in step 1 was replaced with Fmoc-9-aminononanoic acid and Fmoc-norleucine in step 5 was replaced with Fmoc-leucine. Yield: 2.33 g (cleaved from resin and used without further purification).

B) Cyclic Peptide Synthesis:

(SEQ ID NO: 71)
Cyclo[Leu-His-Asn-Leu-NH-(CH₂)₈-CO-Thr-Glu-Arg-Met-Ala]

Prepared as in Example 5B. Yield: 72 mg of the title compound.
MS: MW calc. 1221.50; MW obs. 1222.17 (M+1)⁺.

Example 16

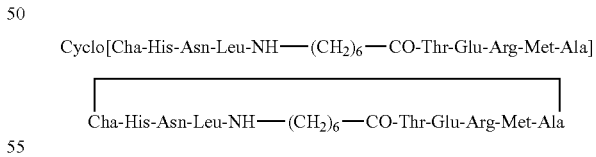

A) Linear Peptide Synthesis:

(SEQ ID NO: 16)
H₂N-Thr(tBu)-Glu(tBu)-Arg(Pbf)-Met-Ala-Cha-His(Trt)-Asn(Trt)-Leu-NH-(CH₂)₈-CO-OH

Prepared as in Example 13A, except that Fmoc-norleucine in step 5 was replaced with Fmoc-cyclohexylalanine (Fmoc-Cha-OH). Yield: 2.33 g (cleaved from resin and used without further purification).

B) Cyclic Peptide Synthesis:

(SEQ ID NO: 72)
Cyclo[Cha-His-Asn-Leu-NH-(CH$_2$)$_6$-CO-Thr-Glu-Arg-Met-Ala]

Prepared as in Example 5B. Yield: 35 mg of the title compound.
MS: MW calc. 1233.51; MW obs. 1234.13 (M+1)$^+$.

Example 17

Cyclo[Leu-His-Asn-Leu-NH—(CH$_2$)$_6$—CO-Thr-Glu-Arg-Cha-Ala]

Leu-His-Asn-Leu-NH—(CH$_2$)$_6$—CO-Thr-Glu-Arg-Cha-Ala

A) Linear Peptide Synthesis:

(SEQ ID NO: 17)
H$_2$N-Thr(tBu)-Glu(tBu)-Arg(Pbf)-Cha-Ala-Leu-His(Trt)-Asn(Trt)-Leu-NH-(CH$_2$)$_6$-CO-OH

Prepared as in Example 13A, except that Fmoc-norleucine in step 5 was replaced with Fmoc-leucine and Fmoc-methionine in step 7 was replaced with Fmoc-cyclohexylalanine (Fmoc-Cha-OH). Yield: 0.65 g (cleaved from resin and used without further purification).

B) Cyclic Peptide Synthesis:

(SEQ ID NO: 73)
Cyclo[Leu-His-Asn-Leu-NH-(CH$_2$)$_6$-CO-Thr-Glu-Arg-Cha-Ala]

Prepared as in Example 5B. Yield: 33 mg of the title compound.
MS: MW calc. 1215.47; MW obs. 1216.29 (M+1)$^+$.

Example 18

Cyclo[Leu-His-Asn-Leu-NH—(CH$_2$)$_6$—CO-Thr-Glu-Arg-Ile-Ala]

Leu-His-Asn-Leu-NH—(CH$_2$)$_6$—CO-Thr-Glu-Arg-Ile-Ala

A) Linear Peptide Synthesis:

(SEQ ID NO: 18)
H$_2$N-Thr(tBu)-Glu(tBu)-Arg(Pbf)-Ile-Ala-Leu-His(Trt)-Asn(Trt)-Leu-NH-(CH$_2$)$_6$-CO-OH

Prepared as in Example 17A, except that Fmoc-cyclohexylalanine in step 7 was replaced with Fmoc-isoleucine. Yield: 0.69 g (cleaved from resin and used without further purification).

B) Cyclic Peptide Synthesis:

(SEQ ID NO: 74)
Cyclo[Leu-His-Asn-Leu-NH-(CH$_2$)$_6$-CO-Thr-Glu-Arg-Ile-Ala]

Prepared as in Example 5B. Yield: 19 mg of the title compound.
MS: MW calc. 1175.41; MW obs. 1176.22 (M+1)$^+$.

Example 19

Cyclo[Nva-His-Asn-Leu-NH—(CH$_2$)$_6$—CO-Thr-Glu-Arg-Met-Ala]

Nva-His-Asn-Leu-NH—(CH$_2$)$_6$—CO-Thr-Glu-Arg-Met-Ala

A) Linear Peptide Synthesis:

(SEQ ID NO: 19)
H$_2$N-Thr(tBu)-Glu(tBu)-Arg(Pbf)-Met-Ala-Nva-His(Trt)-Asn(Trt)-Leu-NH-(CH$_2$)$_6$-CO-OH

Prepared as in Example 13A, except that Fmoc-norleucine in step 5 was replaced with Fmoc-norvaline (Fmoc-Nva-OH). Yield: 4.6 g (cleaved from resin and used without further purification).

B) Cyclic Peptide Synthesis:

(SEQ ID NO: 75)
Cyclo[Nva-His-Asn-Leu-NH-(CH$_2$)$_6$-CO-Thr-Glu-Arg-Met-Ala]

Prepared as in Example 5B. Yield: 42 mg of the title compound.
MS: MW calc. 1179.42; MW obs. 1180.15 (M+1)$^+$.

Example 20

Cyclo[Chg-His-Asn-Leu-NH—(CH$_2$)$_6$—CO-Thr-Glu-Arg-Met-Ala]

Chg-His-Asn-Leu-NH—(CH$_2$)$_6$—CO-Thr-Glu-Arg-Met-Ala

A) Linear Peptide Synthesis:

(SEQ ID NO: 20)
H$_2$N-Thr(tBu)-Glu(tBu)-Arg(Pbf)-Met-Ala-Chg-His(Trt)-Asn(Trt)-Leu-NH-(CH$_2$)$_6$-CO-OH

Prepared as in Example 13A, except that Fmoc-norleucine in step 5 was replaced with Fmoc-cyclohexylglycine (Fmoc-Chg-OH). Yield: 4.1 g (cleaved from resin and used without further purification).

B) Cyclic Peptide Synthesis:

(SEQ ID NO: 76)
Cyclo[Chg-His-Asn-Leu-NH-(CH$_2$)$_6$-CO-Thr-Glu-Arg-Met-Ala]

Prepared as in Example 5B. Yield: 24 mg of the title compound.
MS: MW calc. 1219.48; MW obs. 1220.17 (M+1)+.

Example 21

Cyclo[Leu-His-Asn-Leu-NH—(CH₂)₆—CO-His-Glu-Arg-Met-Ala]

Leu-His-Asn-Leu-NH—(CH₂)₆—CO-His-Glu-Arg-Met-Ala

A) Linear Peptide Synthesis:

(SEQ ID NO: 21)
H₂N-His(Trt)-Glu(tBu)-Arg(Pbf)-Met-Ala-Leu-

His(Trt)-Asn(Trt)-Leu-NH-(CH₂)₆-CO-OH

Prepared as in Example 13A, except that Fmoc-norleucine in step 5 was replaced with Fmoc-leucine and Fmoc-Thr(tBu)-OH in step 10 was replaced with Fmoc-His(Trt)-OH. Yield: 0.205 g (cleaved from resin and used without further purification).

B) Cyclic Peptide Synthesis:

(SEQ ID NO: 77)
Cyclo[Leu-His-Asn-Leu-NH-(CH₂)₆-CO-His-Glu-Arg-

Met-Ala]

Prepared as in Example 5B. Yield: 6.4 mg of the title compound.
MS: MW calc. 1229.48; MW obs. 1230.23 (M+1)+.

Example 22

Cyclo[Leu-His-Asn-Leu-NH—(CH₂)₆—CO-Asn-Glu-Arg-Met-Ala]

Leu-His-Asn-Leu-NH—(CH₂)₆—CO-Asn-Glu-Arg-Met-Ala

A) Linear Peptide Synthesis:

(SEQ ID NO: 22)
H₂N-Asn(Trt)-Glu(tBu)-Arg(Pbf)-Met-Ala-Leu-

His(Trt)-Asn(Trt)-Leu-NH-(CH₂)₆-CO-OH

Prepared as in Example 13A, except that Fmoc-norleucine in step 5 was replaced with Fmoc-leucine and Fmoc-Thr(tBu)-OH in step 10 was replaced with Fmoc-Asn(Trt)-OH. Yield: 0.194 g (cleaved from resin and used without further purification).

B) Cyclic Peptide Synthesis:

(SEQ ID NO: 78)
Cyclo[Leu-His-Asn-Leu-NH-(CH₂)₆-CO-Asn-Glu-

Arg-Met-Ala]

Prepared as in Example 5B. Yield: 8.3 mg of the title compound.
MS: MW calc. 1206.44; MW obs. 1207.16 (M+1)+.

Example 23

Cyclo[Leu-His-Asn-Leu-NH—(CH₂)₂—CO-Gly-Thr-Glu-Arg-Met-Ala]

Leu-His-Asn-Leu-NH—(CH₂)₂—CO-Gly-Thr-Glu-Arg-Met-Ala

A) Linear Peptide Synthesis:

(SEQ ID NO: 23)
H₂N-Gly-Thr(tBu)-Glu(tBu)-Arg(Pbf)-Met-Ala-Leu-

His(Trt)-Asn(Trt)-Leu-NH-(CH₂)₂-CO-OH

Starting material: 2-Chlorotrityl chloride resin
Resin attachment: DIEA/DCM (1. step)
Coupling: DIC/HOBt (2. step-11. step)
Deprotection: Piperidine
Cleavage from resin: HFIP
1. Step: Fmoc-NH—(CH₂)₂—CO—OH
2. Step: Fmoc-Leu-OH
3. Step: Fmoc-Asn(Trt)-OH
4. Step: Fmoc-His(Trt)-OH
5. Step: Fmoc-Leu-OH
6. Step: Fmoc-Ala-OH
7. Step: Fmoc-Met-OH
8. Step: Fmoc-Arg(Pbf)-OH
9. Step: Fmoc-Glu(tBu)-OH
10. Step: Fmoc-Thr(tBu)-OH
11. Step: Fmoc-Gly-OH
Yield: 1.88 g (cleaved from resin and used without further purification)

B) Cyclic Peptide Synthesis:

(SEQ ID NO: 79)
Cyclo[Leu-His-Asn-Leu-NH-(CH₂)₂-CO-Gly-Thr-

Glu-Arg-Met-Ala]

Prepared as in Example 5B. Yield: 16 mg of the title compound.
MS: MW calc. 1194.39; MW obs. 1195.10 (M+1)+.

Example 24

Cyclo[Leu-His-Asn-Leu-NH—(CH₂)₆—CO-Dbu-Glu-Arg-Met-Ala]

Leu-His-Asn-Leu-NH—(CH₂)₆—CO-Dbu-Glu-Arg-Met-Ala

A) Linear Peptide Synthesis:

(SEQ ID NO: 24)
H₂N-Dbu(Boc)-Glu(tBu)-Arg(Pbf)-Met-Ala-Leu-

His(Trt)-Asn(Trt)-Leu-NH-(CH₂)₆-CO-OH

Prepared as in Example 13A, except that Fmoc-norleucine in step 5 was replaced with Fmoc-leucine and Fmoc-Thr (tBu)-OH in step 10 was replaced with N-alpha-Fmoc-N-gamma-Boc-2,4-diamino-butyric acid (Fmoc-Dbu(Boc)-OH). Yield: 0.199 g (cleaved from resin and used without further purification).

B) Cyclic Peptide Synthesis:

(SEQ ID NO: 80)
Cyclo[Leu-His-Asn-Leu-NH—(CH₂)₆—CO-Dbu-Glu-Arg-Met-Ala]

Prepared as in Example 5B. Yield: 12.8 mg of the title compound.

MS: MW calc. 1192.46; MW obs. 1193.12 (M+1)⁺.

Example 25

Cyclo[Leu-His-Asn-Leu-NH——(CH₂)₆—CO-Gln-Glu-Arg-Met-Ala]

Leu-His-Asn-Leu-NH——(CH₂)₆—CO-Gln-Glu-Arg-Met-Ala

A) Linear Peptide Synthesis:

(SEQ ID NO: 25)
H₂N-Leu-His(Boc)-Asn(Trt)-Leu-NH—(CH₂)₆—CO-Gln(Trt)-Glu(tBu)-Arg(Pbf)-Met-Ala-OH

Prepared as in Example 1A, except that Fmoc-Thr(tBu)-OH in step 5 was replaced with Fmoc-Gln-OH. Crude product used in next step without further purification.

B) Cyclic Peptide Synthesis:

(SEQ ID NO: 81)
Cyclo[Leu-His-Asn-Leu-NH—(CH₂)₆—CO-Gln-Glu-Arg-Met-Ala]

Prepared as in Example 1B. Yield: 11.5 mg of the title compound.

MS: MW calc. 1220.47; MW obs. 1221.05 (M+1)⁺.

Example 26

Cyclo[Leu-His-Asn-Leu-NH——(CH₂)₆—CO-Ser-Glu-Arg-Met-Ala]

Leu-His-Asn-Leu-NH——(CH₂)₆—CO-Ser-Glu-Arg-Met-Ala

A) Linear Peptide Synthesis:

(SEQ ID NO: 26)
H₂N-Leu-His(Boc)-Asn(Trt)-Leu-NH—(CH₂)₆—CO-Ser(tBu)-Glu(tBu)-Arg(Pbf)-Met-Ala-OH

Prepared as in Example 1A, except that Fmoc-Thr(tBu)-OH in step 5 was replaced with Fmoc-Ser(tBu)-OH. Crude product used in next step without further purification.

B) Cyclic Peptide Synthesis:

(SEQ ID NO: 82)
Cyclo[Leu-His-Asn-Leu-NH—(CH₂)₆—CO-Ser-Glu-Arg-Met-Ala]

Prepared as in Example 1B. Yield: 11.0 mg of the title compound.

MS: MW calc. 1191.47; MW obs. 1191.96 (M+1)⁺.

Example 27

Cyclo[Leu-His-Asn-Leu-NH——(CH₂)₆—CO-Val-Glu-Arg-Met-Ala]

Leu-His-Asn-Leu-NH——(CH₂)₆—CO-Val-Glu-Arg-Met-Ala

A) Linear Peptide Synthesis:

(SEQ ID NO: 27)
H₂N-Leu-His(Boc)-Asn(Trt)-Leu-NH—(CH₂)₆—CO-Val-Glu(tBu)-Arg(Pbf)-Met-Ala-OH

Prepared as in Example 1A, except that Fmoc-Thr(tBu)-OH in step 5 was replaced with Fmoc-Val-OH. Crude product used in next step without further purification.

B) Cyclic Peptide Synthesis:

(SEQ ID NO: 83)
Cyclo[Leu-His-Asn-Leu-NH—(CH₂)₆—CO-Val-Glu-Arg-Met-Ala]

Prepared as in Example 1B. Yield: 25.6 mg of the title compound.

MS: MW calc. 1179.42; MW obs. 1180.09 (M+1)⁺.

Example 28

Cyclo[Leu-His-Asn-Leu-NH——(CH₂)₆—CO-Thr-Glu-Orn-Met-Ala]

Leu-His-Asn-Leu-NH——(CH₂)₆—CO-Thr-Glu-Orn-Met-Ala

A) Linear Peptide Synthesis:

(SEQ ID NO: 28)
H₂N-Leu-His(Boc)-Asn-Leu-NH—(CH₂)₆—CO-Thr(tBu)-Glu(tBu)-Orn(Boc)-Met-Ala-OH

Prepared as in Example 1A, except that Fmoc-Arg(Pbf)-OH in step 3 was replaced with Fmoc-Orn(Boc)-OH. Crude product used in next step without further purification.

B) Cyclic Peptide Synthesis:

(SEQ ID NO: 84)
Cyclo[Leu-His-Asn-Leu-NH—(CH₂)₆—CO-Thr-Glu-Orn-Met-Ala]

Prepared as in Example 1B. Yield: 15.0 mg of the title compound.

MS: MW calc. 1151.40; MW obs. 1152.07 (M+1)+.

Example 29

Cyclo[Leu-His-Asn-Leu-NH—(CH$_2$)$_6$—CO-Thr-Glu-Dpr-Met-Ala]
|
Leu-His-Asn-Leu-NH—(CH$_2$)$_6$—CO-Thr-Glu-Dpr-Met-Ala A) Linear Peptide Synthesis:

(SEQ ID NO: 29)
H$_2$N-Leu-His(Boc)-Asn-Leu-NH-(CH$_2$)$_6$-CO-Thr(tBu)-Glu(tBu)-Dpr(Boc)-Met-Ala-OH

Prepared as in Example 1A, except that Fmoc-Arg(Pbf)-OH in step 3 was replaced with Fmoc-Dpr(Boc)-OH. Crude product used in next step without further purification.

B) Cyclic Peptide Synthesis:

(SEQ ID NO: 85)
Cyclo[Leu-His-Asn-Leu-NH-(CH$_2$)$_6$-CO-Thr-Glu-Dpr-Met-Ala]

Prepared as in Example 1B. Yield: 26.3 mg of the title compound.

MS: MW calc. 1123.35; MW obs. 1124.00 (M+1)+.

Example 30

Cyclo[Leu-His-Asn-Leu-NH—(CH$_2$)$_6$—CO-Thr-Glu-Arg-Met-Arg]
|
Leu-His-Asn-Leu-NH—(CH$_2$)$_6$—CO-Thr-Glu-Arg-Met-Arg A) Linear Peptide Synthesis:

(SEQ ID NO: 30)
H$_2$N-(CH$_2$)$_6$-CO-Thr(tBu)-Glu(tBu)-Arg(Pbf)-Met-Arg(Pbf)-Leu-His(Trt)-Asn(Trt)-Leu-OH

Prepared as in Example 5A, except that Fmoc-Ala-OH in step 5 was replaced with Fmoc-Arg(Trt)-OH and Ac-Lys(Fmoc)-OH in step 10 was replaced with Fmoc-7-amino-heptanoic acid. Crude product used in next step without further purification.

B) Cyclic Peptide Synthesis:

(SEQ ID NO: 86)
Cyclo[Leu-His-Asn-Leu-NH-(CH$_2$)$_6$-CO-Thr-Glu-Arg-Met-Arg]

Prepared as in Example 5B. Yield: 32.7 mg of the title compound.

MS: MW calc. 1278.55; MW obs. 1279.73 (M+1)+.

Example 31

Cyclo[Leu-His-Asn-Leu-NH—(CH$_2$)$_6$—CO-Thr-Glu-Arg-Met-Nva]
|
Leu-His-Asn-Leu-NH—(CH$_2$)$_6$—CO-Thr-Glu-Arg-Met-Nva A) Linear Peptide Synthesis:

(SEQ ID NO: 31)
H$_2$N-(CH$_2$)$_6$-CO-Thr(tBu)-Glu(tBu)-Arg(Pbf)-Met-Nva-Leu-His(Trt)-Asn(Trt)-Leu-OH

Prepared as in Example 5A, except that Fmoc-Ala-OH in step 5 was replaced with Fmoc-Nva-OH and Ac-Lys(Fmoc)-OH in step 10 was replaced with Fmoc-7-amino-heptanoic acid. Crude product used in next step without further purification.

B) Cyclic Peptide Synthesis:

(SEQ ID NO: 87)
Cyclo[Leu-His-Asn-Leu-NH-(CH$_2$)$_6$-CO-Thr-Glu-Arg-Met-Nva]

Prepared as in Example 5B. Yield: 29.2 mg of the title compound.

MS: MW calc. 1221.50; MW obs. 1222.63 (M+1)+.

Example 32

Cyclo[Leu-His-Asn-Leu-NH—(CH$_2$)$_6$—CO-Thr-Glu-Arg-Met-Dpa]
|
Leu-His-Asn-Leu-NH—(CH$_2$)$_6$—CO-Thr-Glu-Arg-Met-Dpr A) Linear Peptide Synthesis:

(SEQ ID NO: 32)
H$_2$N-(CH$_2$)$_6$-CO-Thr(tBu)-Glu(tBu)-Arg(Pbf)-Met-Dpr(Boc)-Leu-His(Trt)-Asn(Trt)-Leu-OH

Prepared as in Example 5A, except that Fmoc-Ala-OH in step 5 was replaced with Fmoc-Dpr(Boc)-OH and Ac-Lys(Fmoc)-OH in step 10 was replaced with Fmoc-7-amino-heptanoic acid. Crude product used in next step without further purification.

B) Cyclic Peptide Synthesis:

(SEQ ID NO: 88)
Cyclo[Leu-His-Asn-Leu-NH-(CH$_2$)$_6$-CO-Thr-Glu-Arg-Met-Dpr]

Prepared as in Example 5B. Yield: 41.2 mg of the title compound.
MS: MW calc. 1208.46; MW obs. 1209.61 (M+1)⁺.

Example 33

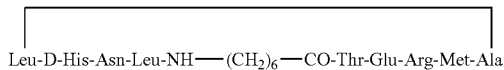

A) Linear Peptide Synthesis:

(SEQ ID NO: 33)
H₂N-(CH₂)₆-CO-Thr(tBu)-Glu(tBu)-Arg(Pbf)-Met-Ala-
Leu-D-His(Trt)-Asn(Trt)-Leu-OH

Prepared as in Example 5A, except that Fmoc-His(Trt)-OH in step 3 was replaced with Fmoc-D-His(Trt)-OH and Ac-Lys(Fmoc)-OH in step 10 was replaced with Fmoc-7-amino-heptanoic acid. Crude product used in next step without further purification.

B) Cyclic Peptide Synthesis:

(SEQ ID NO: 89)
Cyclo[Leu-D-His-Asn-Leu-NH-(CH₂)₆-CO-Thr-Glu-Arg-
Met-Ala]

Prepared as in Example 5B. Yield: 29.5 mg of the title compound.
MS: MW calc. 1193.44; MW obs. 1194.45 (M+1)⁺.

Example 34

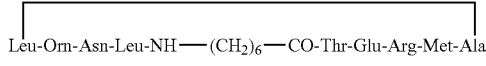

A) Linear Peptide Synthesis:

(SEQ ID NO: 34)
H₂N-(CH₂)₆-CO-Thr(tBu)-Glu(tBu)-Arg(Pbf)-Met-Ala-
Leu-Orn(Boc)-Asn(Trt)-Leu-OH

Prepared as in Example 5A, except that Fmoc-His(Trt)-OH in step 3 was replaced with Fmoc-Orn(Boc)-OH and Ac-Lys(Fmoc)-OH in step 10 was replaced with Fmoc-7-amino-heptanoic acid. Crude product used in next step without further purification.

B) Cyclic Peptide Synthesis:

(SEQ ID NO: 90)
Cyclo[Leu-Orn-Asn-Leu-NH-(CH₂)₆-CO-Thr-Glu-Arg-
Met-Ala]

Prepared as in Example 5B. Yield: 38.5 mg of the title compound.
MS: MW calc. 1170.45; MW obs. 1171.54 (M+1)⁺.

Example 35

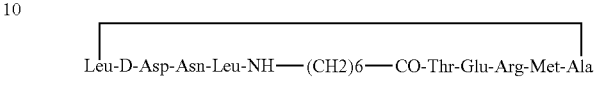

A) Linear Peptide Synthesis:

(SEQ ID NO: 35)
H₂N-(CH₂)₆-CO-Thr(tBu)-Glu(tBu)-Arg(Pbf)-Met-Ala-
Leu-D-Asp(tBu)-Asn(Trt)-Leu-OH

Prepared as in Example 5A, except that Fmoc-His(Trt)-OH in step 3 was replaced with Fmoc-D-Asp(tBu)-OH and Ac-Lys(Fmoc)-OH in step 10 was replaced with Fmoc-7-amino-heptanoic acid. Crude product used in next step without further purification.

B) Cyclic Peptide Synthesis:

(SEQ ID NO: 91)
Cyclo[Leu-D-Asp-Asn-Leu-NH-(CH₂)₆-CO-Thr-Glu-Arg-
Met-Ala]

Prepared as in Example 5B. Yield: 36.7 mg of the title compound.
MS: MW calc. 1171.39; MW obs. 1172.41 (M+1)⁺.

Example 36

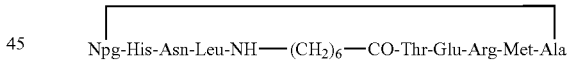

A) Linear Peptide Synthesis:

(SEQ ID NO: 36)
H₂N-(CH₂)₆-CO-Thr(tBu)-Glu(tBu)-Arg(Pbf)-Met-Ala-
Npg-His(Trt)-Asn(Trt)-Leu-OH

Prepared as in Example 5A, except that Fmoc-Leu-OH in step 4 was replaced with Fmoc-neopentylglycine (Fmoc-Npg-OH) and Ac-Lys(Fmoc)-OH in step 10 was replaced with Fmoc-7-amino-heptanoic acid. Crude product used in next step without further purification.

B) Cyclic Peptide Synthesis:

(SEQ ID NO: 92)
Cyclo[Npg-His-Asn-Leu-NH-(CH₂)₆-CO-Thr-Glu-Arg-
Met-Ala]

Example 37

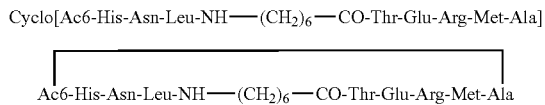

A) Linear Peptide Synthesis:

(SEQ ID NO: 37)
H₂N-(CH₂)₆-CO-Thr(tBu)-Glu(tBu)-Arg(Pbf)-Met-Ala-
Ac6-His(Trt)-Asn(Trt)-Leu-OH

Prepared as in Example 5A, except that Fmoc-Leu-OH in step 4 was replaced with Fmoc-1-aminocyclohexane-1-carboxylic acid (Fmoc-Ac6-OH) and Ac-Lys(Fmoc)-OH in step 10 was replaced with Fmoc-7-amino-heptanoic acid. Crude product used in next step without further purification.

B) Cyclic Peptide Synthesis:

(SEQ ID NO: 93)
Cyclo[Ac6-His-Asn-Leu-NH-(CH₂)₆-CO-Thr-Glu-Arg-Met-Ala]

Prepared as in Example 5B. Yield: 15.1 mg of the title compound.
MS: MW calc. 1205.46; MW obs. 1206.57 (M+1)⁺.

Example 38

Cyclo[Leu-His-Asn-Leu-NH—(CH₂)₆—CO-Thr-Glu-Arg-Leu-Ala]

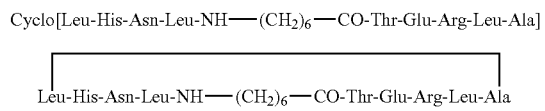

A) Linear Peptide Synthesis:

(SEQ ID NO: 38)
H₂N-(CH₂)₆-CO-Thr(tBu)-Glu(tBu)-Arg(Pbf)-Leu-Ala-
Leu-His(Trt)-Asn(Trt)-Leu-OH

Prepared as in Example 5A, except that Fmoc-Met-OH in step 6 was replaced with Fmoc-Leu-OH and Ac-Lys(Fmoc)-OH in step 10 was replaced with Fmoc-7-amino-heptanoic acid. Crude product used in next step without further purification.

B) Cyclic Peptide Synthesis:

(SEQ ID NO: 94)
Cyclo[Leu-His-Asn-Leu-NH-(CH₂)₆-CO-Thr-Glu-Arg-Leu-Ala]

Prepared as in Example 5B. Yield: 23.4 mg of the title compound.
MS: MW calc. 1207.47; MW obs. 1208.56 (M+1)⁺.

Example 39

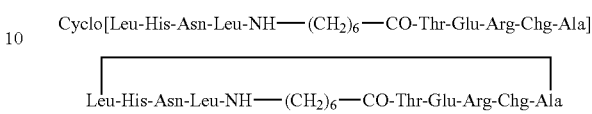

A) Linear Peptide Synthesis:

(SEQ ID NO: 39)
H₂N-(CH₂)₆-CO-Thr(tBu)-Glu(tBu)-Arg(Pbf)-Chg-Ala-
Leu-His(Trt)-Asn(Trt)-Leu-OH

Prepared as in Example 5A, except that Fmoc-Met-OH in step 6 was replaced with Fmoc-Chg and Ac-Lys(Fmoc)-OH in step 10 was replaced with Fmoc-7-amino-heptanoic acid. Crude product used in next step without further purification.

B) Cyclic Peptide Synthesis:

(SEQ ID NO: 95)
Cyclo[Leu-His-Asn-Leu-NH-(CH₂)₆-CO-Thr-Glu-Arg-Chg-Ala]

Prepared as in Example 5B. Yield: 14.6 mg of the title compound.
MS: MW calc. 1201.45; MW obs. 1202.10 (M+1)⁺.

Example 40

Cyclo[Leu-His-Asn-Leu-NH—(CH₂)₆—CO-Thr-Glu-Arg-Ala-Ala]

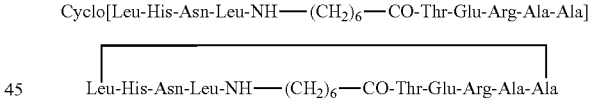

A) Linear Peptide Synthesis:

(SEQ ID NO: 40)
H₂N-(CH₂)₆-CO-Thr(tBu)-Glu(tBu)-Arg(Pbf)-Ala-Ala-
Leu-His(Trt)-Asn(Trt)-Leu-OH

Prepared as in Example 5A, except that Fmoc-Met-OH in step 6 was replaced with Fmoc-Ala-OH and Ac-Lys(Fmoc)-OH in step 10 was replaced with Fmoc-7-amino-heptanoic acid. Crude product used in next step without further purification.

B) Cyclic Peptide Synthesis:

(SEQ ID NO: 96)
Cyclo[Leu-His-Asn-Leu-NH-(CH₂)₆-CO-Thr-Glu-Arg-Ala-Ala]

Prepared as in Example 5B. Yield: 23.2 mg of the title compound.
MS: MW calc. 1175.41; MW obs. 1176.61 (M+1)⁺.

Prepared as in Example 5B. Yield: 75.9 mg of the title compound.
MS: MW calc. 1133.33; MW obs. 1134.48 (M+1)⁺.

Example 41

Cyclo[Leu-His-Asn-Leu-NH—(CH₂)₆—CO-Thr-Glu-Arg-Gln-Ala]
|_____|
Leu-His-Asn-Leu-NH—(CH₂)₆—CO-Thr-Glu-Arg-Gln-Ala A) Linear Peptide Synthesis:

(SEQ ID NO: 41)
H₂N—(CH₂)₆—CO-Thr(tBu)-Glu(tBu)-Arg(Pbf)-Gln(Trt)-
Ala-Leu-His(Trt)-Asn(Trt)-Leu-OH

Prepared as in Example 5A, except that Fmoc-Met-OH in step 6 was replaced with Fmoc-Gln(Trt)-OH and Ac-Lys(Fmoc)-OH in step 10 was replaced with Fmoc-7-amino-heptanoic acid. Crude product used in next step without further purification.

B) Cyclic Peptide Synthesis:

(SEQ ID NO: 97)
Cyclo[Leu-His-Asn-Leu-NH—(CH₂)₆—CO-Thr-Glu-Arg-
Gln-Ala]

Prepared as in Example 5B. Yield: 55.3 mg of the title compound.
MS: MW calc. 1190.38; MW obs. 1191.49 (M+1)⁺.

Example 42

Cyclo[Leu-His-Asn-Leu-NH—(CH₂)₆—CO-Thr-Glu-Arg-Abu-Ala]
|_____|
Leu-His-Asn-Leu-NH—(CH₂)₆—CO-Thr-Glu-Arg-Abu-Ala A) Linear Peptide Synthesis:

(SEQ ID NO: 42)
H₂N—(CH₂)₆—CO-Thr(tBu)-Glu(tBu)-Arg(Pbf)-Abu-
Ala-Leu-His(Trt)-Asn(Trt)-Leu-OH

Prepared as in Example 5A, except that Fmoc-Met-OH in step 6 was replaced with Fmoc-Abu-OH and Ac-Lys(Fmoc)-OH in step 10 was replaced with Fmoc-7-amino-heptanoic acid. Crude product used in next step without further purification.

B) Cyclic Peptide Synthesis:

(SEQ ID NO: 98)
Cyclo[Leu-His-Asn-Leu-NH—(CH₂)₆—CO-Thr-Glu-
Arg-Abu-Ala]

Prepared as in Example 5B. Yield: 41.3 mg of the title compound.
MS: MW calc. 1147.35; MW obs. 1148.52 (M+1)⁺.

Example 43

Cyclo[Leu-His-Asn-Leu-NH—(CH₂)₆—CO-Thr-Glu-Arg-Nle-Ala]
|_____|
Leu-His-Asn-Leu-NH—(CH₂)₆—CO-Thr-Glu-Arg-Nle-Ala A) Linear Peptide Synthesis:

(SEQ ID NO: 43)
H₂N—(CH₂)₆—CO-Thr(tBu)-Glu(tBu)-Arg(Pbf)-Nle-
Ala-Leu-His(Trt)-Asn(Trt)-Leu-OH

Prepared as in Example 5A, except that Fmoc-Met-OH in step 6 was replaced with Fmoc-norleucine (Fmoc-Nle-OH) and Ac-Lys(Fmoc)-OH in step 10 was replaced with Fmoc-7-amino-heptanoic acid. Crude product used in next step without further purification.

B) Cyclic Peptide Synthesis:

(SEQ ID NO: 99)
Cyclo[Leu-His-Asn-Leu-NH—(CH₂)₆—CO-Thr-Glu-
Arg-Nle-Ala]

Prepared as in Example 5B. Yield: 30.7 mg of the title compound.
MS: MW calc. 1175.41; MW obs. 1176.50 (M+1)⁺.

Example 44

Cyclo[Leu-His-Asn-Leu-NH—(CH₂)₆—CO-Thr-Glu-Arg-Amb-Ala]
|_____|
Leu-His-Asn-Leu-NH—(CH₂)₆—CO-Thr-Glu-Arg-Amb-Ala A) Linear Peptide Synthesis:

(SEQ ID NO: 44)
H₂N—(CH₂)₆—CO-Thr(tBu)-Glu(tBu)-Arg(Pbf)-Amb-
Ala-Leu-His(Trt)-Asn(Trt)-Leu-OH

Prepared as in Example 5A, except that Fmoc-Met-OH in step 6 was replaced with Fmoc-Amb-OH (Fmoc-L-2-amino-4-methoxybutyric acid) and Ac-Lys(Fmoc)-OH in step 10 was replaced with Fmoc-7-amino-heptanoic acid. Crude product used in next step without further purification.

B) Cyclic Peptide Synthesis:

(SEQ ID NO: 100)
Cyclo[Leu-His-Asn-Leu-NH—(CH₂)₆—CO-Thr-Glu-
Arg-Amb-Ala]

Prepared as in Example 5B. Yield: 28.1 mg of the title compound.

MS: MW calc. 1177.38; MW obs. 1178.58 (M+1)⁺.

Example 45

Cyclo[Leu-His-Asn-Leu-NH—(CH₂)₆—CO-Thr-Glu-Arg-Amp-Ala]
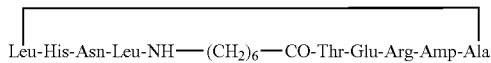
Leu-His-Asn-Leu-NH—(CH₂)₆—CO-Thr-Glu-Arg-Amp-Ala A) Linear Peptide Synthesis:

(SEQ ID NO: 45)
H₂N-(CH₂)₆-CO-Thr(tBu)-Glu(tBu)-Arg(Pbf)-Amp-Ala-Leu-His(Trt)-Asn(Trt)-Leu-OH

Prepared as in Example 5A, except that Fmoc-Met-OH in step 6 was replaced with Fmoc-Amp-OH (Fmoc-L-2-amino-3-methoxypropionic acid) and Ac-Lys(Fmoc)-OH in step 10 was replaced with Fmoc-7-amino-heptanoic acid. Crude product used in next step without further purification.

B) Cyclic Peptide Synthesis:

(SEQ ID NO: 101)
Cyclo[Leu-His-Asn-Leu-NH-(CH₂)₆-CO-Thr-Glu-Arg-Amp-Ala]

Prepared as in Example 5B. Yield: 29.5 mg of the title compound.

MS: MW calc. 1163.35; MW obs. 1164.53 (M+1)⁺.

Example 46

Cyclo[Leu-His-Asn-Leu-Gly-NH—(CH₂)₄—CO-Thr-Glu-Arg-Met-Ala]
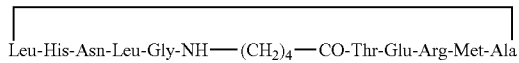
Leu-His-Asn-Leu-Gly-NH—(CH₂)₄—CO-Thr-Glu-Arg-Met-Ala A) Linear Peptide Synthesis:

(SEQ ID NO: 46)
H₂N-(CH₂)₄-CO-Thr(tBu)-Glu(tBu)-Arg(Pbf)-Met-Ala-Leu-His(Trt)-Asn(Trt)-Leu-Gly-OH

Prepared as in Example 5A, except that before step 1 an extra step with Fmoc-Gly-OH was inserted and Ac-Lys(Fmoc)-OH in step 10 was replaced with Fmoc-NH—(CH₂)₄—COOH. Crude product used in next step without further purification.

B) Cyclic Peptide Synthesis:

(SEQ ID NO: 102)
Cyclo[Leu-His-Asn-Leu-Gly-NH-(CH₂)₄-CO-Thr-Glu-Arg-Met-Ala]

Prepared as in Example 5B. Yield: 34.9 mg of the title compound.

MS: MW calc. 1222.44; MW obs. 1223.51 (M+1)⁺.

Example 47

Cyclo[Leu-His-Asn-Leu-NH—(CH₂)₉—CO-Thr-Glu-Arg-Met-Ala]
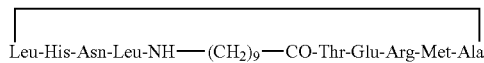
Leu-His-Asn-Leu-NH—(CH₂)₉—CO-Thr-Glu-Arg-Met-Ala A) Linear Peptide Synthesis:

(SEQ ID NO: 47)
H₂N-(CH₂)₉-CO-Thr(tBu)-Glu(tBu)-Arg(Pbf)-Met-Ala-Leu-His(Trt)-Asn(Trt)-Leu-OH

Prepared as in Example 5A, except that Ac-Lys(Fmoc)-OH in step 10 was replaced with Fmoc-NH—(CH₂)₉—COOH (crude product used in next step without further purification).

B) Cyclic Peptide Synthesis:

(SEQ ID NO: 103)
Cyclo[Leu-His-Asn-Leu-NH-(CH₂)₉-CO-Thr-Glu-Arg-Met-Ala]

Prepared as in Example 5B. Yield: 19.5 mg of the title compound.

MS: MW calc. 1235.53; MW obs. 1236.19 (M+1)⁺.

Example 48

Cyclo[Leu-His-Asn-Leu-Gly-NH—(CH₂)₃—CO-Thr-Glu-Arg-Met-Ala]
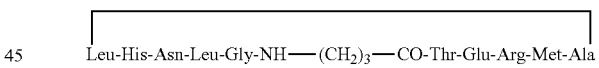
Leu-His-Asn-Leu-Gly-NH—(CH₂)₃—CO-Thr-Glu-Arg-Met-Ala A) Linear Peptide Synthesis:

(SEQ ID NO: 48)
H₂N-(CH₂)₃-CO-Thr(tBu)-Glu(tBu)-Arg(Pbf)-Met-Ala-Leu-His(Trt)-Asn(Trt)-Leu-Gly-OH

Prepared as in Example 5A, except that before step 1 an extra step with Fmoc-Gly-OH was inserted and Ac-Lys(Fmoc)-OH in step 10 was replaced with Fmoc-NH—(CH₂)₃—COOH. Crude product used in next step without further purification.

B) Cyclic Peptide Synthesis:

(SEQ ID NO: 104)
Cyclo[Leu-His-Asn-Leu-Gly-NH-(CH₂)₃-CO-Thr-Glu-Arg-Met-Ala]

Prepared as in Example 5B. Yield: 19.1 mg of the title compound.
MS: MW calc. 1208.42; MW obs. 1209.49 (M+1)⁺.

Example 49

Cyclo[Leu-His-Asn-Leu-Dpr-NH—(CH$_2$)$_3$—CO-Thr-Glu-Arg-Met-Ala]
|
Leu-His-Asn-Leu-Dpr-NH—(CH$_2$)$_3$—CO-Thr-Glu-Arg-Met-Ala A) Linear Peptide Synthesis:

(SEQ ID NO: 49)
H$_2$N-Dpr(Boc)-HN-(CH$_2$)$_3$-CO-Thr(tBu)-Glu(tBu)-

Arg(Pbf)-Met-Ala-Leu-His(Trt)-Asn(Trt)-Leu-OH

Prepared as in Example 5A, except that Ac-Lys(Fmoc)-OH in step 10 was replaced with Fmoc-NH—(CH$_2$)$_3$—COOH and afterwards an extra step with Fmoc-Dpr(Boc)-OH was inserted. Crude product used in next step without further purification.

B) Cyclic Peptide Synthesis:

(SEQ ID NO: 105)
Cyclo[Leu-His-Asn-Leu-Dpr-NH-(CH$_2$)$_3$-CO-

Thr-Glu-Arg-Met-Ala]

Prepared as in Example 5B. Yield: 18.2 mg of the title compound.
MS: MW calc. 1237.46; MW obs. 1238.62 (M+1)⁺.

Example 50

Cyclo[Leu-His-Asn-Leu-NH—(CH$_2$)$_3$—CO-Asn-Thr-Glu-Arg-Met-Ala]
|
Leu-His-Asn-Leu-NH—(CH$_2$)$_3$—CO-Asn-Thr-Glu-Arg-Met-Ala A) Linear Peptide Synthesis:

(SEQ ID NO: 50)
H$_2$N-(CH$_2$)$_3$-CO-Asn(Trt)-Thr(tBu)-Glu(tBu)-

Arg(Pbf)-Met-Ala-Leu-His(Trt)-Asn(Trt)-Leu-OH

Prepared as in Example 5A, except that an additional step with Fmoc-Asn(Trt)-OH was inserted after step 9 and Ac-Lys(Fmoc)-OH in step 10 was replaced with Fmoc-NH—(CH$_2$)$_3$—COOH. Crude product used in next step without further purification.

B) Cyclic Peptide Synthesis:

(SEQ ID NO: 106)
Cyclo[Leu-His-Asn-Leu-NH-(CH$_2$)$_3$-CO-

Asn-Thr-Glu-Arg-Met-Ala]

Prepared as in Example 5B. Yield: 14.0 mg of the title compound.
MS: MW calc. 1265.47; MW obs. 1266.65 (M+1)⁺.

Example 51

Cyclo[Leu-His-Asn-Leu-NH—(CH$_2$)$_2$—CO-Asn-Thr-Glu-Arg-Met-Ala]
|
Leu-His-Asn-Leu-NH—(CH$_2$)$_2$—CO-Asn-Thr-Glu-Arg-Met-Ala A) Linear Peptide Synthesis:

(SEQ ID NO: 51)
H$_2$N-(CH$_2$)$_2$-CO-Asn(Trt)-Thr(tBu)-Glu(tBu)-Arg(Pbf)-

Met-Ala-Leu-His(Trt)-Asn(Trt)-Leu-OH

Prepared as in Example 5A, except that an additional step with Fmoc-Asn(Trt)-OH was inserted after step 9 and Ac-Lys(Fmoc)-OH in step 10 was replaced with Fmoc-NH—(CH$_2$)$_2$—COOH. Crude product used in next step without further purification.

B) Cyclic Peptide Synthesis:

(SEQ ID NO: 107)
Cyclo[Leu-His-Asn-Leu-NH-(CH$_2$)$_2$-CO-

Asn-Thr-Glu-Arg-Met-Ala]

Prepared as in Example 5B. Yield: 11.6 mg of the title compound.
MS: MW calc. 1251.44; MW obs. 1252.56 (M+1)⁺.

Example 52

Cyclo[Leu-His-Asn-Leu-NH—(CH$_2$)$_2$—CO-Ala-Thr-Glu-Arg-Met-Ala]
|
Leu-His-Asn-Leu-NH—(CH$_2$)$_2$—CO-Ala-Thr-Glu-Arg-Met-Ala A) Linear Peptide Synthesis:

(SEQ ID NO: 52)
H$_2$N-(CH$_2$)$_2$-CO-Ala-Thr(tBu)-Glu(tBu)-Arg(Pbf)-

Met-Ala-Leu-His(Trt)-Asn(Trt)-Leu-OH

Prepared as in Example 5A, except that an additional step with Fmoc-Ala-OH was inserted after step 9 and Ac-Lys(Fmoc)-OH in step 10 was replaced with Fmoc-NH—(CH$_2$)$_2$—COOH. Crude product used in next step without further purification.

B) Cyclic Peptide Synthesis:

(SEQ ID NO: 108)
Cyclo[Leu-His-Asn-Leu-NH-(CH$_2$)$_2$-CO-

Ala-Thr-Glu-Arg-Met-Ala]

Prepared as in Example 5B. Yield: 20.0 mg of the title compound.
MS: MW calc. 1222.44; MW obs. 1223.63 (M+1)$^+$.

Example 53

Cyclo[Leu-His-Asn-Leu-NH—(CH$_2$)$_3$—CO-Aib-Thr-Glu-Arg-Met-Ala]

Leu-His-Asn-Leu-NH—(CH$_2$)$_3$—CO-Aib-Thr-Glu-Arg-Met-Ala

A) Linear Peptide Synthesis:

(SEQ ID NO: 53)
H$_2$N—(CH$_2$)$_3$—CO-Aib-Thr(tBu)-Glu(tBu)-Arg(Pbf)-

Met-Ala-Leu-His(Trt)-Asn(Trt)-Leu-OH

Prepared as in Example 5A, except that an additional step with Fmoc-Aib-OH was inserted after step 9 and Ac-Lys(Fmoc)-OH in step 10 was replaced with Fmoc-NH—(CH$_2$)$_3$—COOH. Crude product used in next step without further purification.

B) Cyclic Peptide Synthesis:

(SEQ ID NO: 109)
Cyclo[Leu-His-Asn-Leu-NH—(CH$_2$)$_3$—CO-

Aib-Thr-Glu-Arg-Met-Ala]

Prepared as in Example 5B. Yield: 12.0 mg of the title compound.
MS: MW calc. 1236.47; MW obs. 1237.61 (M+1)$^+$.

Example 54

Cyclo[Leu-His-Asn-Leu-NH—(CH$_2$)$_3$—CO—Ac3-Thr-Glu-Arg-Met-Ala]

Leu-His-Asn-Leu-NH—(CH$_2$)$_3$—CO—Ac3-Thr-Glu-Arg-Met-Ala

A) Linear Peptide Synthesis:

(SEQ ID NO: 54)
H$_2$N—(CH$_2$)$_3$—CO-Ac3-Thr(tBu)-Glu(tBu)-Arg(Pbf)-

Met-Ala-Leu-His(Trt)-Asn(Trt)-Leu-OH

Prepared as in Example 5A, except that an additional step with Fmoc-1-aminocyclopropane-1-carboxylic acid (Fmoc-Ac3-OH) was inserted after step 9 and Ac-Lys(Fmoc)-OH in step 10 was replaced with Fmoc-NH—(CH$_2$)$_3$—COOH (crude product used in next step without further purification).

B) Cyclic Peptide Synthesis:

(SEQ ID NO: 110)
Cyclo[Leu-His-Asn-Leu-NH—(CH$_2$)$_3$—CO-

Ac3-Thr-Glu-Arg-Met-Ala]

Prepared as in Example 5B. Yield: 14.5 mg of the title compound.
MS: MW calc. 1234.45; MW obs. 1235.60 (M+1)$^+$.

Example 55

Cyclo[Leu-His-Asn-Leu-NH—(CH$_2$)$_6$—CO-Thr-Glu-Arg-Met-Gln]

Leu-His-Asn-Leu-NH—(CH$_2$)$_6$—CO-Thr-Glu-Arg-Met-Gln

A) Linear Peptide Synthesis:

(SEQ ID NO: 55)
H$_2$N—(CH$_2$)$_6$—CO-Thr(tBu)-Glu(tBu)-Arg(Pbf)-

Met-Gln(Trt)-Leu-His(Trt)-Asn(Trt)-Leu-OH

Prepared as in Example 5A, except that Fmoc-Ala-OH in step 5 was replaced with Fmoc-Gln(Trt)-OH and Ac-Lys(Fmoc)-OH in step 10 was replaced with Fmoc-7-aminoheptanoic acid. Crude product used in next step without further purification.

B) Cyclic Peptide Synthesis:

(SEQ ID NO: 111)
Cyclo[Leu-His-Asn-Leu-NH—(CH$_2$)$_6$—CO-

Thr-Glu-Arg-Met-Gln]

Prepared as in Example 5B. Yield: 25.4 mg of the title compound.
MS: MW calc. 1250.50; MW obs. 1251.61 (M+1)$^+$.

Example 56

Cyclo[Leu-His-Asn-Leu-NH—(CH$_2$)$_2$—O—(CH$_2$)$_2$—O—CH$_2$—CO-Thr-Glu-Arg-Met-Ala]

Leu-His-Asn-Leu-NH—(CH$_2$)$_2$—O—(CH$_2$)$_2$—O—CH$_2$—CO-Thr-Glu-Arg-Met-Ala

A) Linear Peptide Synthesis:

(SEQ ID NO: 56)
H$_2$N—(CH$_2$)$_2$—O—(CH$_2$)$_2$—O—CH$_2$—CO-Thr(tBu)-Glu(tBu)-

Arg(Pbf)-Met-Ala-Leu-His(Trt)-Asn(Trt)-Leu-OH

Prepared as in Example 5A, except that Ac-Lys(Fmoc)-OH in step 10 was replaced with Fmoc-NH—(CH$_2$)$_2$—O—(CH$_2$)$_2$—O—CH$_2$—COON. Crude product used in next step without further purification.

B) Cyclic Peptide Synthesis:

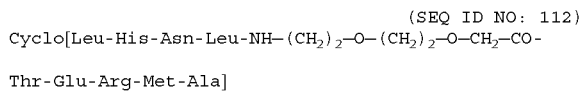

(SEQ ID NO: 112)
Cyclo[Leu-His-Asn-Leu-NH—(CH$_2$)$_2$—O—(CH$_2$)$_2$—O—CH$_2$—CO-Thr-Glu-Arg-Met-Ala]

Prepared as in Example 5B. Yield: 7.8 mg of the title compound.
MS: MW calc. 1211.42; MW obs. 1212.13 (M+1)$^+$.

Biological Testing

The compounds described above were subject to pharmacological tests.

Example A

Static Human Platelet Adhesion to Recombinant Human vWF-A1 Domain

To assess the effect of compounds on the interaction of the GPIb complex on platelets with vWF, an assay system was used measuring binding of human platelets to recombinant human vWF-A1 domain under static conditions in the presence and absence of the compounds.

Briefly, whole blood drawn from voluntary donors was sampled in syringes containing Refludan (20 µg/ml, Pharmion) and spun down for 20 min at 150 g. Platelet rich plasma was carefully removed, transferred to a fresh container and spun down for 15 min at 120 g. Platelet rich plasma was carefully transferred again to fresh containers, PGE1 (0.5 µg/ml, Sigma) was added and the suspension was allowed to rest for 5 min. This was followed by another centrifugation step for 15 min at 360 g. The supernatant was discarded and the cell pellets were carefully resuspended in tyrode buffer (NaCl, 137 mM (Sigma S-3014); KCl, 2.7 mM (Sigma P-9541); NaHCO$_3$,12 mM (Riedel deHaen 31437); NaH$_2$PO$_4$×2H$_2$O, 0.36 mM (Merck 6345); MgCl$_2$×6 H$_2$O, 1 mM (Sigma M-2670); Hepes, 10 mM (Sigma H-1016); glucose, 5.6 mM (Merck 8342); BSA, 0.1% (Sigma A7906)), and PGE1 (0.25 µg/ml) was added. After 5 min of resting the suspension was spun down for 15 min at 300 g. The supernatant was discarded and the pellets were carefully resuspended in TBS buffer (Tris-HCl, 50 mM (Fluka 93371); NaCl, 120 mM (Sigma S-3014); KCl, 2.7 mM (Sigma P-9541); CaCl$_2$, 0.05 mM (Sigma C-3306); MgCl$_2$×6 H$_2$O, 2 mM (Sigma M-2670); BSA, 0.1% (Sigma A7906); pH 7.4). The platelet count was adjusted to 2×10$^5$ cells/µl, and the suspensions from individual donors were pooled at this stage. The platelets were allowed to rest for 30 min at room temperature before calcein AM (2.5 µM per 2×10$^5$ cells/µl (Molecular Probes C-3099)) was added. This was followed by 15 min incubation in the dark. Cells were diluted to 5×10$^4$ cells/µl and ReoPro (3 µg/ml (Centocor B. V., Leiden, N L)) was added, followed by a 10 min incubation period in the dark before adding the platelets to the assay plates.

96 well plates (Greiner hb, black, clear bottom, F, 655097) were coated with human recombinant vWF-A1 domain (1.5 µg/well, AA 475-706, expressed in *E. coli*) in Tris buffer (pH 7.4; Tris-HCl, 25 mM; NaCl, 150 mM) and incubated for 1 h at room temperature. After washing the wells 3× with TBS, blocking buffer (TBS with 5% BSA) was added followed by an incubation for 1 h. The wells were washed again 3× with TBS before 200 µl TBS were added to each well, preventing them from drying out. TBS was flicked out and serial dilutions of the test compound were added. The washed and calcein AM labeled thrombocytes were added to the wells (2.5×10$^6$ cells/well). Following an adhesion period of 1.5 h in the dark the wells were washed 3× with TBS. Measurement of fluorescence per well was performed in a SpectraMax M5 reader (Molecular Devices). From the raw data % inhibition and IC$_{50}$ values were calculated.

The following results were obtained in this test with compounds of the invention described in the examples above.

| Example   | 1  | 2  | 3  | 4  | 5  | 6  | 7  | 8  | 9  |
|-----------|----|----|----|----|----|----|----|----|----|
| Activity* | C  | C  | B  | A  | B  | C  | B  | A  | A  |
| Example   | 10 | 11 | 12 | 13 | 14 | 15 | 16 | 17 | 18 |
| Activity* | B  | B  | B  | B  | B  | A  | C  | C  | B  |
| Example   | 19 | 20 | 21 | 22 | 23 | 24 | 25 | 26 | 27 |
| Activity* | C  | B  | B  | C  | A  | C  | C  | B  | A  |
| Example   | 28 | 29 | 30 | 31 | 32 | 33 | 34 | 35 | 36 |
| Activity* | C  | B  | B  | B  | C  | B  | B  | A  | C  |
| Example   | 37 | 38 | 39 | 40 | 41 | 42 | 43 | 44 | 45 |
| Activity* | B  | C  | B  | C  | C  | C  | C  | C  | C  |
| Example   | 46 | 47 | 48 | 49 | 50 | 51 | 52 | 53 | 54 |
| Activity* | B  | B  | A  | B  | B  | A  | B  | B  | B  |
| Example   | 55 |    |    |    |    |    |    |    |    |
| Activity* | B  |    |    |    |    |    |    |    |    |

*"A" means that the compound showed activity at 10 µM, "B" means an IC$_{50}$ value between 1 µM and 10 µM, "C" means an IC$_{50}$ value lower than 1 µM, for inhibition of the binding of platelets to vWF A1 domain in the above test.

Preferred compounds of the present invention are those compounds which have a IC$_{50}$≤10 µM, particularly preferably ≤1 µM, for inhibition of the binding of platelets to vWF A1 domain in the above test.

Example B

Measurement of Platelet Function by Means of PFA-100 Analyzer

The PFA-100 Analyzer (Siemens Healtclhcare Diagnostics GmbH, Marburg, Germany) measures platelet plug formation in a small, whole blood sample and reports a "closure time". It challenges platelets under high shear flow conditions similar to the physiologic environment in which platelets normally function. It simulates, in vitro, the function of platelets in primary hemostasis.

Briefly, whole blood drawn from voluntary donors was sampled in syringes containing Refludan (20 µg/ml, Pharmion) and rested for at least 30 min before use. Samples of blood were incubated in the presence or absence of the test compound in Eppendorf cups at room temperature for 10 min. Blood samples (1000 µl) were placed in Dade PFA Collagen/EPI test cartridges (Siemens Healtclhcare Diagnostics GmbH) which were pre-warmed at room temperature. The non-treated blood samples were used as controls giving a value for the minimal closure time of the cartridge. The maximal closure time of the cartridge detected by the PFA-100 was 300 sec. IC$_{50}$ values were calculated as doubling of the minimal time to closure (blood sample without compound), using 300 sec as defined maximum value. Compounds were tested in serial dilutions with at least 4 different blood donors.

The following results were obtained in this test with compounds of the invention described in the examples above.
Example 1: IC$_{50}$ (average value): <1 µM
Example 2: IC$_{50}$ (average value): <1 µM Preferred compounds of the present invention are those compounds which have a IC$_{50}$≤10 µM, particularly preferably ≤1 µM, in the above test.

Example C

Impedance Aggregometry

Whole blood agglutination induced by ristocetin, which is a specific agonist for GPIb-vWF interaction, in human whole blood was determined by means of a Multiplate Impedance Aggregometer (Instrumentation Laboratory GmbH, Kirchheim, Germany). Impedance aggregometry is based on the principle that blood platelets are non-thrombogenic in their resting state, but expose receptors on their surface when they get activated which allow them to attach on vascular injuries and artificial surfaces.

Briefly, whole blood drawn from voluntary donors was sampled in syringes containing Refludan (20 µg/ml, Pharmion) and left for 30 min at room temperature. The Multiplate instrument was adjusted to 37° C. 350 µl of whole blood where transferred to Eppendorf cups and incubated in the presence or absence of the test compound for 10 min at room temperature. 300 µl of the sample were added to 300 µl of physiological NaCl solution in a single use test cell (dynabyte medical, Munich, Germany). After 3 min incubation with agitation the agonist ristocetin (RISTOtest, dynabyte medical, 0.4-0.6 µg/ml, final concentration established in testing the individual blood donors and calculated as $IC_{80}$), or collagen (COLtest, dynabyte medical, 1.0 µg/ml), was added and the measurement started. For a period of 6 min the area under curve (AUC) is determined. Percentage of inhibition and $IC_{50}$ values were calculated from these measurements. Compounds were tested in serial dilutions with at least 4 different blood donors.

The following results were obtained in this test with compounds of the invention described in the examples above.

Example 1: $IC_{50}$ (average value): <1 µM (in the presence of ristocetin)

Example 2: $IC_{50}$ (average value): <1 µM (in the presence of ristocetin)

Preferred compounds of the present invention are those compounds which have a $IC_{50} \leq 10$ µM, particularly preferably ≤1 µM, in the above test using the agonist ristocetin while not inhibiting collagen-induced aggregation in the concentrations tested.

The invention claimed is:
1. A compound of formula I,

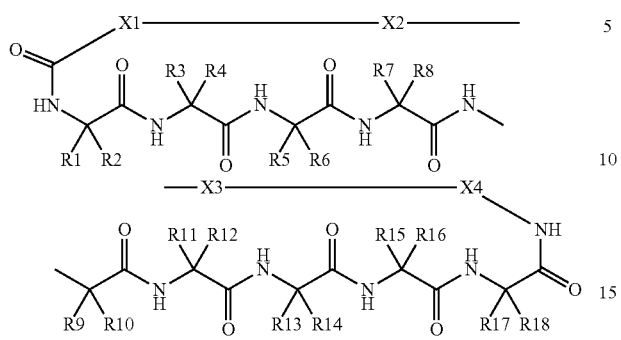

wherein
X1 is —(C$_1$-C$_6$)-alkyl-, wherein alkyl is unsubstituted or monosubstituted or disubstituted by one or two substituents independently selected from —NH—C(O)—(C$_1$-C$_6$)-alkyl, —(C$_1$-C$_6$)-alkyl-NH$_2$, —(C$_1$-C$_6$)-alkyl-C(O)—NH$_2$, and —(C$_1$-C$_6$)-alkyl,
or
X1 is

wherein n is 1, 2, 3 or 4;
X2 is a covalent bond, —(C$_1$-C$_4$)-alkyl- or phenyl, wherein phenyl is unsubstituted;
X3 is a covalent bond or phenyl, wherein phenyl is unsubstituted;
or
X2-X3 is —NH—C(O)— or —C(O)—NH—;
X4 is —(C$_1$-C$_6$)-alkyl-, wherein alkyl is unsubstituted or monosubstituted or disubstituted by one or two substituents independently selected from —NH—C(O)—(C$_1$-C$_6$)-alkyl, —(C$_1$-C$_6$)-alkyl-NH$_2$, —(C$_1$-C$_6$)-alkyl-C(O)—NH$_2$ and —(C$_1$-C$_6$)-alkyl;
or
X1-X2-X3-X4 is —(C$_1$-C$_4$)-alkyl-O—(C$_2$-C$_4$)-alkyl-O—(C$_2$-C$_4$)-alkyl-;

R1 and R2 together with the carbon atom carrying them and the NH group and the CO group attached to the said carbon atom, form the residue of L-asparagine, L-aspartic acid, L-2,4-diaminobutyric acid, L-glutamine, L-histidine, L-leucine, L-serine or L-threonine, or a pharmaceutically acceptable salt or a (C$_1$-C$_4$)-alkyl ester thereof;
R3 and R4 together with the carbon atom carrying them and the NH group and the CO group attached to the said carbon atom, form the residue of L-glutamic acid or a pharmaceutically acceptable salt or a (C$_1$-C$_4$)-alkyl ester thereof;
R5 and R6 together with the carbon atom carrying them and the NH group and the CO group attached to the said carbon atom, form the residue of L-arginine, L-2,3-diaminopropionic acid, L-lysine or L-ornithine, or a pharmaceutically acceptable salt thereof;
R7 and R8 together with the carbon atom carrying them and the NH group and the CO group attached to the said carbon atom, form the residue of L-alanine, L-2-aminobutyric acid, L-2-amino-4-methoxybutyric acid, L-2-amino-3-methoxypropionic acid, L-cyclohexylalanine, L-cyclohexylglycine, L-glutamine, L-isoleucine, L-leucine, L-methionine or L-norleucine;
R9 and R10 together with the carbon atom carrying them and the NH group and the CO group attached to the said carbon atom, form the residue of L-alanine, L-arginine, L-2,3-diaminopropionic acid, L-glutamine or L-norvaline, or a pharmaceutically acceptable salt thereof;
R11 and R12 together with the carbon atom carrying them and the NH group and the CO group attached to the said carbon atom, form the residue of 1-aminocyclohexane-1-carboxylic acid, L-cyclohexylalanine, L-cyclohexylglycine, L-isoleucine, L-leucine, L-neopentylglycine, L-norleucine or L-norvaline;
R13 and R14 together with the carbon atom carrying them and the NH group and the CO group attached to the said carbon atom, form the residue of L-histidine, D-histidine, or L-ornithine, or a pharmaceutically acceptable salt or a (C$_1$-C$_4$)-alkyl ester thereof;
R15 and R16 together with the carbon atom carrying them and the NH group and the CO group attached to the said carbon atom, form the residue of L-asparagine;
R17 and R18 together with the carbon atom carrying them and the NH group and the CO group attached to the said carbon atom, form the residue of L-leucine;
or a pharmaceutically acceptable salt thereof.

2. A compound of formula I as claimed in claim 1, which is selected from the compounds of the formulae

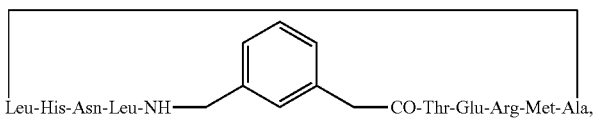

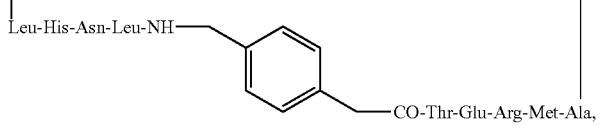

Leu-His-Asn-Leu-NH—(CH$_2$)$_6$—CO-Thr-Glu-Arg-Amp-Ala,

Leu-His-Asn-Leu-Gly-NH—(CH$_2$)$_4$—CO-Thr-Glu-Arg-Met-Ala,

Leu-His-Asn-Leu-NH—(CH$_2$)$_9$—CO-Thr-Glu-Arg-Met-Ala,

Leu-His-Asn-Leu-Gly-NH—(CH$_2$)$_3$—CO-Thr-Glu-Arg-Met-Ala,

Leu-His-Asn-Leu-Dpr-NH—(CH$_2$)$_3$—CO-Thr-Glu-Arg-Met-Ala,

Leu-His-Asn-Leu-NH—(CH$_2$)$_3$—CO-Asn-Thr-Glu-Arg-Met-Ala,

Leu-His-Asn-Leu-NH—(CH$_2$)$_2$—CO-Asn-Thr-Glu-Arg-Met-Ala,

Leu-His-Asn-Leu-NH—(CH$_2$)$_2$—CO-Ala-Thr-Glu-Arg-Met-Ala,

Leu-His-Asn-Leu-NH—(CH$_2$)$_3$—CO-Aib-Thr-Glu-Arg-Met-Ala,

Leu-His-Asn-Leu-NH—(CH$_2$)$_3$—CO-Ac3-Thr-Glu-Arg-Met-Ala,

Leu-His-Asn-Leu-NH—(CH$_2$)$_6$—CO-Thr-Glu-Arg-Met-Gln, and

Leu-His-Asn-Leu-NH—(CH$_2$)$_2$—O—(CH$_2$)$_2$—O—CH$_2$—CO-Thr-Glu-Arg-Met-Ala, or a pharmaceutically acceptable salt thereof, wherein Abu is L-2-aminobutyric acid, Ac6 is 1-aminocyclohexane-1-carboxylic acid, Aib is 2-aminoisobutyric acid, Amb is L-2-amino-4-methoxybutyric acid, Amp is L-2-amino-3-methoxypropionic acid, Cha is L-cyclohexylalanine, Chg is L-cyclohexylglycine, Dbu is L-2,4-diaminobutyric acid, Dpr is L-2,3-diaminopropionic acid, Nle is L-norleucine, Npg is L-neopentylglycine, Nva is L-norvaline Orn is L-ornithine, and Ac3 is 1-aminocyclopropane-1-carboxylic acid.

3. A pharmaceutical composition, comprising the compound of claim 1 or a pharmaceutically acceptable salt thereof and at least one pharmaceutically acceptable excipient.

* * * * *